(12) United States Patent
Wipf et al.

(10) Patent No.: US 10,544,110 B2
(45) Date of Patent: *Jan. 28, 2020

(54) SMALL MOLECULE INHIBITORS OF THE NUCLEAR TRANSLOCATION OF ANDROGEN RECEPTOR FOR THE TREATMENT OF CASTRATION-RESISTANT PROSTATE CANCER

(71) Applicant: University of Pittsburgh-Of the Commonwealth System of Higher Education, Pittsburgh, PA (US)

(72) Inventors: Peter Wipf, Pittsburgh, PA (US); James K. Johnson, Pittsburgh, PA (US); Erin M. Skoda, Columbia, MD (US); Joel B. Nelson, Pittsburgh, PA (US); Zhou Wang, Pittsburg, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/961,475

(22) Filed: Apr. 24, 2018

(65) Prior Publication Data
US 2018/0237403 A1    Aug. 23, 2018

Related U.S. Application Data

(60) Division of application No. 15/080,237, filed on Mar. 24, 2016, which is a continuation-in-part of application No. 15/023,349, filed as application No. PCT/US2014/056369 on Sep. 18, 2014.

(60) Provisional application No. 61/880,747, filed on Sep. 20, 2013.

(51) Int. Cl.
| | | |
|---|---|---|
| C07D 261/08 | (2006.01) | |
| C07D 451/00 | (2006.01) | |
| C07D 413/12 | (2006.01) | |
| A61K 31/454 | (2006.01) | |
| C07D 295/185 | (2006.01) | |
| A61K 31/495 | (2006.01) | |
| A61K 31/496 | (2006.01) | |
| A61K 31/42 | (2006.01) | |
| A61K 31/46 | (2006.01) | |
| A61K 31/4166 | (2006.01) | |
| A61K 45/06 | (2006.01) | |
| A61K 31/58 | (2006.01) | |

(52) U.S. Cl.
CPC ........ *C07D 261/08* (2013.01); *A61K 31/4166* (2013.01); *A61K 31/42* (2013.01); *A61K 31/454* (2013.01); *A61K 31/46* (2013.01); *A61K 31/495* (2013.01); *A61K 31/496* (2013.01); *A61K 31/58* (2013.01); *A61K 45/06* (2013.01); *C07D 295/185* (2013.01); *C07D 413/12* (2013.01); *C07D 451/00* (2013.01)

(58) Field of Classification Search
CPC .. C07D 261/08; C07D 413/12; C07D 451/00; C07D 295/185; A61K 45/06; A61K 31/496; A61K 31/495; A61K 31/46; A61K 31/42; A61K 31/4166; A61K 31/58; A61K 31/454
See application file for complete search history.

(56) References Cited

U.S. PATENT DOCUMENTS

| | | | |
|---|---|---|---|
| 4,186,205 | A | 1/1980 | Bender |
| 5,292,758 | A | 3/1994 | Yoshino et al. |
| 5,317,019 | A | 5/1994 | Bender et al. |
| 5,929,097 | A | 7/1999 | Levin et al. |
| 6,586,617 | B1 | 7/2003 | Tabuchi et al. |
| 6,680,342 | B2 | 1/2004 | Young et al. |

(Continued)

FOREIGN PATENT DOCUMENTS

| | | |
|---|---|---|
| EP | 1 340 749 | 9/2003 |
| EP | 1 437 349 | 7/2004 |

(Continued)

OTHER PUBLICATIONS

Ai et al., "HDAC6 Regulates Androgen Receptor Hypersensitivity and Nuclear Localization via Modulating Hsp90 Acetylation in Castration-resistant Prostate Cancer," *Mol. Endocrinol.*, 23(12): 1963-1972, 2009.

(Continued)

*Primary Examiner* — Sarah Pihonak
*Assistant Examiner* — Jason Deck
(74) *Attorney, Agent, or Firm* — Klarquist Sparkman, LLP

(57) ABSTRACT

A compound, or a pharmaceutically acceptable salt or ester thereof, according to formula I:

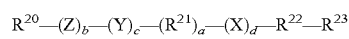

wherein $R^{20}$ is aryl, substituted aryl, heteroaryl, substituted heteroaryl, heterocycloalkyl, substituted heterocycloalkyl, alkoxy, aryloxy, a thio-containing group, or a seleno-containing group; Z is alkanediyl, substituted alkanediyl, cycloalkanediyl, or substituted cycloalkanediyl; Y is S, O, S(=O), —S(=O)(=O)—, or $NR^{10}$, wherein $R^{10}$ is H or alkyl; $R^{21}$ is alkanediyl, substituted alkanediyl, cycloalkanediyl, substituted cycloalkanediyl alkadienyl, substituted alkadienyl, alkatrienyl, substituted alkatrienyl; X is —C(=O)—, —S(=O)(=O)—, or —N(H)C(=O)—; $R^{22}$ includes at least one divalent amino radical; $R^{23}$ is aryl, substituted aryl, heteroaryl, substituted heteroaryl, heterocycloalkyl, substituted heterocycloalkyl, alkoxy, aryloxy, a thio-containing group, or a seleno-containing group; a, b, c, and d independently are 0 or 1.

16 Claims, 15 Drawing Sheets

(56) References Cited

U.S. PATENT DOCUMENTS

| | | |
|---|---|---|
| 2002/0022630 A1 | 2/2002 | Zhang et al. |
| 2004/0092529 A1 | 5/2004 | Blumberg et al. |
| 2007/0142394 A1 | 6/2007 | Solomon et al. |
| 2009/0163545 A1 | 6/2009 | Goldfarb |
| 2010/0094006 A1 | 4/2010 | Nam et al. |
| 2011/0003839 A1 | 1/2011 | Jung et al. |
| 2012/0264744 A1 | 10/2012 | Dasgupta et al. |
| 2013/0211075 A1 | 8/2013 | Ushio et al. |
| 2017/0246164 A1 | 8/2017 | Wang et al. |

FOREIGN PATENT DOCUMENTS

| | | |
|---|---|---|
| EP | 1 992 618 A1 | 11/2008 |
| JP | 2001 261657 | 9/2001 |
| WO | WO 99/02502 | 1/1999 |
| WO | WO 00/54759 | 9/2000 |
| WO | WO 2001/029038 | 4/2001 |
| WO | WO 02/30879 | 4/2002 |
| WO | WO 2004/014300 | 2/2004 |
| WO | WO 2004/073634 | 9/2004 |
| WO | WO 2005/040114 | 5/2005 |
| WO | WO 2005/079270 | 9/2005 |
| WO | WO 2005/121130 | 12/2005 |
| WO | WO 2006/030977 | 3/2006 |
| WO | WO 2006/044504 | 4/2006 |
| WO | WO 2007/001701 | 1/2007 |
| WO | WO 2007/061360 | 5/2007 |
| WO | WO 2007/071440 | 6/2007 |
| WO | WO 2007/071443 | 6/2007 |
| WO | WO 2007/076055 | 7/2007 |
| WO | WO 2008/011130 | 1/2008 |
| WO | WO 2008/027584 | 3/2008 |
| WO | WO 2008/060998 | 5/2008 |
| WO | WO 2008/114022 | 9/2008 |
| WO | WO 2009/092585 | 7/2009 |
| WO | WO 2009/125923 | 10/2009 |
| WO | WO 2011/032169 | 3/2011 |
| WO | WO 2011/050353 | 4/2011 |
| WO | WO 2013/055793 | 4/2013 |
| WO | WO 2013/117963 | 8/2013 |
| WO | WO 2015/042297 | 3/2015 |

OTHER PUBLICATIONS

Bravo-Altamirano et al. "Synthesis and Structure—Activity Relationships of Benzothienothiazepinone Inhibitors of Protein Kinase D," *ACS Med. Chem. Lett.*. vol. 2, pp. 154-159, 2011.
CAS RN 312929-26-3, STN Entry Date: Jan. 5, 2001.
CAS RN 321981-09-3, STN Entry Date: Feb. 19, 2001.
CAS RN 326014-86-2, STN Entry Date: Mar. 7, 2001.
CAS RN 344565-06-6, STN Entry Date: Jul. 5, 2001.
CAS RN 345293-88-1, STN Entry Date: Jul. 11, 2001.
CAS RN 475196-08-8, STN Entry Date: Dec. 5, 2002.
CAS RN 790203-53-1, STN Entry Date: Nov. 29, 2004.
CAS RN 893704-98-8, STN Entry Date: Jul. 17, 2006.
CAS RN 1172844-15-3, STN Entry Date: Aug. 5, 2009.
CAS RN 1179384-26-9, STN Entry Date: Sep. 2, 2009.
CAS RN 1179381-92-0, STN Entry Date: Sep. 2, 2009.
CAS RN 1179402-21-1, STN Entry Date: Sep. 2, 2009.
CAS RN 1624152-83-5, STN Entry Date: Sep. 22, 2014.
CAS RN 1624387-89-8, STN Entry Date: Sep. 23, 2014.
CAS RN 1646734-73-7, STN Entry Date: Feb. 12, 2015.
CAS RN 1647452-68-3, STN Entry Date: Feb. 15, 2015.
Clausen et al. "In Vitro Cytoxicity and In Vivo Efficacy, Pharmacokinetics, and Metabolism of 10074-G5, a Novel Small-MoleculeInhibitor of c-Myc/Max Dimerization," *The Journal of Pharmacology and Experimental Therapeutics*, vol. 335, No. 3, pp. 715-727, 2010.
Claxton et al., "Cyclization of Lactamimide Ketones to Imidazo[1,2-a]-azacycloalkanes with Hypoglycemic Activity," *Journal of Medicinal Chemistry*, vol. 17, No. 3, pp. 364-367, 1974.
Demchenko et al., "Synthesis and Antifungal Activity of 3-aryl-6,7-dihydro-5H-pyrrolo[1,2-a imidazoles," translated from *Khimiko-Farmatsevticheskii Zhurnal*, vol. 21, No. 22, pp. 1335-1338, 1978.

Extended European Search Report issued by the European Patent Office for EPC Application No. EP 14846330 dated Jun. 14, 2017.
Frantz et al. "Large-Scale asymmetric Synthesis of the Bioprotective Agent JP4-039 and Analogs," *Organic Letters*, 2011.
Frutos et al. "Expedient synthesis of substituted imidazoles from nitriles," *Tetrahedrom Letters*, vol. 46, pp. 8369-8372, 2005.
Graczyk et al., "The neuroprotective action of JNK3 inhibitors based on the 6,7-dihydro-5H-pyrrolo[1,2-a]imidazole scaffold," *Bioorganic & Medical Chemistry Letters*, vol. 15, pp. 4666-4670, 2005.
International Search Report and Written Opinion issued in International Application No. PCT/US2012/059558, dated Jan. 18, 2013, 20 pages.
International Search Report and Written Opinion issued in International Application No. PCT/US2014/056369 dated Jan. 14, 2015, 12 pages.
International Search Report and Written Opinion for corresponding International Application No. PCT/US2017/024105, dated Jun. 29, 2017.
Kovtunenko et al., "Derivatives of 1,2-tetramethyleneimidazole," *Ukrainskii Khimicheskii Zhurna* (Russian Edition), vol. 62(3-4), pp. 111-117, 1996 (translated abstract only).
Kovtunenko et al., "Derivatives of 2a,4a-diazacyclopent[c,d]azulene," *Khimiya Geterotsiklicheskikh Soedinenii*, vol. 8, pp. 1072-1077, 1996 (translated abstract only).
Liu et al., "A general and convenient synthesis of N-aryl piperazines," *Tetrahedron Letters*, vol. 46, pp. 7921-7922, 2005.
Non-Final Office Action issued for U.S. Appl. No. 15/023,349 dated Feb. 27, 2017.
O'Shaughnessy et al, "Synthesis of Pyrrolo- and Pyrido-[1,2-a]benzimidazolequinone Anti-tumor Agents Containing a Fused Cyclopropane Ring," *Synthesis*, vol. 7, pp. 1069-1076, 2005.
Paone et al., "Orally Bioavailable Imidazoazepanes as Calcitonin Gene-Related Peptide (CGRP) Receptor Antagonists: Discovery of MK-2918," *Bioorganic and Medicinal Chemistry Letters*, vol. 21, pp. 2683-2686, 2011.
PubChem entry for SCHEMBL 18061526—alleged "create date" of May 29, 2009.
PubChem entry for ST50917073 entered Sep. 13, 2005.
PubChem entry for ACILTCGH entered Jul. 11, 2005.
PubChem entry for CID24884553 entered Sep. 8, 2008.
PubChem database entry for SCH EM BL 18061517 created May 29, 2009.
Ren et al., "Pharmacophore Modeling and Virtual Screening for the Discovery of New Transforming Growth Factor-Beta Type I Receptor (ALKS) Inhibitors," European Journal of Medicinal Chemistry, 2009, vol. 44, pp. 4259-4265.
Saporita et al, "The Hsp90 Inhibitor, 17-AAG, Prevents the Ligand-Independent Nuclear Localization of Androgen Receptor in Refractory Prostate Cancer Cells," *The Prostate*, 67:509-520, 2007.
Sasaki et al., "Ring Transformation of Oxazoles to Fused Imidazoles. New Synthetic Route for 6-methyl-2,3-diphenyl-7,8-dihydroimidazo[1m2-b]pyridazine and 5-methyl-2,3-diphenyl-6,7-dihydro-5H-pyrrolo[1,2-a]imidazole, and their perhydrobenzo analogs," *Journal of Chemical Society, Perkins Transactions 1: Organic and Bio-Organic Chemistry*, 1983, vol. 12, pp. 3027-3030.
Valade et al., "Discovery of novel selective Sigma-1 ligands as cognitive enhancers," *MedChemComm*, 2(7): 655-660, Jun. 10, 2011.
Whitlock et al., "Potent and selective $\alpha_{1A}$ adrenoceptor partial agonists—Novel imidazole frameworks," *Bioorganic & Medicinal Chemistry Letters*, 19: 3118-3121, 2009.
Yamaguchi et al., "Construction of a cis-Cyclopropane via Reductive Radical Decarboxylation. Enantioselective Synthesis of cis- and trans-1-Arylpiperazyl-2-phenylcyclopropanes Designed as Antidopaminergic Agents," J. Org. Chem., vol. 68, pp. 9255-9262, 2003.
ZINC17074676 added Sep. 13, 2008.
ZINC2562103 added Oct. 27, 2004.
ZINC25951622 added Feb. 2, 2009.
ZINC25951626 added Feb. 2, 2009.
ZINC25951633 added Feb. 2, 2009.
ZINC25958726 added Feb. 2, 2009.

(56) References Cited

OTHER PUBLICATIONS

ZINC25958734 added Feb. 2, 2009.
ZINC303410047 added Mar. 11, 2016.
ZINC303692363 added Mar. 11, 2016.
ZINC303878919 added Mar. 11, 2016.
ZINC30778696 added Apr. 2, 2009.
ZINC30778703 added Apr. 2, 2009.
ZINC3135710 added Nov. 6, 2004.
ZINC38946613 added Feb. 1, 2010.
ZINC38946614 added Feb. 1, 2010.
ZINC38946616 added Feb. 1, 2010.
ZINC39755011 added Mar. 7, 2010.
ZINC54116237 added Nov. 30, 2010.
ZINC54116241 added Nov. 30, 2010.
ZINC58469525 added Feb. 7, 2011.
ZINC72011928 added Feb. 23, 2012.
ZINC92210938 added Jun. 14, 2013.
ZINC92210944 added Jun. 14, 2013.

| Compound Name | Shortened # | Structure | MW (exact) | Formula |
|---|---|---|---|---|
| PW9-09 | 909 | 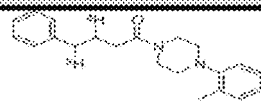 | 326.22 | C21H24T2N2O |
| MK504-92 | 492 | 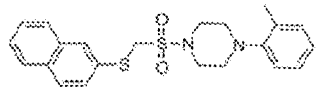 | 412.13 | C22H24N2O2S2 |
| MK504-91 | 491 | 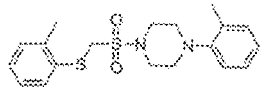 | 376.13 | C19H24N2O2S2 |
| MK504-90 | 490 | 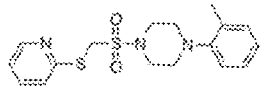 | 363.11 | C17H21N3O2S2 |
| EMS386-73 | 673 | 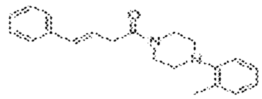 | 320.43 | C21H24N2O |
| MK504-63 | 463 | 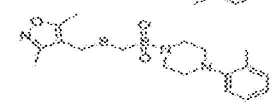 | 395.13 | C18H25N3O3S2 |
| MK504-37 | 437 | 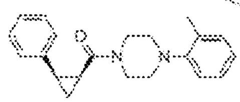 | 320.19 | C21H24N2O |
| EMS386-23 | 623 | 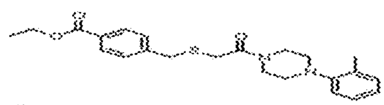 | 412.18 | C23H28N2O3S |
| EMS386-15 | 615 | 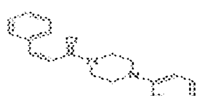 | 306.17 | C20H22N2O |
| EMS386-08 | 608 | 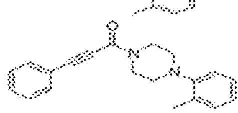 | 308.16 | C20H20N2O |
| EMS386-07 | 607 | 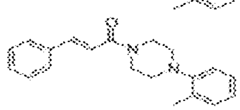 | 306.17 | C20H22N2O |
| BRE490-17 | 17 | 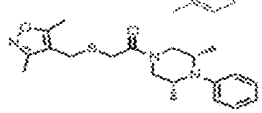 | 373.18 | C20H27N3O2S |
| BRE490-18 | 18 | 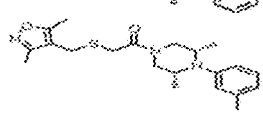 | 387.2 | C21H29N3O2S |
| BRE490-22 | 22 | 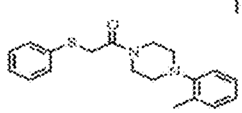 | 326.15 | C19H22N2OS |
| BRE454-84 | 484 | 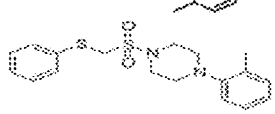 | 362.11 | C18H22N2O2S2 |
| MK415-59 | 559 | 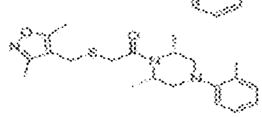 | 387.54 | C21H29N3O2S |
| MK415-62 | 562 | 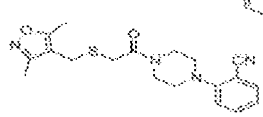 | 370.47 | C19H22N4O2S |

FIG. 1B

| ID | # | Structure | MW | Formula |
|---|---|---|---|---|
| MK415-63 | 563 | 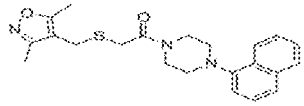 | 395.52 | C22H25N3O2S |
| MK415-48 | 548 | 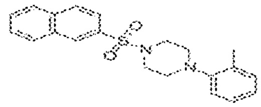 | 366.48 | C21H22N2O2S |
| MK415-53 | 553 | 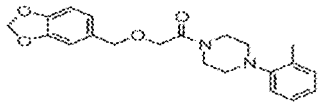 | 368.43 | C21H24N2O4 |
| MK415-47 | 547 | 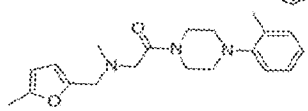 | 341.45 | C20H27N3O2 |
| BRE454-62 | 462 | 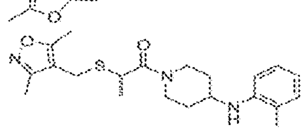 | 387.54 | C21H29N3O2S |
| BRE454-75 | 475 | 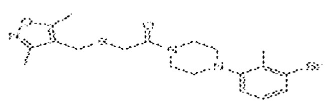 | 438.38 | C19H24BrN3O2S |
| BRE454-76 | 476 | 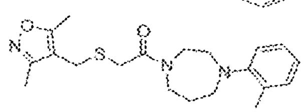 | 373.41 | C20H27N3O2S |
| BRE454-71 | 471 | 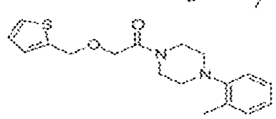 | 330.14 | C18H22N2O2S |
| BRE454-78 | 478 | 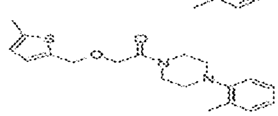 | 344.16 | C19H24N2O2S |
| BRE454-58 | 458 | 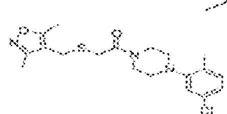 | 393.93 | C19H24ClN3O2S |
| BRE454-56 | 456 | 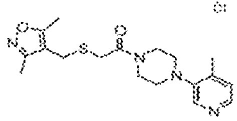 | 360.47 | C18H24N4O2S |
| BRE454-46 | 446 | 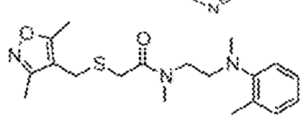 | 361.5 | C19H27N3O2S |
| MK415-43-2 | 543 | 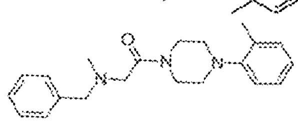 | 337.46 | C21H27N3O |
| BRE454-43 | 443 | 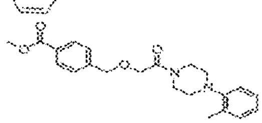 | 382.45 | C22H26N2O4 |
| BRE454-54 | 454 | 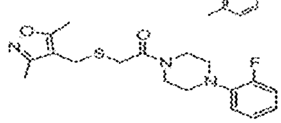 | 363.45 | C18H22FN3O2S |
| BRE454-47 | 447 | 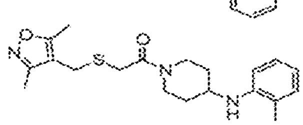 | 373.51 | C20H27N3O2S |

FIG. 1C

| # | Structure | Mass | Formula |
|---|---|---|---|
| 5i | 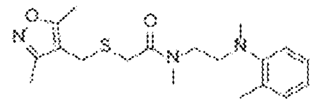 | 362.19 | C₁₈H₂₆N₃O₂S |
| 6 | 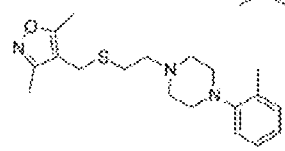 | 346.19 | C₁₉H₂₈ON₃S |
| 7 | 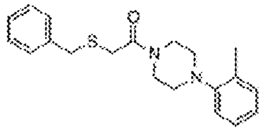 | 341.17 | C₂₀H₂₅N₂OS |
| 12 | 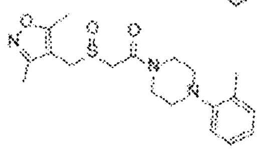 | 376.17 | C₁₉H₂₆N₃O₃S |
| 13 | 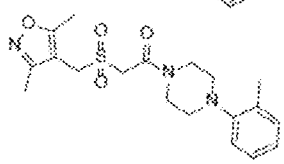 | 392.16 | C₁₉H₂₆N₃O₄S |
| 16 | 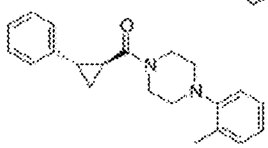 | 321.20 | C₂₁H₂₃ON₂ |
| 18a | 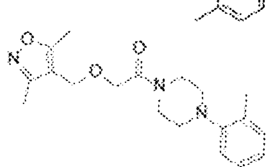 | 344.20 | C₁₈H₂₆N₃O₃ |
| 20a | 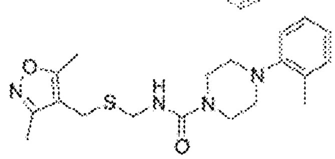 | 375.18 | C₁₈H₂₇N₄O₂S |
| 20b | 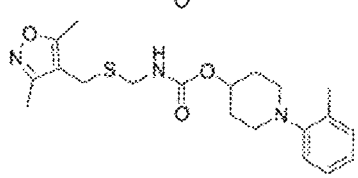 | 390.18 | C₂₀H₂₈N₃O₃S |
| 26a | 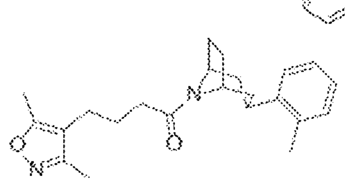 | 385.19 | C₂₂H₂₉O₂N₂S |
| 26b | 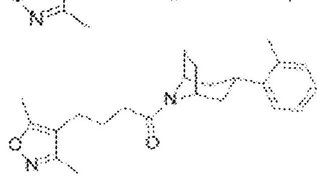 | 385.19 | C₂₂H₂₉O₂N₂S |

| | | | |
|---|---|---|---|
| JJ-450 |  | 373.15 | C₂₁H₂₃ClFON₂ |
| JJ-450A |  | 373.15 | C₂₁H₂₃ClFON₂ |
| JJ-450B |  | 373.15 | C₂₁H₂₃ClFON₂ |

Scheme 1

3b: X = CH$_2$SCH$_2$
3c: X = (CH$_2$)$_3$
3d: X = SCH$_2$
3e: X = C≡C
3f: X = (E)-CH=CH
3g: X = trans-C$_3$H$_4$ Scheme 2

Scheme 3

Scheme 4

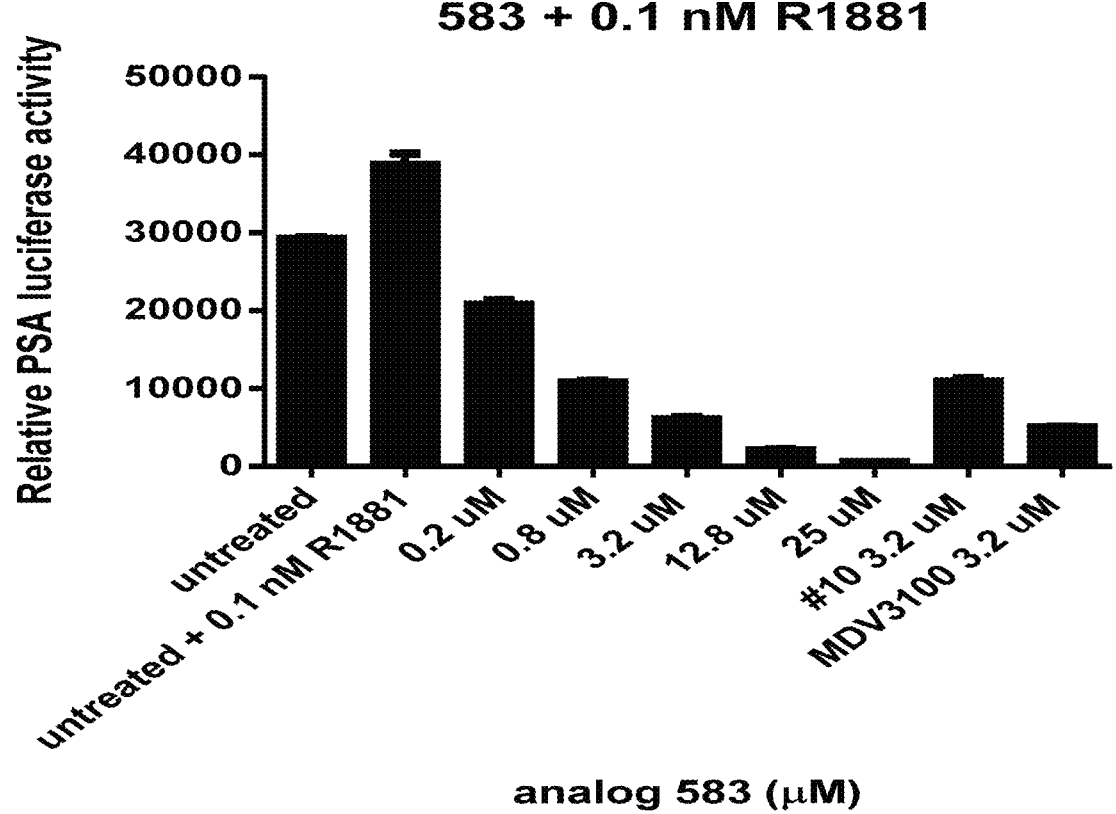
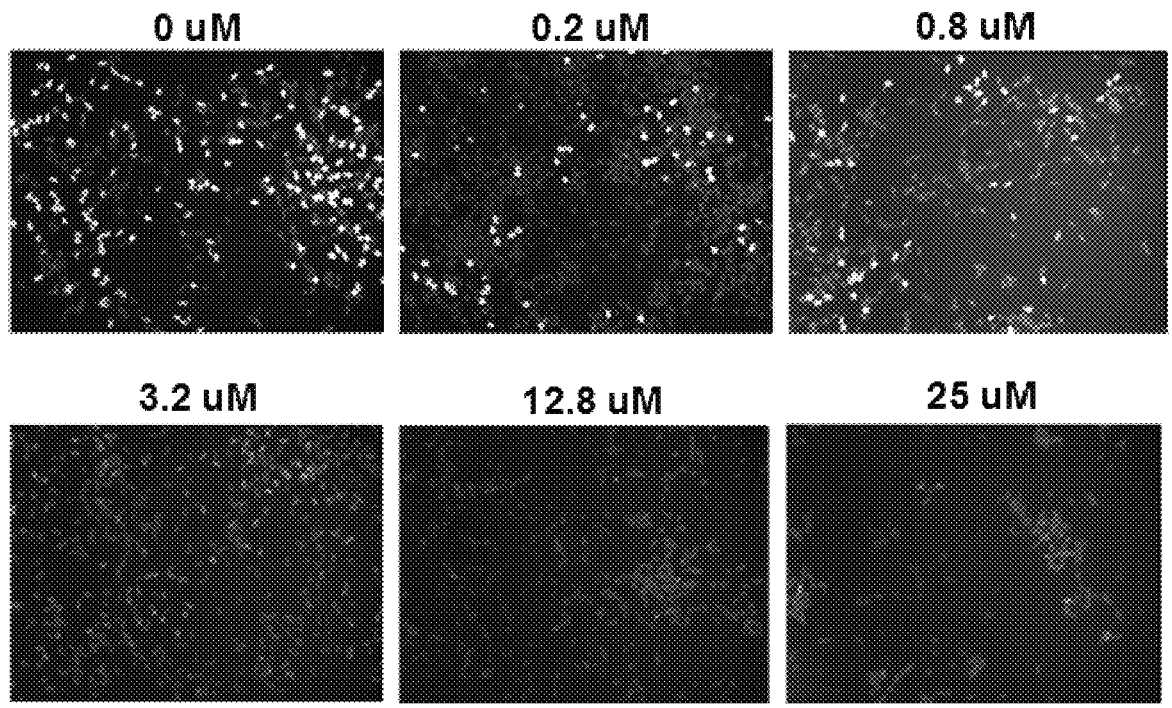

571 + 0.1 nM R1881 analog 571 (µM)

SMALL MOLECULE INHIBITORS OF THE NUCLEAR TRANSLOCATION OF ANDROGEN RECEPTOR FOR THE TREATMENT OF CASTRATION-RESISTANT PROSTATE CANCER

This application is a divisional of U.S. application Ser. No. 15/080,237, filed Mar. 24, 2016, now abandoned, which is a continuation-in-part of U.S. application Ser. No. 15/023,349, filed Mar. 18, 2016, which is the U.S. National Stage of International Application No. PCT/US2014/056369, filed Sep. 18, 2014, which was published in English under PCT Article 21(2), which in turn claims the benefit of U.S. Provisional Application No. 61/880,747, filed Sep. 20, 2013, each of which is incorporated in its entirety herein by reference.

ACKNOWLEDGMENT OF GOVERNMENT SUPPORT

This invention was made with government support under grant #GM067082 awarded by the National Institutes of Health. The government has certain rights in the invention.

BACKGROUND

Castration-resistant prostate cancer (CRPC) is currently incurable and makes prostate cancer the second most common cause of cancer death among men in the United States. The androgen receptor (AR) is activated via multiple mechanisms including AR overexpression, mutation, hypersensitization, and/or intratumoral androgen synthesis in patients relapsed after androgen deprivation therapy (ADT). The steroidal hormones testosterone and dihydrotestosterone are the major endogenous androgens that cause nuclear translocation and subsequent activation of androgen receptor (AR). Overexpression and knockdown studies have demonstrated that AR is a key molecular determinant and an excellent therapeutic target for CRPC. Clinical use of abiraterone, a potent inhibitor of testosterone synthesis, and MDV3100 (enzalutamide) and bicalutamide, AR antagonists, indicates that AR remains a viable target in a significant number of CRPC patients.

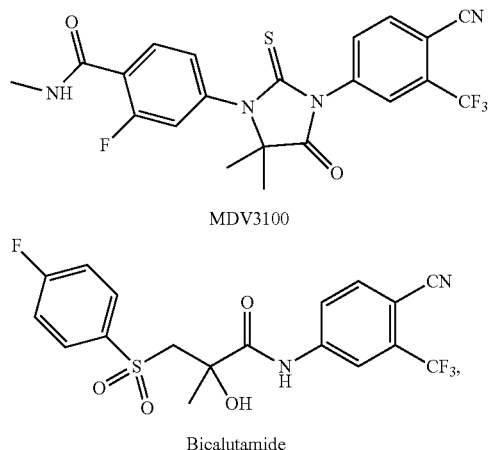

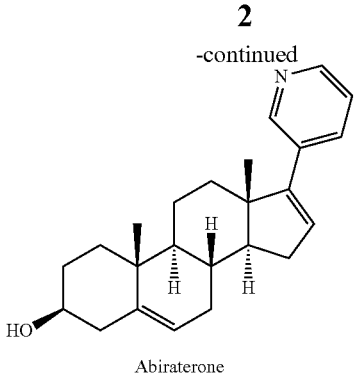

Abiraterone

Androgen receptor (AR), a member of the steroid receptor superfamily, is a ligand-dependent transcription factor that controls the expression of androgen-responsive genes. Intracellular trafficking is an important mechanism in the regulation of many transcription factors, including AR. In order to access its target genes, a transcription factor requires localization to the nucleus. Retention of a transcription factor in the cytoplasm prevents its activity. Thus, a key regulatory step in the action of AR is its nuclear translocation. In androgen-sensitive cells, AR is localized to the cytoplasm in the absence of ligand. Upon addition of androgens, AR translocates to the nucleus and transactivates target genes. However, in CRPC cells, AR remains in the nucleus even in the absence of androgen and transactivates androgen-responsive genes, leading to uncontrolled growth of prostate tumors. Therefore, novel approaches that can block the nuclear localization of AR, degrade nuclear AR, and/or suppress nuclear AR activity may provide an effective therapy against CRPC.

SUMMARY

Disclosed herein is a compound, or a pharmaceutically acceptable salt or ester thereof, having a formula I of:

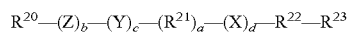

$$R^{20}-(Z)_b-(Y)_c-(R^{21})_a-(X)_d-R^{22}-R^{23}$$

wherein $R^{20}$ is an aryl, substituted aryl, heteroaryl, substituted heteroaryl, heterocycloalkyl, substituted heterocycloalkyl, alkoxy, aryloxy, amino, a thio-containing group, or a seleno-containing group; Z is alkanediyl, substituted alkanediyl, cycloalkanediyl, or substituted cycloalkanediyl; Y is S, O, S(=O), —S(=O)(=O)—, or $NR^{10}$, wherein $R^{10}$ is H or alkyl; $R^{21}$ is alkanediyl, substituted alkanediyl, cycloalkanediyl, substituted cycloalkanediyl alkadienyl, substituted alkadienyl, alkatrienyl, substituted alkatrienyl; X is —C(=O)—, —S(=O)(=O)—, or —N(H)C(=O)—; $R^{22}$ is a moiety that includes at least one divalent amino radical; $R^{23}$ is an aryl, substituted aryl, heteroaryl, substituted heteroaryl, heterocycloalkyl, substituted heterocycloalkyl, alkoxy, aryloxy, amino, a thio-containing group, a seleno-containing group; a is 0 or 1; b is 0 or 1; c is 0 or 1; and d is 0 or 1. In some embodiments, if X is —C(=O)— then Y is not S. In certain embodiments, $R^{21}$ is cycloalkanediyl. When $R^{21}$ is cycloalkanediyl, $R^{20}$ may be a phenyl optionally substituted with at least one halogen and/or $R^{23}$ may be a phenyl substituted with at least one halogen and/or at least one alkyl.

Also disclosed herein is a method for treating prostate cancer in a subject, comprising administering a therapeutically effective amount of an agent to the subject, wherein the agent is a compound, or a pharmaceutically acceptable salt or ester thereof, of formula I or formula II.

The foregoing will become more apparent from the following detailed description, which proceeds with reference to the accompanying figures.

BRIEF DESCRIPTION OF THE DRAWINGS

FIGS. 1A through 1D are a table showing compound structures.

FIG. 9A is a graph showing the effect of compound #583 at indicated concentrations on PSA-driven luciferase activity in C4-2 cells.

FIG. 9B shows the effect of compound #583 at indicated concentrations on C4-2 cell proliferation in BrdU assay.

DETAILED DESCRIPTION

Figure 1A:
Figure 1A:
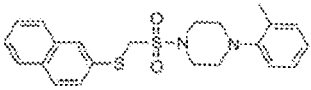
Figure 1A:
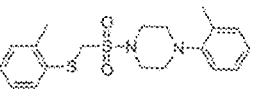
Figure 1A:
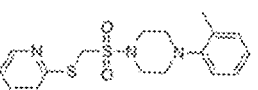
Figure 1A:
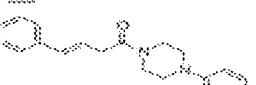
Figure 1A:
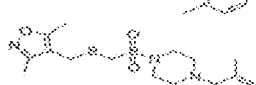
Figure 1A:
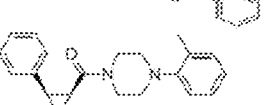
Figure 1A:
Figure 1A:
Figure 1A:
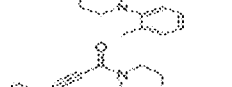
Figure 1A:
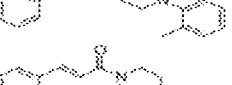
Figure 1A:
Figure 1A:
Figure 1A:
Figure 1A:
Figure 1A:
Figure 1A:
Figure 1D:
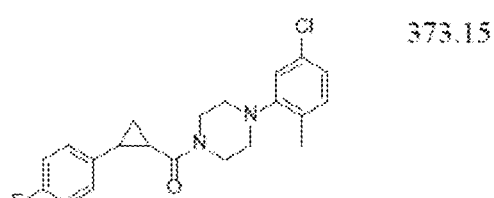
Figure 1D:
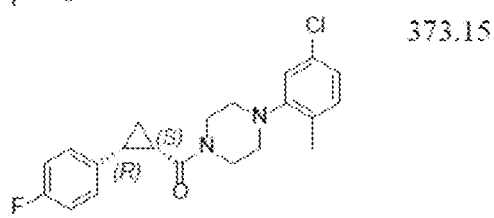
Figure 1D:
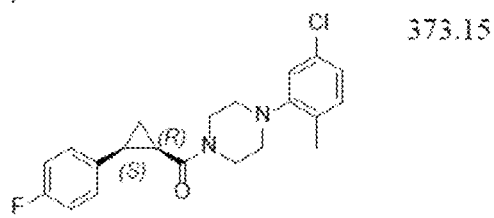
Figure 2A:
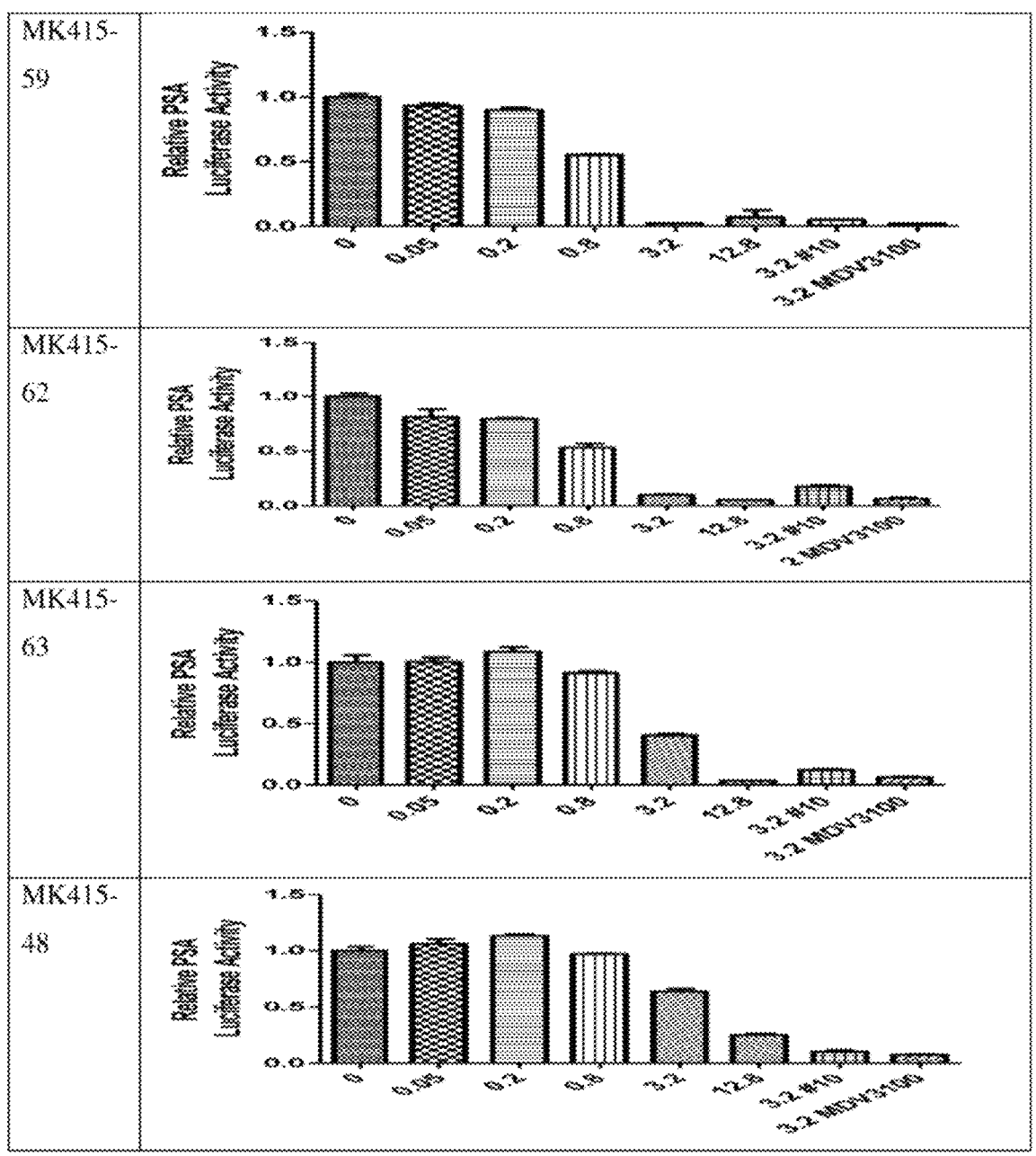
FIGS. 2A through 2E show assay results for several of the compounds. C4-2 cells were transfected with PSA6.1-Luc, GFP-AR, and pRL-CMV and then treated with indicated doses for 24 hours. For luciferase assays, cells were lysed with passive lysis buffer (Promega) and both Firefly and *Renilla* luciferase activities were read using a Dual-Luciferase Reporter Assay kit (Promega) on a LmaxII384 luminometer (Molecular Devices). Firefly luciferase values were normalized to *Renilla* (pRL-CMV). Plotted values represent averaged normalized Firefly luciferase activities, each performed in triplicate, relative to DMSO control. This assay is described in more detail in PCT Patent Application Publication WO 2013055793, which is incorporated herein by reference.
Figure 2B:
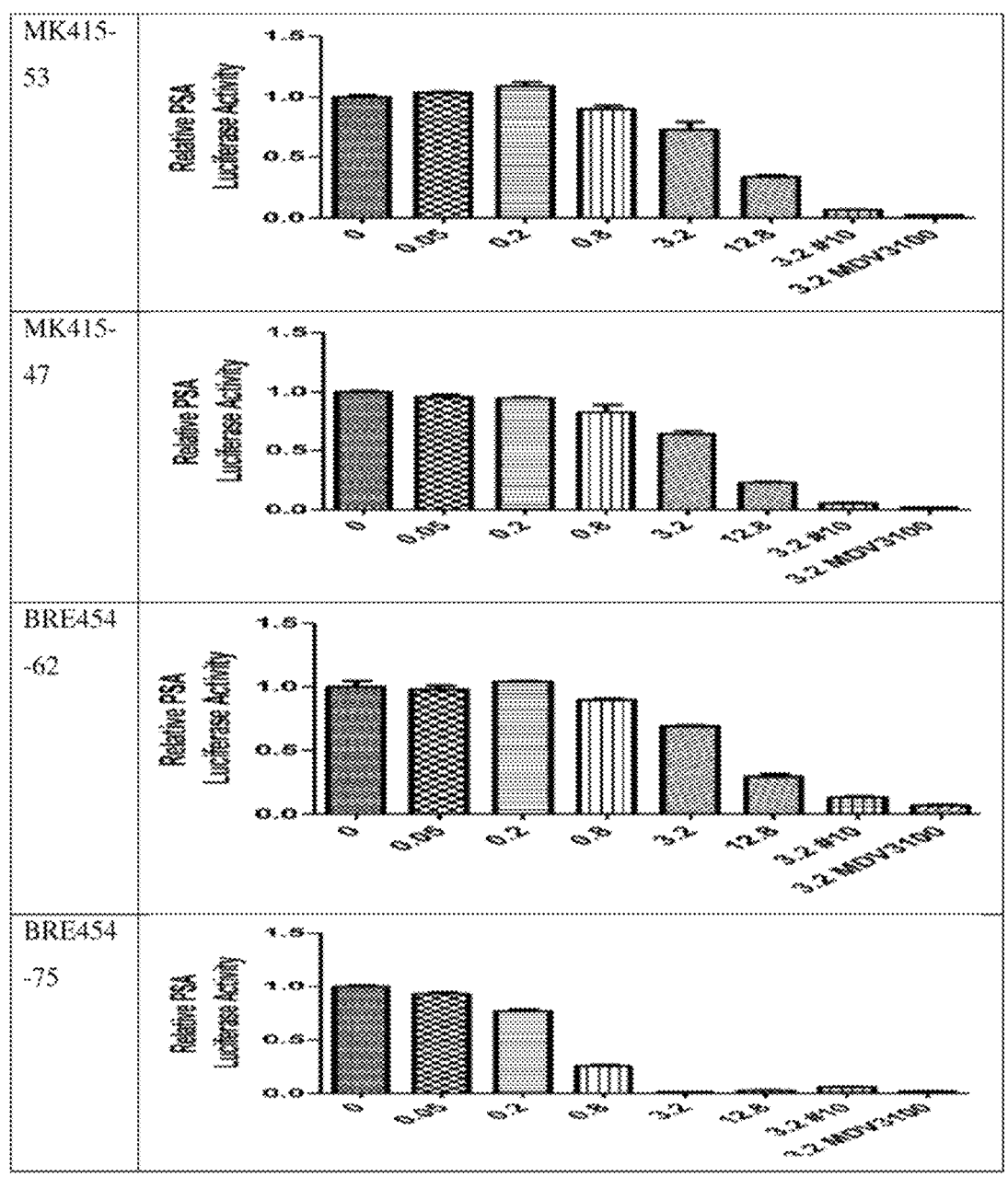
Figure 2C:
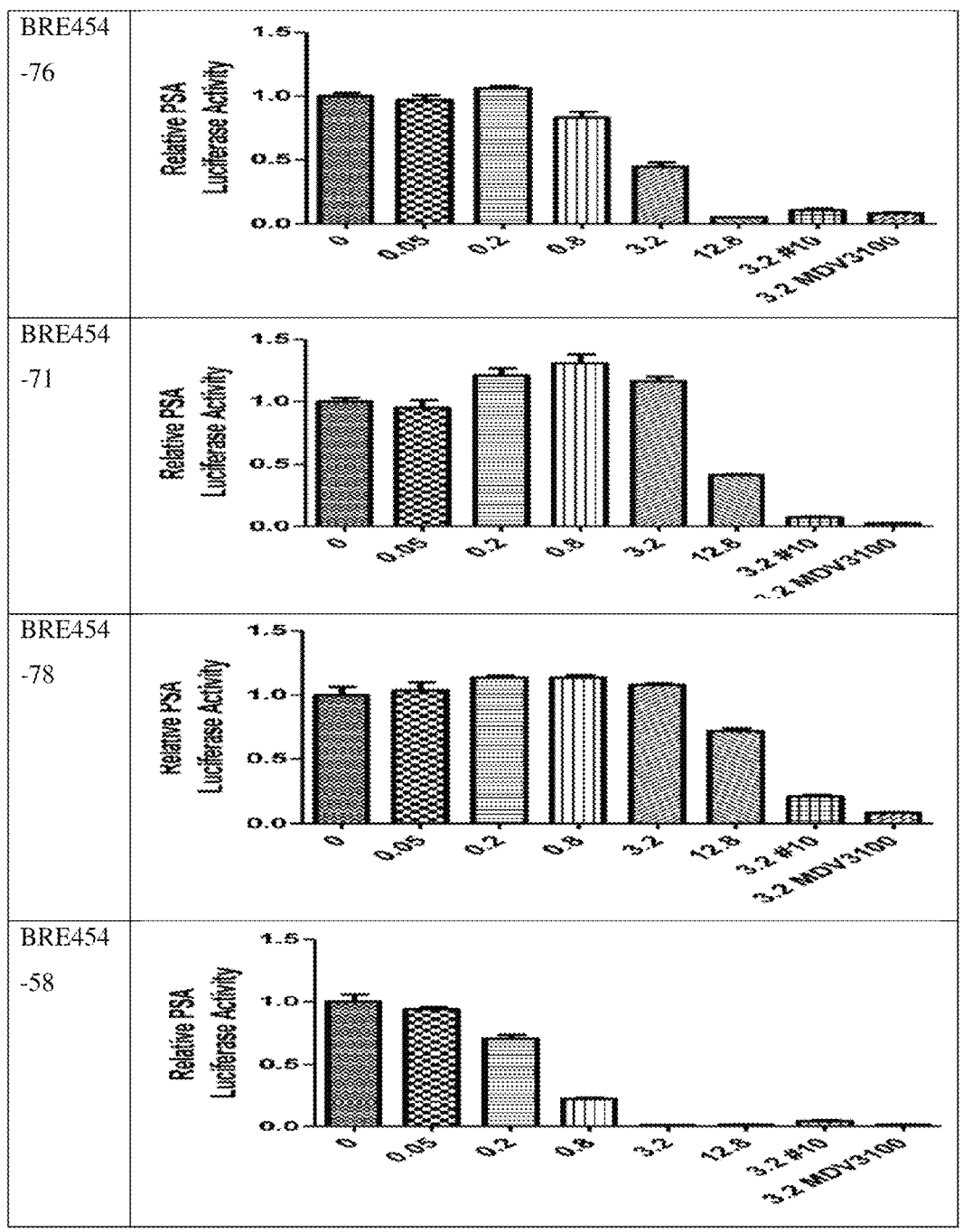
Figure 2D:
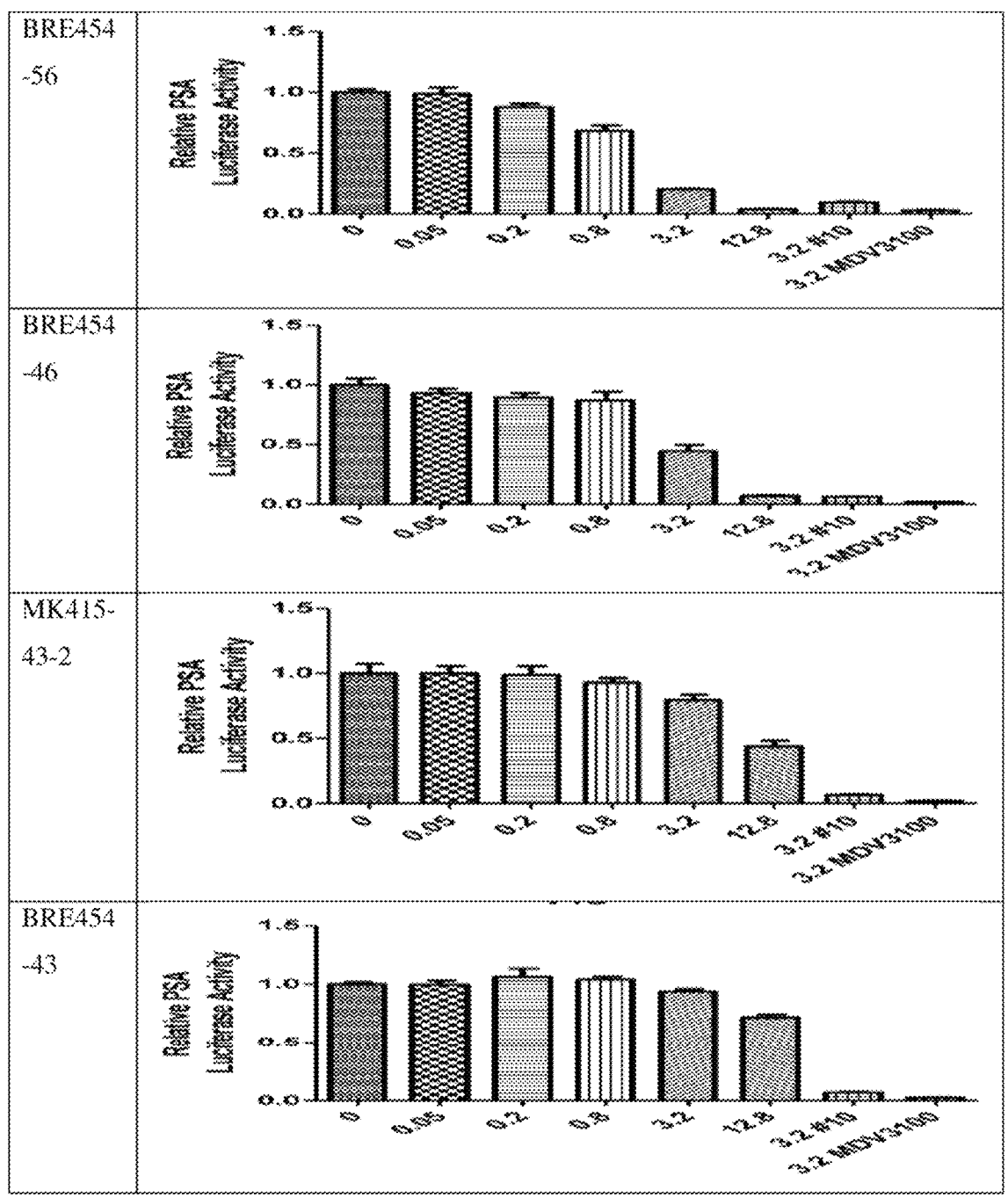
Figure 2E:
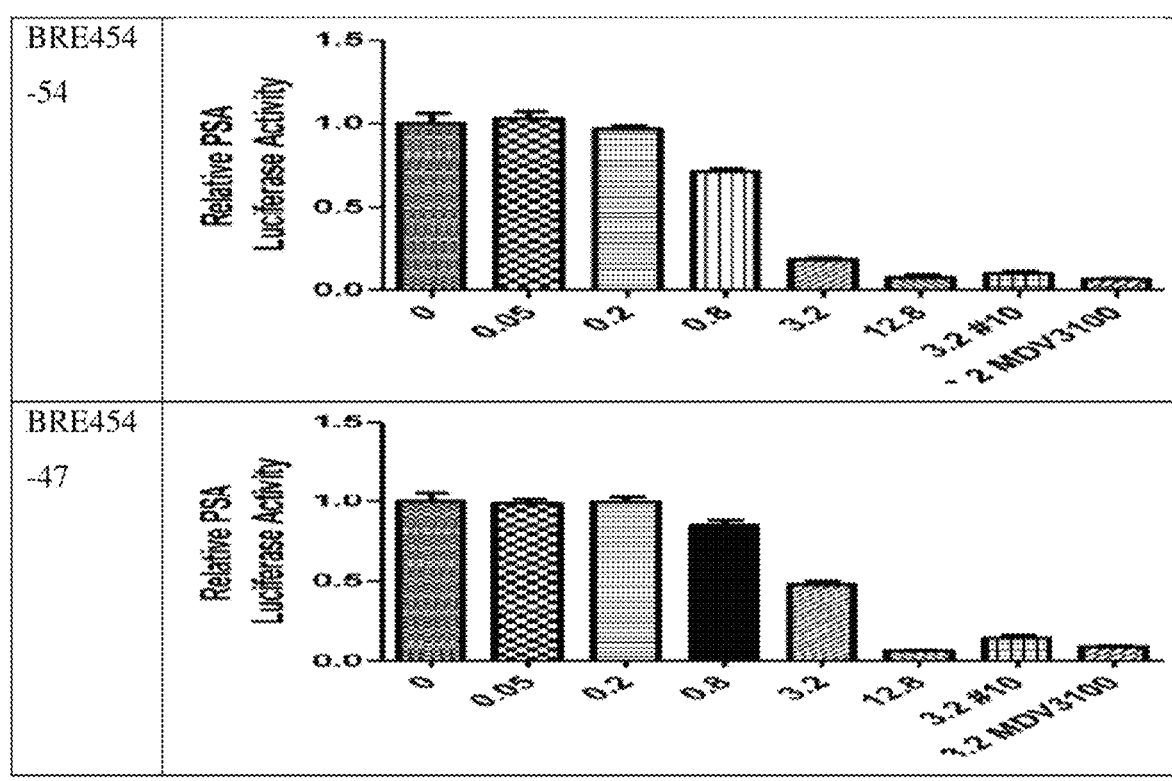

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

"Alkanediyl" or "cycloalkanediyl" refers to a divalent radical of the general formula $-C_nH_{2n}-$ derived from aliphatic or cycloaliphatic hydrocarbons.

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$ alkanoyl can be acetyl, propanoyl or butanoyl; halo$(C_1-C_6)$ alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "alkylaryl" refers to a group in which an alkyl group is substituted for a hydrogen atom of an aryl group. An example is —Ar—R, wherein Ar is an arylene group and R is an alkyl group.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amide" or "amido" is represented by the formula —C(O)NRR', where R and R' independently can be a hydrogen, alkyl, alkenyl, alkynyl, aryl, arylalkyl, cycloalkyl, halogenated alkyl, or heterocycloalkyl group described above. A suitable amido group is acetamido.

The term "amine" or "amino" refers to a group of the formula —NRR', where R and R' can be, independently, hydrogen or an alkyl, alkenyl, alkynyl, aryl, arylalkyl, carbonyl (e.g, —C(O)R", where R" can be hydrogen, an alkyl, alkenyl, alkynyl, aryl, or an arylalkyl), cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, arylalkyl, cycloalkyl, cycloalkylalkyl, alkanoyl, alkoxycarbonyl, aralkoxycarbonyl and the like. An aminocarbonyl group may be —C(O)—N(R) (wherein R is a substituted group or H). An "aminocarbonyl" is inclusive of an amido group. A suitable aminocarbonyl group is acetamido.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. Structural analogs are often found using quantitative structure activity relationships (QSAR), with techniques such as those disclosed in Remington (*The Science and Practice of Pharmacology*, 19th Edition (1995), chapter 28). A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aryl" refers to any carbon-based aromatic group including, but not limited to, phenyl, naphthyl, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "arylalkyl" refers to an alkyl group where at least one hydrogen atom is substituted by an aryl group. An example of an arylalkyl group is a benzyl group.

"Carbonyl" refers to a group of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COO group. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "co-administration" or "co-administering" refers to administration of a first agent with a second agent within the same general time period, and does not require administration at the same exact moment in time (although co-administration is inclusive of administering at the same exact moment in time). Thus, co-administration may be on the same day or on different days, or in the same week or in different weeks. The first agent and the second agent may be included in the same composition or they may each individually be included in separate compositions. In certain embodiments, the two agents may be administered during a time frame wherein their respective periods of biological activity overlap. Thus, the term includes sequential as well as coextensive administration of two or more agents.

"Derivative" refers to a compound or portion of a compound that is derived from or is theoretically derivable from a parent compound.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino Unless otherwise defined optionally substituted N-heterocyclics includes pyridinium salts and the N-oxide form of suitable ring nitrogens.

Examples of N-heterocycles also include bridged groups such as, for example, azabicyclo (for example, azabicyclooctane).

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), arylalkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or arylalkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

Some of the compounds described herein may also exist in their tautomeric form.

The term "subject" includes both human and veterinary subjects.

A "therapeutically effective amount" or "diagnostically effective amount" refers to a quantity of a specified agent sufficient to achieve a desired effect in a subject being treated with that agent. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

Overview

CRPC is responsible for all prostate cancer deaths, and eventually all prostate cancer will develop into CRPC. The current best treatment for CRPC is MDV3100 (enzalutamide), which binds to androgen receptor. It is effective against a number of androgen-dependent prostate cancer cell lines. However, it is ineffective against the androgen-dependent prostate cancer cell line 22Rv1. Compounds disclosed herein are effective against all androgen-dependent cell lines tested including 22Rv1, a promising and unique property.

Several of the compounds show sub-micromolar inhibition of PSA-luciferase expression in C4-2 cells. Further, cell proliferation in androgen-dependent cell lines is significantly decreased while proliferation in androgen-independent cell lines is unaffected.

Agents

Disclosed herein are agents that can be used for treating prostate cancer, particularly castration-resistant prostate cancer. The agents may inhibit AR nuclear localization and/or reduce AR levels in castration-resistant prostate cancer.

In one embodiment, the agent is a compound, or a pharmaceutically acceptable salt or ester thereof, having a formula I of:

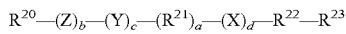

$$R^{20}-(Z)_b-(Y)_c-(R^{21})_a-(X)_d-R^{22}-R^{23}$$

wherein $R^{20}$ is an aryl, substituted aryl, heteroaryl, substituted heteroaryl, heterocycloalkyl, substituted heterocycloalkyl, alkoxy, aryloxy, a thio-containing group, a seleno-containing group, halide, or a nitro-containing group;

Z is alkanediyl, substituted alkanediyl, cycloalkanediyl, or substituted cycloalkanediyl;

Y is S, O, S(=O), —S(=O)(=O)—, or $NR^{10}$, wherein $R^{10}$ is H or alkyl (preferably methyl);

$R^{21}$ is alkanediyl, substituted alkanediyl, cycloalkanediyl, substituted cycloalkanediyl, alkadienyl, substituted alkadienyl, alkatrienyl, or substituted alkatrienyl;

X is —C(=O)—, —S(=O)(=O)—, or —N(H)C(=O)—;

$R^{22}$ is a moiety that includes at least one divalent amino radical;

$R^{23}$ is an aryl, substituted aryl, heteroaryl, substituted heteroaryl, heterocycloalkyl, substituted heterocycloalkyl, alkoxy, aryloxy, amino, a thio-containing group, or a seleno-containing group;

a is 0 or 1;
b is 0 or 1;
c is 0 or 1; and
d is 0 or 1.

In some embodiments, if X is —C(=O)— then Y is not S. In certain embodiments, $R^{21}$ is cycloalkanediyl, such as cyclopropanediyl. When $R^{21}$ is cycloalkanediyl, $R^{20}$ may be a phenyl optionally substituted with at least one halogen and/or $R^{23}$ may be a phenyl substituted with at least one halogen and or at least one alkyl.

In certain embodiments, $R^{20}$ is selected from isoxazolyl, substituted isoxazolyl (e.g, dialkyl-substituted such as dimethyl, hydroxy-substituted, hydroxyalkyl-substituted, or a combination thereof), oxazolyl, substituted oxazolyl (e.g, dialkyl-substituted such as dimethyl, hydroxy-substituted, hydroxyalkyl-substituted, or a combination thereof) cyclohexyl, substituted cyclohexyl (e.g., hydroxy-substituted cyclohexyl), piperidinyl, substituted piperidinyl (e.g., hydroxy-substituted piperidinyl), oxacyclopentyl, substituted oxacyclopentyl (e.g., hydroxyalkyl-substituted), oxacyclohexanyl, substituted oxacyclopentyl (e.g., hydroxyalkyl-substituted), thiophenyl, substituted thiophenyl (e.g., hydroxyalkyl-substituted), phenyl, substituted phenyl (e.g., hydroxyalkyl-substituted or halogen-substituted), pyridinyl, substituted pyridinyl (e.g., hydroxyalkyl-substituted), indolyl, substituted indolyl (e.g., hydroxyalkyl-substituted), furanyl, substituted furanyl (e.g., hydroxyalkyl-substituted), imidazolyl, substituted imidazolyl (e.g., hydroxyalkyl-substituted). In preferred embodiments, $R^{20}$ is substituted isoxazolyl, particularly dialkyl (e.g., dimethyl)-substituted isooxazolyl, phenyl, or substituted phenyl, particularly halogen-substituted phenyl (e.g., fluorophenyl).

In certain embodiments, $R^{21}$ is selected from $C_1$-$C_3$ alkanediyl or substituted $C_1$-$C_3$ alkanediyl (e.g., alkyl-substituted such as methyl or dimethyl), preferably $C_1$ alkanediyl (—$CH_2$—), $C_3$ alkanediyl (—$(CH_2)_3$—), or cycloalkanediyl, preferably cyclopropanediyl. In certain embodiments, $R^{21}$ is:

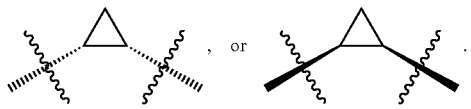

In certain embodiments, $R^{22}$ is selected from:

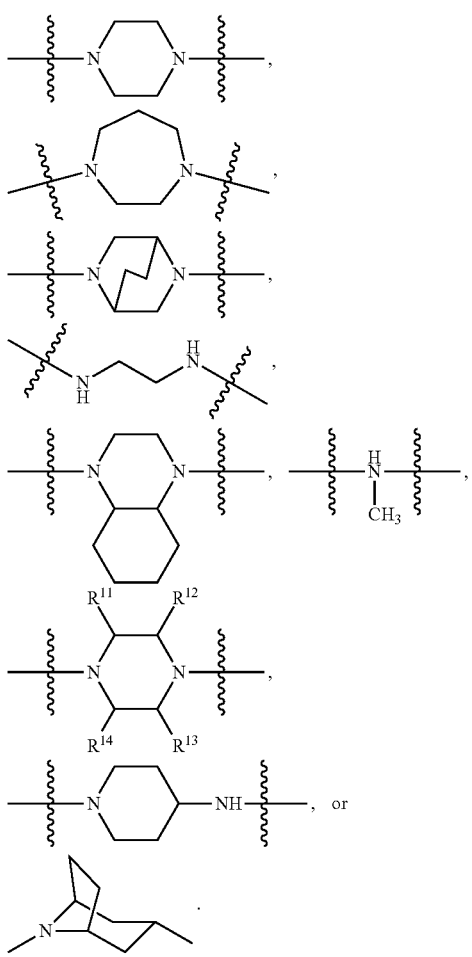

wherein $R^{11}$ to $R^{14}$ are each individually H or alkyl, provided that at least one of $R^{11}$ to $R^{14}$ is alkyl. In certain embodiments, $R^{12}$ and $R^{13}$ are each alkyl (e.g., methyl) and $R^{11}$ and $R^{14}$ are each H. In certain embodiments, $R^{11}$ and $R^{14}$ are each alkyl (e.g., methyl) and $R^{12}$ and $R^{13}$ are each H.

In certain embodiments, $R^{22}$ is a divalent radical of a N-heterocyclic group. Illustrative N-heterocylic groups include piperazinyl, substituted piperazinyl, azabicyclo (for example, azabicyclooctane), and substituted azabicyclo.

In certain embodiments, $R^{23}$ is selected from phenyl, substituted phenyl (e.g., alkyl-substituted phenyl such as dimethyl-substituted, or halogen substituted, such as chloro- or fluoro-substituted, or amino-substituted, or aminoalkyl-substituted; alkynyl-substituted phenyl), piperidinyl, substituted piperidinyl (e.g., amino-substituted), furanyl, substituted furanyl (e.g., aminoalkyl-substituted or amino-substituted), pyridinyl, substituted pyridinyl (e.g., aminoalkyl-substituted or amino-substituted), pyrimidinyl, substituted pyrimidinyl (e.g., aminoalkyl-substituted or amino-substituted), naphthenyl, substituted naphthenyl, (e.g., aminoalkyl-substituted or amino-substituted), thiazole, substituted thiazole (e.g., aminoalkyl-substituted or amino-substituted); isoindazolyl, substituted isoindazolyl (e.g., aminoalkyl-substituted or amino-substituted); triazolyl, or substituted triazolyl (e.g., aminoalkyl-substituted or amino-substituted). $R^{23}$ may have two or more substituents, such as an alkyl substituent and a halogen substituent. Preferably, $R^{23}$ is a substituted phenyl having a structure of:

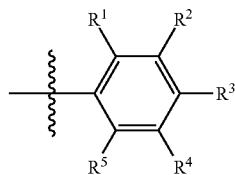

wherein each of $R^1$-$R^5$ is individually H, alkyl, substituted alkyl, alkynyl, substituted alkynyl, halogen, or cyano, provided that at least one of $R^1$-$R^5$ is not H. In certain embodiments, at least one of $R^1$-$R^5$ is alkyl (such as methyl), halogen or cyano. In certain embodiments, $R^1$ is alkyl, halogen or cyano. In certain embodiments, $R^1$ is alkyl and $R^4$ is halogen. In certain embodiments, at least one of $R^1$-$R^5$ is hydroxy-substituted alkynyl.

In certain embodiments, Z is selected from $C_1$-$C_3$ alkanediyl, preferably —$CH_2$—.

In certain embodiments, $R^{20}$ is phenyl or substituted isoxazolyl, b is 0; c is 1; a is 1; $R^{21}$ is —$CH_2$—, Y is S; X is —S(=O)(=O)—, $R^{22}$ is:

and $R^{23}$ is substituted phenyl.

In certain embodiments, $R^{20}$ is substituted phenyl, b is 0, c is 0, $R^{21}$ is cyclopropanediyl, a is 1, X is —C(=O)—, d is 1, $R^{22}$ is

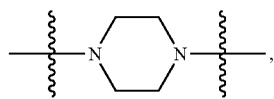

and $R^{23}$ is substituted phenyl. In one such embodiment, $R^{20}$ is halophenyl and $R^{23}$ is halo- and alkyl-substituted phenyl.

In certain embodiments, $R^{21}$ is —$CH_2$—, Y is S; and X is —S(=O)(=O)—.

In certain embodiments, R²² is:

[structure: piperazine diyl]

In certain embodiments, Y is S, O, S(=O), —S(=O)(=O)—; and X is —C(=O)—.

In certain embodiments, b is 0; c is 0; a is 1; and X is —C(=O)—.

In certain embodiments, b is 0; c is 0; a is 1; X is —C(=O)—; and R²¹ is alkanediyl (particularly —CH₂CH₂—),

[structures: two cyclopropane-diyl groups with different stereochemistry], or

In certain embodiments, b is 0; c is 0; a is 1; X is —C(=O)—; R²¹ is alkanediyl (particularly —CH₂CH₂—),

[structures: two cyclopropane-diyl groups], or ;

and R²² is

[structure: piperazine diyl].

In certain embodiments, b is 0; c is 0; a is 1; X is —C(=O)—; R²¹ is alkanediyl (particularly —CH₂CH₂—),

[structures: two cyclopropane-diyl groups], or ;

R²² is

[structure: piperazine diyl];

R²⁰ is phenyl, substituted phenyl, or substituted isoxazolyl; and R²³ is substituted phenyl.

In a further embodiment, the agent is a compound, or a pharmaceutically acceptable salt or ester thereof, having a formula II of:

$$R^{30}-(Z')_b-(Y')-(R^{31})_a-R^{32}-R^{33}$$

wherein R³⁰ is an aryl, substituted aryl, heteroaryl, substituted heteroaryl, heterocycloalkyl, substituted heterocycloalkyl, alkoxy, aryloxy, amino, a thio-containing group, or a seleno-containing group;

Z' is alkanediyl, or substituted alkanediyl;
Y' is S;
R³¹ is alkanediyl or substituted alkanediyl;
X is —C(=O)—;
R³² is a moiety that includes at least one divalent amino radical;
R³³ is a phenyl substituted with at least one halogen or cyano;
a is 0 or 1; and
b is 0 or 1.

In certain embodiments, R³⁰ is selected from isoxazolyl, substituted isoxazolyl (e.g, dialkyl-substituted such as dimethyl, hydroxy-substituted, hydroxyalkyl-substituted, or a combination thereof), oxazolyl, substituted oxazolyl (e.g, dialkyl-substituted such as dimethyl, hydroxy-substituted, hydroxyalkyl-substituted, or a combination thereof) cyclohexyl, substituted cyclohexyl (e.g., hydroxy-substituted cyclohexyl), piperidinyl, substituted piperidinyl (e.g., hydroxy-substituted piperidinyl), oxacyclopentyl, substituted oxacyclopentyl (e.g., hydroxyalkyl-substituted), oxacyclohexanyl, substituted oxacyclopentyl (e.g., hydroxyalkyl-substituted), thiophenyl, substituted thiophenyl (e.g., hydroxyalkyl-substituted), phenyl, substituted phenyl (e.g., hydroxyalkyl-substituted), pyridinyl, substituted pyridinyl (e.g., hydroxyalkyl-substituted), indolyl, substituted indolyl (e.g., hydroxyalkyl-substituted), furanyl, substituted furanyl (e.g., hydroxyalkyl-substituted), imidazolyl, substituted imidazolyl (e.g., hydroxyalkyl-substituted). In preferred embodiments, R³⁰ is substituted isoxazolyl, particularly dialkyl (e.g., dimethyl)-substituted isooxazolyl, or phenyl.

In certain embodiments, Z' is selected from $C_1$-$C_3$ alkanediyl, preferably —CH₂—.

In certain embodiments, R³¹ is selected from $C_1$-$C_3$ alkanediyl or substituted $C_1$-$C_3$ alkanediyl (e.g., alkyl-substituted such as methyl or dimethyl), preferably $C_1$ alkanediyl.

In certain embodiments, R³² is selected from:

[structure: piperazine diyl],

[structure: 1,4-diazepane diyl],

[structure: bridged bicyclic diamine],

[structure: —NH—CH₂CH₂—NH—],

[structure: decahydroquinoxaline diyl], [structure: —N(CH₃)—H—],

[structure: substituted piperazine with R¹¹, R¹², R¹³, R¹⁴], or

-continued

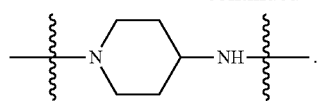

Preferably, R$^{33}$ is a substituted phenyl having a structure of:

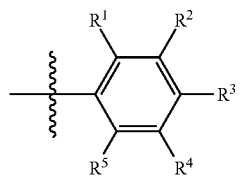

wherein each of R$^1$-R$^5$ is individually H, alkyl, halogen, or cyano, provided that at least one of R$^1$-R$^5$ is halogen or cyano. In certain embodiments, R$^1$ is alkyl, halogen or cyano.

In certain embodiments, R$^{30}$ is substituted isoxazolyl, b is 1; a is 1; R$^{21}$ is —CH$_2$—; and R$^{32}$ is:

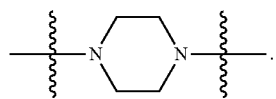

Certain embodiments are described below in the following numbered clauses:

1. A compound, or a pharmaceutically acceptable salt or ester thereof, selected from:

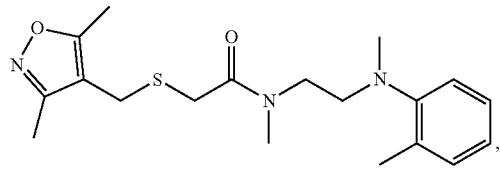

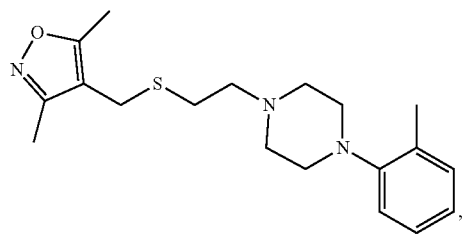

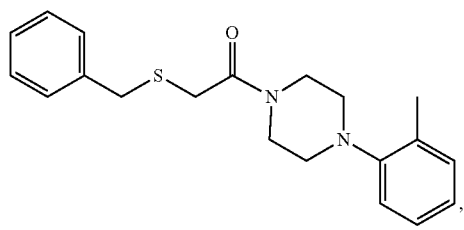

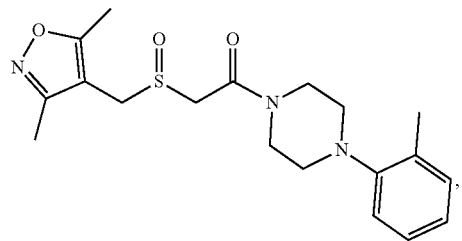

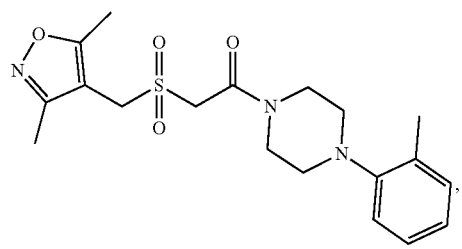

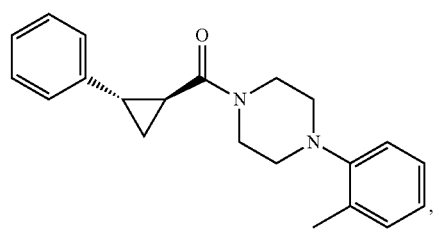

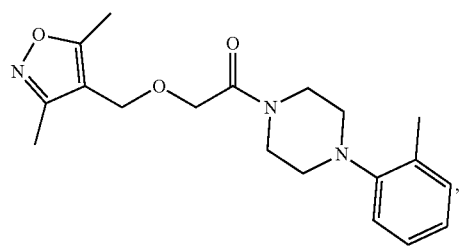

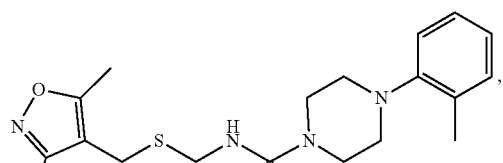

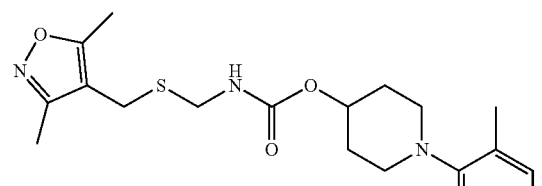

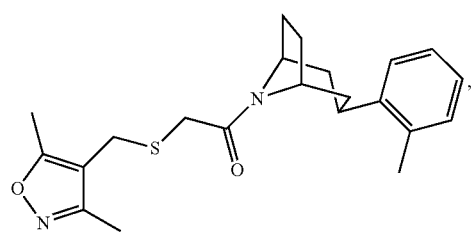

-continued

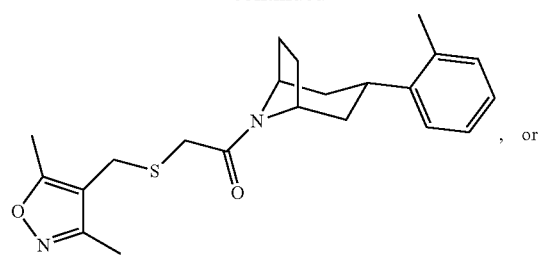, or

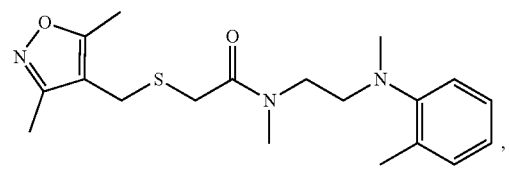

2. The compound of clause 1, wherein the compound is:

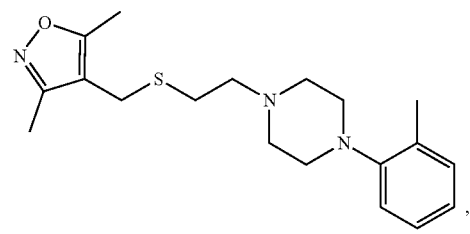,

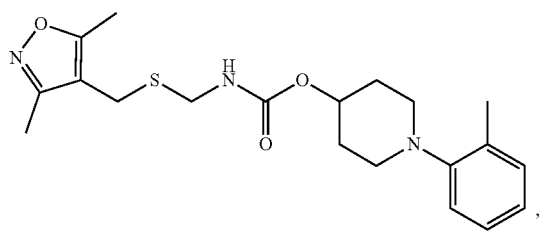,

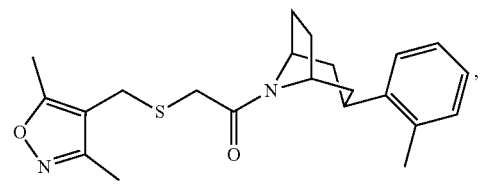,

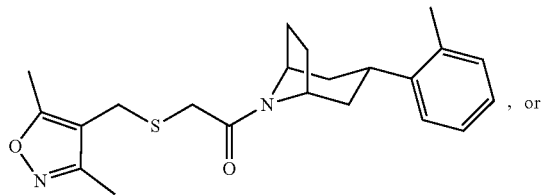, or

-continued

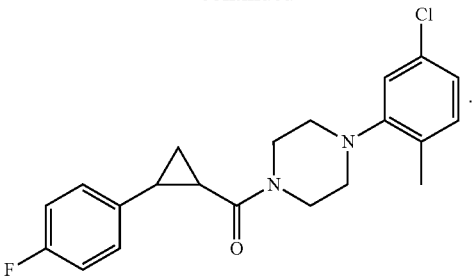

3. The compound of clause 1, wherein the compound is:

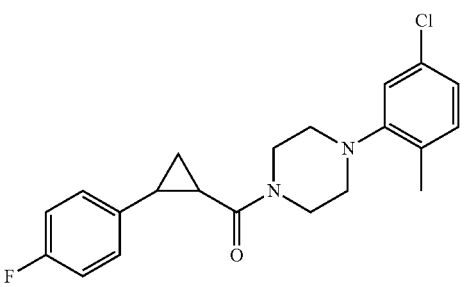

4. The compound of clause 1, wherein the compound is:

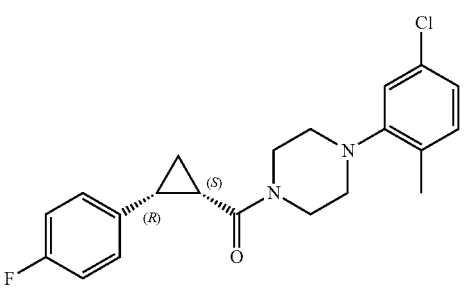

5. A pharmaceutical composition comprising at least one pharmaceutically acceptable additive, and a compound of any one of clauses 1-4.

6. The pharmaceutical composition of clause 5, wherein the compound is:

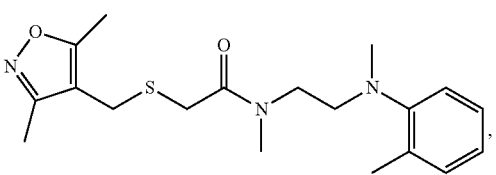,

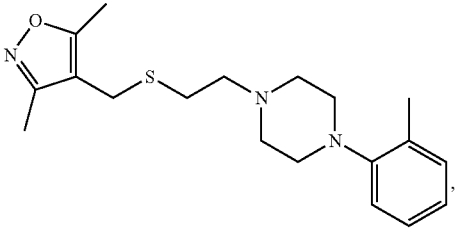,

7. The pharmaceutical composition of clause 5, wherein the compound is:

8. The pharmaceutical composition of clause 5, wherein the compound is:

9. A method for treating prostate cancer in a subject, comprising administering to the subject a therapeutically effective amount of a compound of any one of clauses 1-4.

10. The method of clause 9, wherein the prostate cancer is castration-resistant prostate cancer.

11. The method of clause 9 or clause 10, wherein the compound is orally administered.

12. The method of any one of clauses 9-11, wherein the method is used in combination with androgen deprivation therapy.

13. The method of any one of clauses 9-12, wherein the agent is co-administered with abiraterone.

14. The method of any one of clauses 9-13, wherein the method further comprises identifying a subject that is in need of treatment with the agent.

15. The method of any one of clauses 9-14, wherein the compound is:

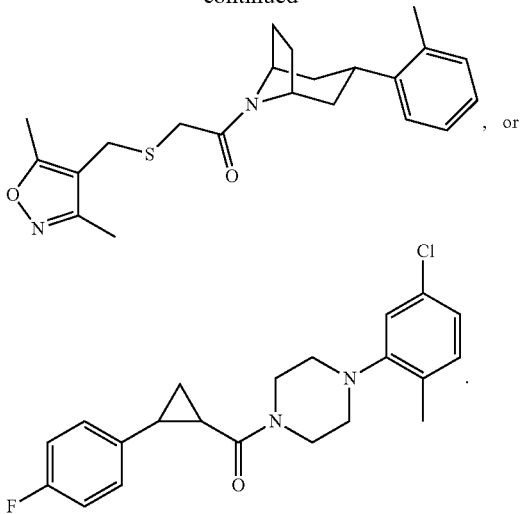

, or

16. The method of any one of clauses 9-14, wherein the compound is:

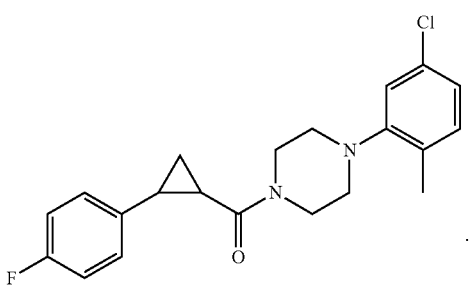 [SMILES: Cc1ccc(Cl)cc1N1CCN(C(=O)C2CC2c2ccc(F)cc2)CC1]

17. The method of any one of clauses 9-14, wherein the compound is:

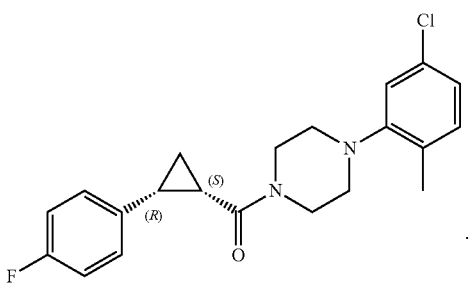

Illustrative compounds are shown in FIGS. 1A-1D.

Figure 3:
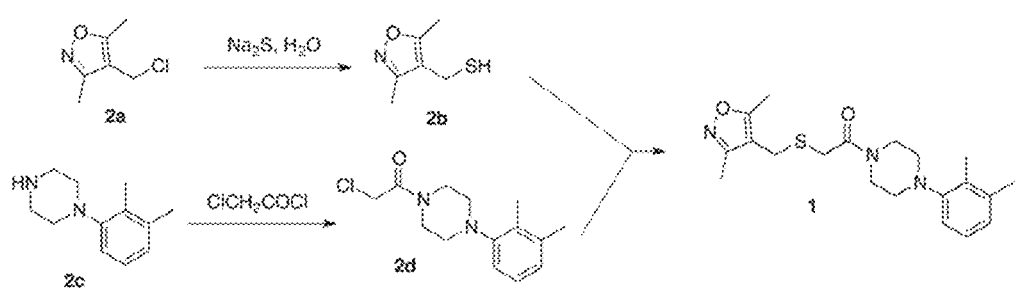
FIG. 3 is a reaction scheme showing the synthesis of 2-((isoxazol-4-ylmethyl)thio)-1-(4-phenylpiperazin-1-yl) ethanone 1.
Figure 4:
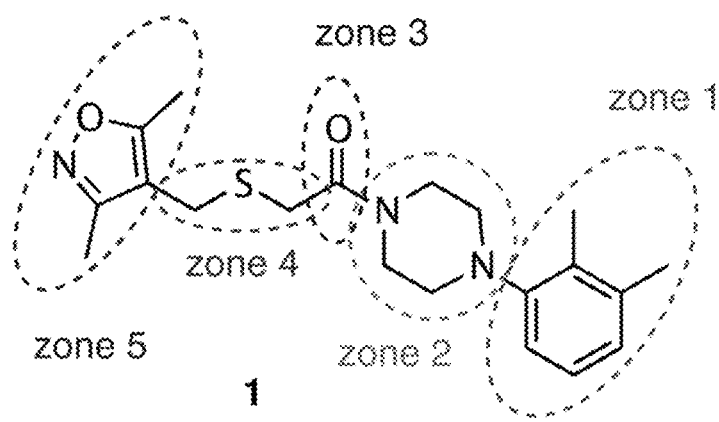
FIG. 4 is a chemical structure of 2-((isoxazol-4-ylmethyl) thio)-1-(4-phenylpiperazin-1-yl)ethanone showing zones of modification.

FIG. 3 shows a synthesis of a parent structure that is amenable to the modifications lined out in a zone model. Isoxazole 2a can be obtained from the chloromethylation of 3,5-dimethylisoxazole, or via the corresponding alcohol, and can be converted to thiol 2b. In situ alkylation of 2b with chloride 2d under the basic conditions of thiolate formation leads to 1. There are many methods known for pyridazine synthesis, and the preparation of 2c can follow one of these methods, for example starting with the aniline Acylation of 2c with chloroacetyl chloride provides 2d. FIG. 4 shows zones of modification for compound 1. The building blocks for zones 1 and 4 have been selected to cover a large range of chemical diversity; in addition, they are commercially available and are therefore readily funneled into the segment-based synthesis plan. Zone 2 contains a few diamines that preserve the distance between zone 1 and zone 3, i.e. where the nitrogens are appropriately spaced, but this zone can also be contracted to a simple nitrogen linker in order to probe the need to maintain the overall distance and orientation between zone 1 and zone 4. Zone 3 contains another spacer functionality, but the amide carbonyl group might also be involved in specific interactions with the binding site on the protein. Therefore, the distance between the carboxyl function and the halide electrophile can be varied, and the carbonyl group can also be replaced by a sulfonyl function.

Figure 5:
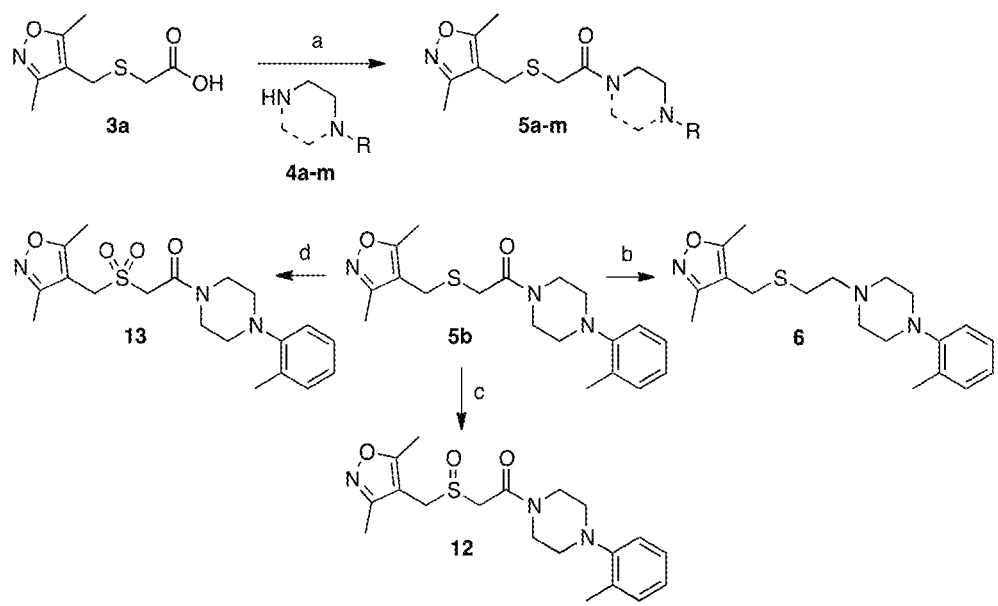
FIG. 5 is a reaction scheme showing synthesis of certain embodiments of the disclosed compounds. Reagents and conditions: (a) T3P (propylphosphonic anhydride), $Et_3N$ (triethylamine), $CH_2Cl_2$, rt (room temperature), overnight, 52-98%; (b) $LiAlH_4$, dry THF (tetrahydrofuran), 0° C., 1 h, 42%; (c) $NaIO_4$, MeOH (methanol), $H_2O$, rt, 15 h, 68%; (d) m-CPBA (meta-chloroperoxybenzoic acid), $CH_2Cl_2$, rt, 15 h, 44%.

As described below, compounds 5a-h were synthesized directly from commercially available carboxylic acids 3a and N-arylated piperazines 4a-h under amide coupling conditions with T3P (Scheme 2 (FIG. 5) and Table 1) (Basavaprabhhu et al., *Synthesis* 2013, 45, 1569-1601). The diamine linker in zone 2 was examined in more detail through the synthesis of analogs 5i-5m. For these target molecules, the requisite diamines 4i-m were prepared by a Buchwald-Hartwig cross-coupling of mono Boc-protected diamines with bromoarenes (Cabello-Sanchez et al., *J. Org. Chem.* 2007, 72, 2030-2039; Larsen et al., *Tetrahedron* 2008, 64, 2938-2950). Reduction of amide 5b with lithium aluminum hydride led to diamine 6. For an initial set of zone 4 analogs, thioether 5b was also oxidized to sulfoxide 12 and sulfone 13 in good yields with sodium periodate and m-chloroperbenzoate, respectively (Scheme 1, FIG. 5).

Figure 6:
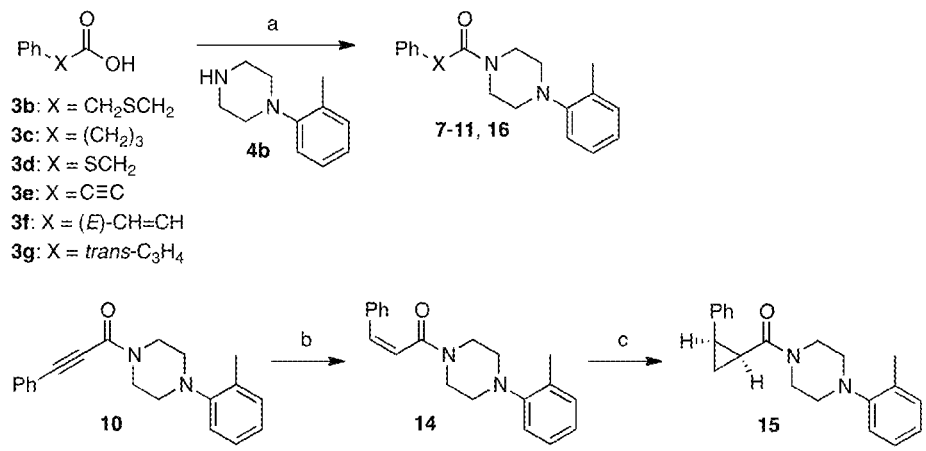
FIG. 6 is a reaction scheme showing synthesis of certain embodiments of the disclosed compounds. Reagents and conditions: (a) T3P, $Et_3N$, $CH_2Cl_2$, rt, overnight, 62-96%; (b) Lindlar's catalyst, quinoline, $H_2$, EtOAc (ethyl acetate), quant.; (c) $CrCl_2$, $CH_2ICl$, THF, reflux, overnight, 57%.

Additional zone 4 and zone 5 analogs with a phenyl group in place of the isoxazole ring were obtained from carboxylic acids 3b-3g (Scheme 2 (FIG. 6) and Table 1). Coupling to piperazine 4b provided amides 7-11 and 16 in high yields. Alkynyl amide 10 was further hydrogenated to cis-alkene 14 using a Lindlar catalyst. The cis-cyclopropane 15 was prepared by a Simmons-Smith cyclopropanation of cis-alkene 14 (Concellón et al., *Org. Lett.* 2007, 9, 2981-2984), whereas the trans-cyclopropane 16 was obtained by coupling of commercially available trans-2-phenylcyclopropanecarboxylic acid 3g with piperazine 4b.

Figure 7:
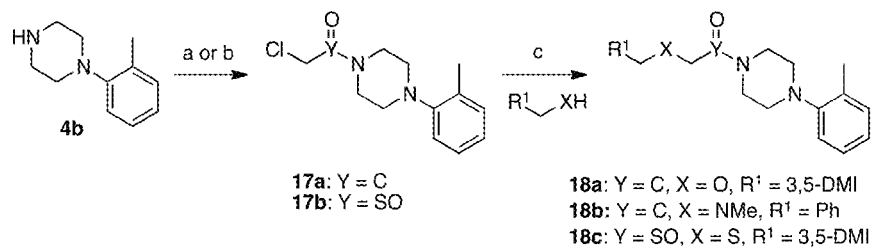
FIG. 7 is a reaction scheme showing synthesis of certain embodiments of the disclosed compounds. Reagents and conditions: (a) 2-chloroacetyl chloride, $Et_3N$, $CH_2Cl_2$, rt, overnight, 99%; (b) chloromethanesulfonyl chloride, $Et_3N$, $CH_2Cl_2$, rt, overnight, 85%; (c) NaH, THF, rt, 1-2 d, 4-99%; (d) DPPA (diphenyl phosphoryl azide), $Et_3N$, toluene, reflux, overnight, 17-65%.
Figure 7:
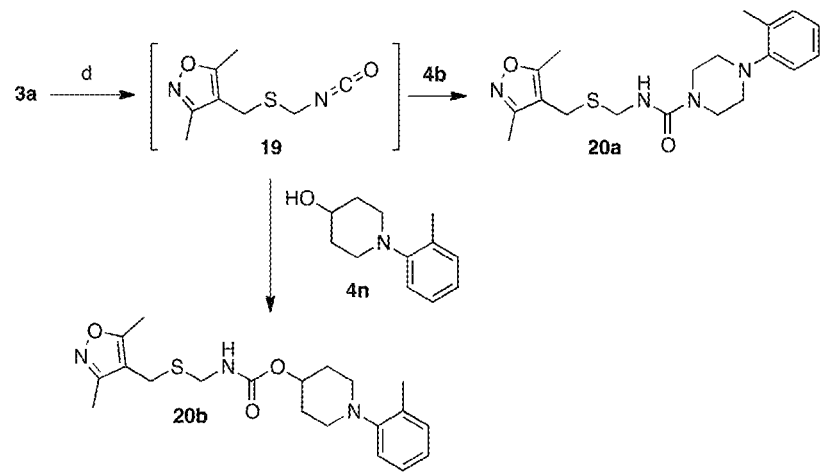

Further modifications in zones 3-4 were accomplished by acylation of piperazine 4b with either 2-chloroacetyl chloride or chloromethanesulfonyl chloride to form the corresponding amide 17a or sulfonamide 17b in good yields (Scheme 3 (FIG. 7) and Table 1). $S_N2$-reaction of 17a and 17b led to ether 18a, amine 18b, and thioether 18c. Starting with carboxylic acid 3a, urea 20a and carbamate 20b were obtained in moderate yields via a Curtius rearrangement and addition of the intermediate isocyanate 19 to amine 4b and alcohol 4n, respectively (Scheme 4, FIG. 7) (WO 2005/085275).

Figure 8:
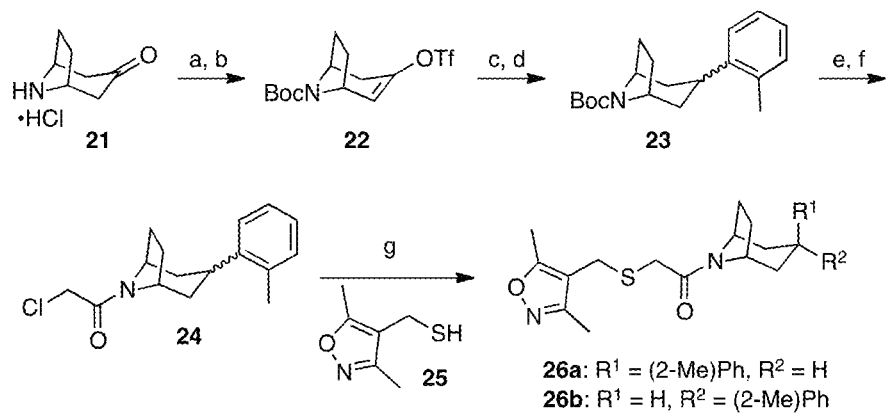
FIG. 8 is a reaction scheme showing synthesis of certain embodiments of the disclosed compounds. Reagents and conditions: (a) $Boc_2O$, DMAP, $CH_2Cl_2$, rt, overnight, 78%; (b) NaHMDS (sodium bis(trimethylsilyl)amide), $PhNTf_2$ (N-phenyl-bis(tifluoromethanesulfonamide), THF, −78° C. to rt, 4 h, 78%; (c) $Pd(PPh_3)_4$, LiCl, $Na_2CO_3$, (2-Me)PhB $(OH)_2$, DME (dimethoxyethane), $H_2O$, 60° C., 3 h, 78%; (d) $H_2$, Pd/C, EtOH (ethanol), rt, 14 h, 90%; (e) TFA (trifluoroacetic acid), $CH_2Cl_2$, rt, 16 h, quant.; (f) 2-chloroacetyl chloride, $Et_3N$, THF, rt, 22 h, 79%; (g) 25, NaH, THF, rt, 1 d, 30%.

A bridged bicyclic ring was introduced to add a strong conformational constraint in zone 2 (Scheme 5 (FIG. 8) and Table 1). Boc-protection of nortropinone hydrochloride 21 followed by enolization with NaHMDS and trapping of the enolate with N-phenyltriflimide provided vinyl triflate 22 in good yield. A Suzuki coupling was used to install the o-tolyl group, and the styrene double bond was reduced with Pd/C to afford 23 as a mixture of diastereomers. Without separation, this mixture was deprotected and acylated with α-chloroacetyl chloride. Finally, the chloride was displaced using thiol 25 and sodium hydride to afford the thioether. Diastereomers 26a and 26b were separated by chromatography on $SiO_2$ to afford both analogs in modest yields.

TABLE 1

Structures of amine building blocks 4 and analogs 5, 7-11, and 16.

| Analog | Amine 4 | R | X |
|---|---|---|---|
| 5a | 4a | Ph | — |
| 5b | 4b | (2-Me)Ph | — |
| 5c | 4c | (3-Me)Ph | — |
| 5d | 4d | (4-Me)Ph | — |
| 5e | 4e | (2-NC)Ph | — |
| 5f | 4f | (2-F)Ph | — |
| 5g | 4g | 1-Naphthyl | — |
| 5h | 4h | (2-MeO)Ph | — |
| 5i | 4i | (2-Me)Ph | — |
| 5j | 4j | (2-Me)Ph | — |
| 5k | 4k | (2-Me)Ph | — |
| 5l | 4l | Ph | — |
| 5m | 4m | (3-Me)Ph | — |
| 7 | 4b | (2-Me)Ph | $CH_2SCH_2$ |
| 8 | 4b | (2-Me)Ph | $(CH_2)_3$ |
| 9 | 4b | (2-Me)Ph | $SCH_2$ |
| 10 | 4b | (2-Me)Ph | C≡C |
| 11 | 4b | (2-Me)Ph | (E)-HC=CH |
| 16 | 4b | (2-Me)Ph | (E)-c-$C_3H_4$ |

Pharmaceutical Compositions and Method of Use

The agents disclosed herein may be administered to a subject for treating prostate cancer, particularly castration-resistant prostate cancer. In certain embodiments a subject is identified as having castration-resistant prostate cancer that may be responsive to the agents disclosed herein. For example, patients that are offered any form of androgen deprivation therapy or anti-androgen therapy, including treatment with abiraterone or MDV3100, for the management of prostate cancer would be candidates for treatment with the agents disclosed herein.

Administration of the agent may reduce the nuclear level of androgen receptor in castration-resistant prostate cancer (CRPC) cells relative to the untreated control CRPC cells. Reducing nuclear androgen receptor levels is expected to inhibit its activation. Reduction of androgen receptor activation can be determined via measuring androgen-responsive genes, such as prostate-specific antigen (PSA).

In certain embodiments, the agent may be co-administered with another therapeutic agent such as, for example, an immunostimulant, an anti-cancer agent, an antibiotic, or a combination thereof. In particular, the agents targeting AR nuclear localization could be used in combination with standard androgen deprivation therapy (ADT) or with abiraterone in the treatment of CRPC. In one embodiment, the agent is co-administered with MDV3100 (enzalutamide), which may produce synergistic results since MDV3100 targets the ligand binding domain whereas the agent targets other domain(s) of the androgen receptor.

The agents disclosed herein can be included in a pharmaceutical composition for administration to a subject. The pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The agents disclosed herein can be administered to subjects by a variety of mucosal administration modes, including by oral, rectal, intranasal, intrapulmonary, or transdermal delivery, or by topical delivery to other surfaces. Optionally, the agents can be administered by non-mucosal routes, including by intramuscular, subcutaneous, intravenous, intra-arterial, intra-articular, intraperitoneal, intrathecal, intracerebroventricular, or parenteral routes. In other alternative embodiments, the agents can be administered ex vivo by direct exposure to cells, tissues or organs originating from a subject.

To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The agents can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The agents can be combined with the base or vehicle according to a variety of methods, and release of the agents can be by diffusion, disintegration of the vehicle, or associated formation of water channels. In some circumstances, the agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-CO-lactic acid), poly(epsilon.-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the agent can be delivered to a subject in a manner consistent with conventional methodologies associated with management of the disorder for which treatment or prevention is sought. In accordance with the disclosure herein, a prophylactically or therapeutically effective amount of the agent is administered to a subject in need of such treatment for a time and under conditions sufficient to prevent, inhibit, and/or ameliorate a selected disease or condition or one or more symptom(s) thereof.

The administration of the agent can be for either prophylactic or therapeutic purpose. When provided prophylactically, the agent is provided in advance of any symptom. The prophylactic administration of the agents serves to prevent or ameliorate any subsequent disease process. When provided therapeutically, the compound is provided at (or shortly after) the onset of a symptom of disease or infection.

For prophylactic and therapeutic purposes, the agent can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the agent can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosage of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent is outweighed in clinical terms by therapeutically beneficial effects. A non-limiting range for a therapeutically effective amount of an agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight. Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

EXAMPLES

1. Biological Materials and Methods

Materials

Phosphate buffered saline (PBS) solution was purchased from Fisher Scientific (MA, USA). Trypsin-EDTA solution, dimethyl sulfoxide (DMSO), Roswell Park Memorial Institute (RPMI) 1640 medium, ethanol (200 proof), puromycin powder, and G418 powder were purchased from Sigma-Aldrich (MO, USA). Fetal bovine Serum (FBS), penicillin-streptomycin solution were purchased from Invitrogen (NY, USA). Dual-Luciferase® Reporter Assay System was purchased from Promega (WI, USA). PSA6.1-luc plasmid was a gift from Dr. Marianne Sadar at the University of British Columbia (BC, CA) and pRL-TK *Renilla* luciferase reporter plasmid was purchased from Promega (WI, USA). The C4-2 castration-resistant prostate cancer cell line was kindly provided by Dr. Leland W. K. Chung (Cedars-Sinai Medical Center).

2. Chemistry

General

Moisture and air-sensitive reactions were performed under $N_2$ or Ar atmosphere and glassware used for these reactions was flamed dried and cooled under $N_2$ or Ar prior to use. THF and $Et_2O$ were distilled from sodium/benzophenone ketyl. DMF and $CH_2Cl_2$ were distilled from $CaH_2$. 1,4-Dioxane was purchased from Acros (Sure/Seal bottle) and used as received. $Et_3N$ was distilled from $CaH_2$ and stored over KOH. Toluene was purified by passage through an activated alumina filtration system. Melting points were determined using a Mel-Temp II instrument and are not corrected. Infrared spectra were determined using a Smiths Detection IdentifyIR FT-IR spectrometer. High-resolution mass spectra were obtained on a Micromass UK Limited, Q-TOF Ultima API, Thermo Scientific Exactive Orbitrap LC-MS. Automated column chromatography was done using an Isco Combiflash Rf. $^1$H and $^{13}$C NMR spectra were obtained on Bruker Advance 300 $MH_2$, 400 MHz, or 500 $MH_2$ instruments. Chemical shifts (δ) were reported in parts per million with the residual solvent peak used as an internal standard, δ $^1H/^{13}C$ (Solvent): 7.26/77.00 ($CDCl_3$); 2.05/29.84 (acetone-d6); 2.50/39.52 (DMSO-d6), 3.31/49.00 (CD3OD); and are tabulated as follows: chemical shift, multiplicity (s=singlet, brs=broad singlet, d=doublet, brd=broad doublet, t=triplet, app t=apparent triplet, q=quartet, m=multiplet), number of protons, and coupling constant(s). $^{13}$C NMR spectra were obtained at 75 $MH_2$, 100 MHz, or 125 $MH_2$ using a proton-decoupled pulse sequence and are tabulated by observed peak. $CDCl_3$ was filtered through dried basic alumina prior to use. Thin-layer chromatography was performed using pre-coated silica gel 60 $F_{254}$ plates (EMD, 250 μm thickness) and visualization was accomplished with a 254 nm UV light and by staining with a PMA solution (5 g of phosphomolybdic acid in 100 mL of 95% EtOH), Vaughn's reagent (4.8 g of $(NH_4)_6Mo_7O_{24}.4H_2O$ and 0.2 g of $Ce(SO_4)_2$ in 100 mL of a 3.5 N $H_2SO_4$ solution) or a $KMnO_4$ solution (1.5 g of $KMnO_4$ and 1.5 g of $K_2CO_3$ in 100 mL of a 0.1% NaOH solution). Chromatography on $SiO_2$ (Silicycle, Silia-P Flash Silica Gel or SiliaFlash® P60, 40-63 μm) was used to purify crude reaction mixtures. Final products were >95% purity as analyzed by RP (reverse phase) HPLC (Alltech Prevail C-18, 100×4.6 mm, 1 mL/min, $CH_3CN$, $H_2O$ and 0.1% TFA) with UV (210, 220 and 254 nm), ELS (nebulizer 45° C., evaporator 45° C., $N_2$ flow 1.25 SLM), and MS detection using a Thermo Scientific Exactive Orbitrap LC-MS (ESI positive). All other materials were obtained from commercial sources and used as received.

Example 1

Synthesis and Characterization

Synthesis of several of the compounds is described in detail below:

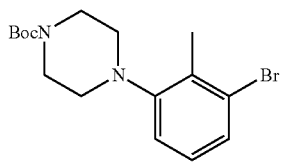

tert-Butyl 4-(3-bromo-2-methylphenyl)piperazine-1-carboxylate (BRE454-64)

A microwave vial under Ar was charged with tert-butyl 1-piperazinecarboxylate (154 mg, 0.825 mmol), NaO-t-Bu (0.0952 g, 0.990 mmol), (rac)-BINAP (0.0393 g, 0.0619 mmol, 7.5 mol %), $Pd_2(dba)_3$ (0.0192 g, 0.0206 mmol), and degassed toluene (2.1 mL). 2-Bromo-6-iodotoluene (121 µL, 0.825 mmol) was added, and the mixture was heated in sealed vial at 80° C. for 19 h, cooled to room temperature, diluted with $CH_2Cl_2$, filtered through Celite, and concentrated in vacuo. The mixture was purified by chromatography on $SiO_2$ (1:9, EtOAc/hexanes) to give the product (0.095 g, 0.27 mmol, 32%) as a yellow oil: $^1$H NMR (500 MHz, $CDCl_3$) δ 7.30 (d, J=8.0 Hz, 1H), 7.02 (t, J=8.0 Hz, 1H), 6.95 (d, J=7.5 Hz, 1H), 3.57 (m, 4H), 2.83 (t, J=4.5 Hz, 4H), 2.40 (s, 3H), 1.49 (s, 9H).

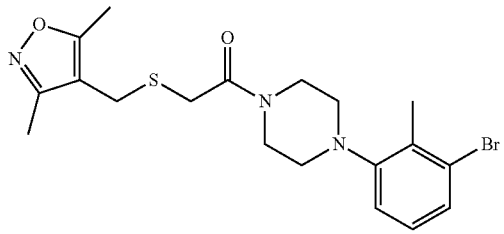 [SMILES: Cc1noc(C)c1CSCC(=O)N1CCN(c2cccc(Br)c2C)CC1]

1-(4-(3-Bromo-2-methylphenyl)piperazin-1-yl)-2-(((3,5-dimethylisoxazol-4-yl)methyl)thio) ethan-1-one (BRE454-75)

A solution of BRE454-64 (0.0770 g, 0.22 mmol) in THF (0.3 mL) at 0° C. was treated with 4 M HCl in dioxane (1.3 mL) and stirred at 0° C. for 2 h. The yellow solid was collected by filtration, washed with $Et_2O$, dried under high vacuum and carried on to the next step without further purification.

To a solution of ([(3,5-dimethylisoxazol-4-yl)methyl]thio)acetic acid (0.0350 g, 0.174 mmol) in $CH_2Cl_2$ (1.7 mL) was added 4-(3-bromo-2-methylphenyl)piperazine hydrochloride and triethylamine (121 µL, 0.870 mmol). The mixture was cooled to 0° C., treated with T3P (50% solution in EtOAc, 184 µL, 0.261 mmol), warmed to room temperature, stirred for 20 h, diluted with $CH_2Cl_2$, and washed with sat. $NH_4Cl$, sat. $NaHCO_3$, and brine. The organic layer was dried ($Na_2SO_4$), filtered, and concentrated in vacuo. The crude material was purified by chromatography on $SiO_2$ (3:2, EtOAc/hexanes, base washed with 0.1% $Et_3N$ prior to use) to give the product (0.0762 g, 0.174 mmol, quant. 100% pure by ELSD) as a colorless oil: IR (ATR) 2921, 2820, 1637, 1587, 1562, 1460, 1428, 1282, 1237, 1195, 1136, 1038, 994, 913, 780, 731, 714 $cm^{-1}$; $^1$H NMR (400 MHz, $CDCl_3$) δ 7.32 (dd, J=0.8, 7.6 Hz, 1H), 7.03 (t, J=8.0 Hz, 1H), 6.94 (dd, J=0.8, 8.0 Hz, 1H), 3.77 (br s, 2H), 3.63 (s, 2H), 3.63-3.57 (m, 2H), 3.23 (s, 2H), 2.90 (t, J=4.4 Hz, 2H), 2.88-2.83 (m, 2H), 2.43 (s, 3H), 2.40 (s, 3H), 2.31 (s, 3H); $^{13}$C-NMR (125 MHz, $CDCl_3$) δ 167.6, 166.8, 159.7, 152.2, 132.9, 128.1, 127.4, 126.6, 118.3, 109.7, 52.1, 51.8, 46.8, 42.2, 32.1, 23.8, 18.2, 11.1, 10.2; HRMS (ESI) m/z calcd for $C_{19}H_{25}N_3O_2BrS$ ([M+H]$^+$) 438.0845, found 438.0831.

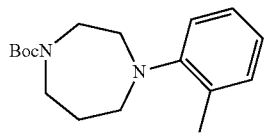 [SMILES: Cc1ccccc1N1CCCN(C(=O)OC(C)(C)C)CC1]

tert-Butyl 4-(o-tolyl)-1,4-diazepane-1-carboxylate (BRE454-66)

A microwave vial under Ar was charged with 1-Boc-homopiperazine (223 mg, 1.10 mmol), NaO-t-Bu (0.116 g, 1.20 mmol), (rac)-BINAP (0.0478 g, 0.0752 mmol, 7.5% mol), $Pd_2(dba)_3$ (0.0233 g, 0.0251 mmol, 2.5% mol in Pd), and degassed toluene (2.8 mL). 2-Bromotoluene (0.175 g, 1.00 mmol) was added, and the mixture was heated in a sealed vial at 80° C. for 19 h, cooled to room temperature diluted with $CH_2Cl_2$, filtered over Celite, and concentrated. The crude material was purified by chromatography on $SiO_2$ (1:9, EtOAc/hexanes) to give the product (0.139 g, 0.479 mmol, 48%) as a yellow oil: IR (ATR) 2973, 2828, 1689, 1598, 1491, 1457, 1411, 1364, 1233, 1215, 1156, 1122, 878, 761, 725 $cm^{-1}$; $^1$H NMR (500 MHz, $CDCl_3$, rt, rotamers) δ 7.16 (d, J=6.0 Hz, 1H), 7.12 (d, J=6.0 Hz, 1H), 7.04 (d, J=7.5 Hz, 1H), 6.95 (t, J=7.0 Hz, 1H), 3.62-3.52 (m, 4H), 3.12-3.04 (m, 4H), 2.31 (s, 3H), 2.00-1.88 (m, 2H), 1.49 (s, 9H); $^{13}$C-NMR (100 MHz, $CDCl_3$, rt, rotamers) 6155.6, 155.5, 153.9, 153.8, 132.9, 130.9, 126.5, 123.1, 120.8 (2C), 79.3, 56.2, 56.0, 55.5, 55.2, 48.4, 48.0, 46.2, 45.4, 29.0, 28.9, 28.5, 18.5; HRMS (ESI) m/z calcd for $C_{17}H_{27}N_2O_2$ ([M+H]$^+$) 291.2067, found 291.2062.

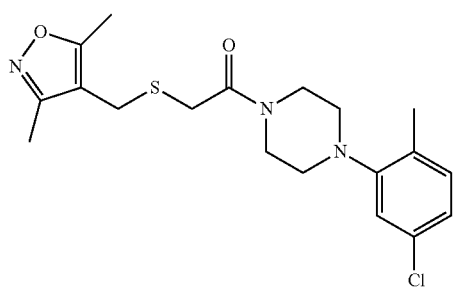 [SMILES: Cc1ccc(Cl)cc1N1CCN(C(=O)CSCc2c(C)noc2C)CC1]

1-(4-(5-Chloro-2-methylphenyl)piperazin-1-yl)-2-4 (3,5-dimethylisoxazol-4-yl)methyl)thio) ethan-1-one (BRE454-58)

To a solution of ([(3,5-dimethylisoxazol-4-yl)methyl]thio)acetic acid (0.0450 g, 0.224 mmol) in $CH_2Cl_2$ (2.2 mL)

was added 1-(5-chloro-2-methylphenyl)piperazine (0.0565 g, 0.268 mmol) and triethylamine (93 μL, 0.671 mmol). The mixture was cooled to 0° C., treated with T3P (50% solution in EtOAc, 237 μL, 0.335 mmol), warmed to room temperature, stirred for 20 h, diluted with $CH_2Cl_2$, and washed with sat. $NH_4Cl$, sat. $NaHCO_3$, and brine. The organic layer was dried ($Na_2SO_4$), filtered, and concentrated in vacuo. The crude material was purified by chromatography on $SiO_2$ (1:1, EtOAc/hexanes, base washed with 0.1% $Et_3N$ prior to use) to give the product (0.0881 g, 0.224 mmol, quant, 99.9% pure by ELSD) as a clear colorless oil: IR (ATR) 2921, 2818, 1635, 1592, 1489, 1438, 1270, 1224, 1195, 1148, 1039, 924, 910, 818, 728 cm$^{-1}$; $^1$H NMR (400 MHz, CDCl$_3$) δ 7.11 (d, J=8.0 Hz, 1H), 6.99 (dd, J=2.0, 8.0 Hz, 1H), 6.94 (d, J=2.4 Hz, 1H), 3.76 (t, J=4.8 Hz, 2H), 3.63 (s, 2H), 3.59 (t, J=4.8 Hz, 2H), 3.23 (s, 2H), 2.91 (t, J=4.8 Hz, 2H), 2.86 (t, J=4.8 Hz, 2H), 2.43 (s, 3H), 2.30 (s, 3H), 2.27 (s, 3H); $^{13}$C NMR (125 MHz, CDCl$_3$) δ 167.6, 166.8, 159.7, 151.7, 132.1, 131.8, 130.9, 123.7, 119.7, 109.7, 51.6, 51.5, 46.8, 42.2, 32.0, 23.7, 17.4, 11.1, 10.2; HRMS (ESI) m/z calcd for $C_{19}H_{25}N_3O_2ClS$ ([M+H]$^+$) 394.1351, found 394.1340.

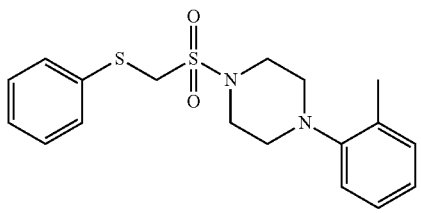 [SMILES: Cc1ccccc1N1CCN(S(=O)(=O)CSc2ccccc2)CC1]

1-(((Phenylthio)methyl)sulfonyl)-4-(o-tolyl)piperazine (BRE454-84)

A solution of 1-(2-methylphenyl)piperazine (0.500 g, 2.75 mmol) and triethylamine (0.39 mL, 2.75 mmol) in $CH_2Cl_2$ (9.8 mL) at 0° C. was treated with chloromethanesulfonyl chloride (0.460 g, 3.03 mmol), gradually warmed to room temperature, and stirred for 14 h. The reaction mixture was quenched with sat. $NH_4Cl$ (3 mL) and extracted with EtOAc (3×20 mL). The combined organic portion was washed with water (2×10 mL) and brine (10 mL), dried ($Na_2SO_4$), filtered, and concentrated. The crude solid was filtered through a plug of $SiO_2$ (pretreated with 0.1% $Et_3N$ in 30% EtOAc/hexanes) and washed thoroughly with 30% EtOAc/hexanes to give the product as an orange solid (0.676 g, 2.34 mmol, 85%): $^1$H NMR (400 MHz, CDCl$_3$) δ 7.21-7.17 (m, 2H), 7.05-7.00 (m, 2H), 4.57 (s, 2H), 3.63 (t, J=4.8 Hz, 4H), 2.98 (t, J=5.2 Hz, 4H), 2.31 (s, 3H).

A solution of this product (0.0400 g, 0.139 mmol), thiophenol (0.0610 g, 0.554 mmol), and $Cs_2CO_3$ (0.0903 g, 0.277 mmol) in DMF (0.28 mL) was stirred at 80° C. for 2 d. The reaction mixture was diluted with brine (10 mL) and extracted with EtOAc (20 mL). The organic layer was separated, washed with brine (2×10 mL), dried ($Na_2SO_4$), and concentrated in vacuo. The crude material was purified by chromatography on $SiO_2$ (1:4, EtOAc/hexanes) the product as a clear colorless oil (0.0257 g, 0.0709 mmol, 51%): IR (ATR) 3054, 2918, 2823, 1598, 1581, 1493, 1440, 1342, 1324, 1262, 1225, 1153, 1112, 1070, 954, 765, 744, 725, 691 cm$^{-1}$; $^1$H NMR (500 MHz, CDCl$_3$) δ 7.59 (d, J=7.5 Hz, 2H), 7.39-7.30 (m, 3H), 7.21-7.14 (m, 2H), 7.02 (t, J=7.5 Hz, 1H), 6.98 (d, J=8.0 Hz, 1H), 4.33 (s, 2H), 3.51 (t, J=4.5 Hz, 4H), 2.92 (t, J=4.5 Hz, 4H), 2.28 (s, 3H); $^{13}$C NMR (100 MHz, CDCl$_3$) δ 150.7, 133.4, 132.7, 131.2, 131.1, 129.4, 128.1, 126.7, 123.9, 119.4, 54.2, 51.8, 46.8, 17.7; HRMS (+ESI) m/z calcd for $C_{18}H_{23}N_2O_2S_2$ ([M+H]$^+$) 363.1195, found 363.1190.

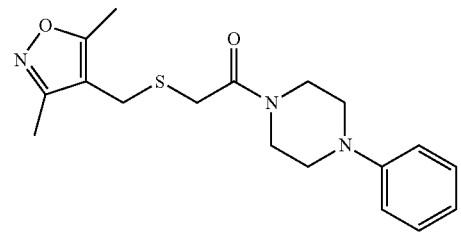 [SMILES: Cc1noc(C)c1CSCC(=O)N1CCN(c2ccccc2)CC1]

2-(((3,5-Dimethylisoxazol-4-yl)methyl)thio)-1-(4-phenylpiperazin-1-yl)ethanone (5a)

To a solution of 2-(((3,5-dimethylisoxazol-4-yl)methyl)thio)acetic acid 3a (0.0200 g, 0.0994 mmol) in $CH_2Cl_2$ (1.25 mL) was added 1-phenylpiperazine 4a (0.0190 g, 0.119 mmol) and $Et_3N$ (41 μL, 0.298 mmol). The reaction mixture was cooled to 0° C., treated with T3P (50 wt. % solution in EtOAc, 105 μL, 0.149 mmol), allowed to warm to room temperature, stirred for 2 d, diluted with $CH_2Cl_2$ and washed with satd. aqueous $NH_4Cl$, satd. aqueous $NaHCO_3$, brine, dried ($Na_2SO_4$), filtered, and concentrated in vacuo. The crude residue was purified by chromatography on $SiO_2$ (ISCO, 12 g column, liquid load in $CH_2Cl_2$, EtOAc/hexanes gradient (10-100%), product eluted at 60%) to give 5a (0.0330 g, 0.0955 mmol, 96%, 100% pure by ELSD) as a colorless solid: Mp 74-75° C.; IR (ATR) 2856, 2802, 1627, 1599, 1496, 1440, 1416, 1229, 1141, 1034, 909, 765, 698 cm$^{-1}$; $^1$H NMR (300 MHz, CDCl$_3$) δ 7.26-7.21 (m, 1H), 6.89-6.83 (m, 3H), 3.72 (app t, 2H, J=5.2 Hz), 3.56 (s, 2H), 3.56-3.54 (m, 2H), 3.18 (s, 2H), 3.15-3.10 (m, 2H), 2.34 (s, 3H), 2.23 (s, 3H); $^{13}$C NMR (75 MHz, CDCl$_3$) δ 166.5, 165.8, 158.6, 149.8, 128.2, 119.6, 115.6, 108.7, 48.5, 48.3, 45.3, 40.7, 31.0, 22.7, 10.0, 9.1; HRMS (ESI) m/z calcd for $C_{18}H_{24}N_3O_2S$ ([M+H]$^+$) 346.1584, found: 346.1571.

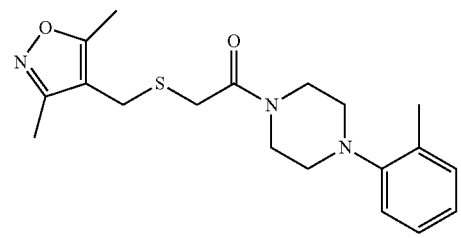 [SMILES: Cc1ccccc1N1CCN(C(=O)CSCc2c(C)noc2C)CC1]

2-(((3,5-Dimethylisoxazol-4-yl)methyl)thio)-1-(4-(o-tolyl)piperazin-1-yl)ethanone (5b)

To a solution of 2-(((3,5-dimethylisoxazol-4-yl)methyl)thio)acetic acid (3a, 0.0200 g, 0.0994 mmol) in $CH_2Cl_2$ (1.25 mL) was added 1-(o-tolyl)piperazine 4b (0.0210 g, 0.119 mmol) and $Et_3N$ (41 μL, 0.298 mmol). The reaction mixture was cooled to 0° C., treated with T3P (50 wt. % solution in EtOAc, 105 μL, 0.149 mmol), allowed to warm to room temperature, stirred for 2 d, diluted with $CH_2Cl_2$ and washed with satd. aqueous $NH_4Cl$, satd. aqueous $NaHCO_3$, brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%), product eluted at 40%) to give 5b (0.0348 g, 0.0968 mmol, 97%, 100% pure by ELSD) as a colorless solid: Mp 89-91° C.; IR (ATR) 2959, 2828, 1631, 1492, 1430, 1261, 1226, 1138, 1036, 979, 959, 776, 726 cm$^{-1}$; $^1$H NMR (300 MHz, CDCl$_3$) δ 7.18 (dd, 2H, J=9.0, 7.5 Hz), 7.01 (dd, 2H, J=14.1, 9.0 Hz), 3.76 (app t, 2H, J=4.9 Hz), 3.63 (s, 2H), 3.59 (app t, 2H, J=4.9 Hz), 3.24 (s, 2H), 2.93 (app t, 2H, J=4.9 Hz), 2.88 (app t, 2H, J=4.9 Hz), 2.43 (s, 3H), 2.32 (s, 3H), 2.30 (s, 3H); $^{13}$C NMR (75 MHz, CDCl$_3$) δ 166.5, 165.8, 158.7, 149.6, 131.7, 130.2, 125.7, 122.8, 118.1, 108.7, 50.8, 50.6, 46.0, 41.3, 31.1, 22.7, 16.7, 10.0, 9.1; HRMS (ESI) m/z calcd for C$_{19}$H$_{26}$N$_3$O$_2$S ([M+H]$^+$) 360.1740, found 360.1725.

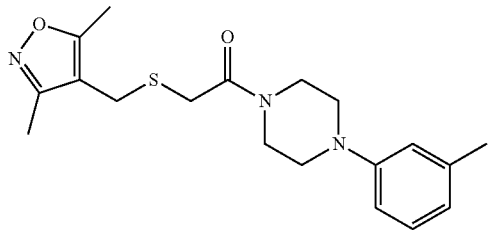 [SMILES: Cc1cccc(N2CCN(C(=O)CSCc3c(C)noc3C)CC2)c1]

2-(((3,5-Dimethylisoxazol-4-yl)methyl)thio)-1-(4-(m-tolyl)piperazin-1-yl)ethanone (5c)

A solution of 2-(((3,5-dimethylisoxazol-4-yl)methyl)thio) acetic acid (3a, 0.0200 g, 0.0994 mmol) in CH$_2$Cl$_2$ (1.25 mL) was added 1-(m-tolyl)piperazine (4c, 21 µL, 0.119 mmol), Et$_3$N (41 µL, 0.298 mmol). The reaction mixture was cooled to 0° C., treated with T3P (50 wt. % solution in EtOAc, 105 µL, 0.149 mmol), allowed to warm to room temperature, stirred for 2 d, diluted with CH$_2$Cl$_2$ and washed with satd. aqueous NH$_4$Cl, satd. aqueous NaHCO$_3$, brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%), eluted at 60%) to give 5c (0.0343 g, 0.954 mmol, 96%, 99.5% pure by ELSD) as a yellow oil: IR (ATR) 2918, 2819, 1635, 1600, 1493, 1424, 1244, 1192, 1145, 995, 957, 775, 729, 694 cm$^{-1}$; $^1$H NMR (300 MHz, CDCl$_3$) δ 7.17 (app t, 1H, J=7.8 Hz), 6.75-6.72 (m, 3H), 3.76 (app t, 2H, J=5.2 Hz), 3.61 (s, 2H), 3.60-3.58 (m, 2H), 3.23 (s, 2H), 3.17 (ddd, 4H, J=5.5, 5.2, 5.0 Hz), 2.41 (s, 3H), 2.32 (s, 3H), 2.28 (s, 3H); $^{13}$C NMR (75 MHz, CDCl$_3$) δ 166.5, 165.8, 158.6, 149.8, 138.0, 128.1, 120.5, 116.5, 112.8, 108.7, 48.6, 48.5, 45.3, 40.8, 31.0, 22.7, 20.7, 10.0, 9.1; HRMS (ESI) m/z calcd for C$_{19}$H$_{26}$N$_3$O$_2$S ([M+H]$^+$) 360.1740, found: 360.1725.

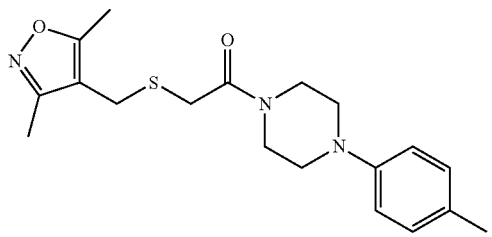 [SMILES: Cc1ccc(N2CCN(C(=O)CSCc3c(C)noc3C)CC2)cc1]

2-(((3,5-Dimethylisoxazol-4-yl)methyl)thio)-1-(4-(p-tolyl)piperazin-1-yl)ethanone (5d)

A solution of 2-(((3,5-dimethylisoxazol-4-yl)methyl)thio) acetic acid (3a, 0.0200 g, 0.0994 mmol) in CH$_2$Cl$_2$ (1.25 mL) was added 1-(p-tolyl)piperazine (4d, 21 µL, 0.119 mmol), Et$_3$N (41 µL, 0.298 mmol). The reaction mixture was cooled to 0° C., treated with T3P (50 wt. % solution in EtOAc, 105 µL, 0.149 mmol), allowed to warm to room temperature, stirred for 2 d, diluted with CH$_2$Cl$_2$, washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient ((10-100%), eluted at 60%) to give 5d (0.0266 g, 0.0740 mmol, 74%, 100% pure by ELSD) as a red solid: Mp 83-85° C.; IR (ATR) 2855, 2801, 1627, 1514, 1440, 1416, 1261, 1230, 1142, 1043, 960, 815, 724 cm$^{-1}$; $^1$H NMR (300 MHz, CDCl$_3$) δ 7.10 (d, 2H, J=8.1 Hz), 6.85 (d, 2H, J=8.1 Hz), 3.77 (app t, 2H, J=4.7 Hz), 3.61-3.58 (m, 4H), 3.23 (s, 2H), 3.13 (ddd, 4H, J=5.6, 5.5, 4.7 Hz), 2.41 (s, 3H), 2.28 (s, 6H); $^{13}$C NMR (75 MHz, CDCl$_3$) δ 167.5, 166.8, 159.7, 148.7, 130.3, 129.8, 117.0, 109.7, 50.1, 49.9, 46.4, 41.8, 32.1, 23.7, 20.4, 11.0, 10.1; HRMS (ESI) m/z calcd for C$_{19}$H$_{26}$N$_3$O$_2$S ([M+H]$^+$) 360.1740, found 360.1725.

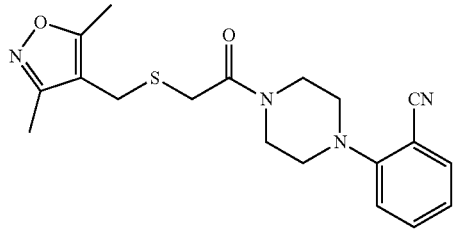 [SMILES: Cc1noc(C)c1CSCC(=O)N1CCN(c2ccccc2C#N)CC1]

2-(4-(2-(((3,5-Dimethylisoxazol-4-yl)methyl)thio) acetyl)piperazin-1-yl)benzonitrile (MK415-62; 5e)

To a solution of ([(3,5-dimethylisoxazol-4-yl)methyl] thio)acetic acid (3a, 0.0280 g, 0.132 mmol) in CH$_2$Cl$_2$ (1.3 mL) was added 2-(piperazin-1-yl)benzonitrile (4e, 0.0253 g, 0.132 mmol) and Et$_3$N (56 µL, 0.400 mmol). The reaction mixture was cooled to 0° C., treated with T3P (50 wt. % solution in EtOAc, 140 µL, 0.200 mmol), allowed to warm to room temperature, stirred for 20 h, diluted with CH$_2$Cl$_2$, washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (95:5, CH$_2$Cl$_2$/MeOH) to give 5e (0.0390 g, 0.105 mmol, 80%, 99.9% pure by ELSD) as a yellow solid: Mp 142-143° C.; IR (neat) 2919, 2216, 1637, 1593, 1420, 1232 cm$^{-1}$; $^1$H NMR (400 MHz, CDCl$_3$) δ 7.61 (dd, 1H, J=7.6, 1.6 Hz), 7.51 (ddd, 1H, J=8.4, 7.6, 1.6 Hz), 7.09 (dt, 1H, J=7.6, 0.9 Hz), 7.02 (d, 1H, J=8.4 Hz), 3.82 (app t, 2H, J=4.8 Hz), 3.67 (app t, 2H, J=4.8 Hz), 3.62 (s, 2H), 3.24 (s, 2H), 3.24-3.21 (m, 2H) 3.15 (app t, 2H, J=5.4 Hz), 2.41 (s, 3H), 2.28 (s, 3H); $^{13}$C NMR (100 MHz, CDCl$_3$) δ 167.6, 166.7, 159.6, 154.9, 134.3, 133.9, 122.7, 118.9, 118.0, 109.7, 106.7, 51.9, 51.1, 46.6, 41.8, 32.1, 23.7, 20.0, 11.0, 10.1; HRMS (ESI) m/z calcd for C$_{19}$H$_{23}$N$_4$O$_2$S ([M+H]$^+$) 371.1542, found 371.1536.

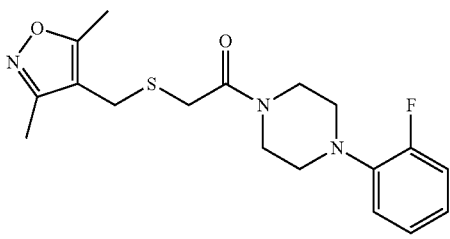 [SMILES: Cc1noc(C)c1CSCC(=O)N1CCN(c2ccccc2F)CC1]

2-(((3,5-Dimethylisoxazol-4-yl)methyl)thio)-1-(4-(2-fluorophenyl)piperazin-1-yl)ethan-1-one (BRE454-54; 5f)

To a solution of 2-(((3,5-dimethylisoxazol-4-yl)methyl)thio)acetic acid (3a, 0.0758 g, 0.377 mmol) in CH$_2$Cl$_2$ (3.8 mL) was added 1-(2-fluorophenyl)-piperazine (4f, 0.0814 g, 0.452 mmol) and Et$_3$N (262 µL, 1.88 mmol). The reaction mixture was cooled to 0° C., treated with T3P (50 wt. % solution in EtOAc, 399 µL, 0.565 mmol), allowed to warm to room temperature, stirred for 20 h, diluted with CH$_2$Cl$_2$, and washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (3:2, EtOAc/hexanes, base washed with 0.1% Et$_3$N prior to use) to give 5f (0.134 g, 0.369 mmol, 98%, 100% pure by ELSD) as a light yellow oil: IR (ATR) 2918, 2827, 1636, 1613, 1500, 1439, 1237, 1195, 1147, 1031, 909, 811, 753, 725 cm$^{-1}$; $^1$H NMR (400 MHz, CDCl$_3$) δ 7.10-6.90 (m, 4H), 3.79 (app t, 2H, J=5.2 Hz), 3.63-3.59 (m, 4H), 3.23 (s, 2H), 3.10 (app t, 2H, J=4.8 Hz), 3.05 (app t, 2H, J=5.2 Hz), 2.28 (s, 3H), 2.42 (s, 3H); $^{13}$C NMR (125 MHz, CDCl$_3$) δ 167.5, 166.8, 159.7, 155.7 (d, $J_{C-F}$=245.0 Hz), 139.4 (d, $J_{C-F}$=8.8 Hz), 124.5 (d, $J_{C-F}$=3.8 Hz), 123.3 (d, $J_{C-F}$=8.8 Hz), 119.2 (d, $J_{C-F}$=2.5 Hz), 116.3 (d, $J_{C-F}$=20.0 Hz), 109.7, 50.7 (d, $J_{C-F}$=2.5 Hz), 50.3 (d, $J_{C-F}$=2.5 Hz), 46.6, 41.9, 32.1, 23.7, 11.1, 10.2; HRMS (ESI) m/z calcd for C$_{18}$H$_{23}$N$_3$O$_2$FS ([M+H]$^+$) 364.1490, found 364.1474.

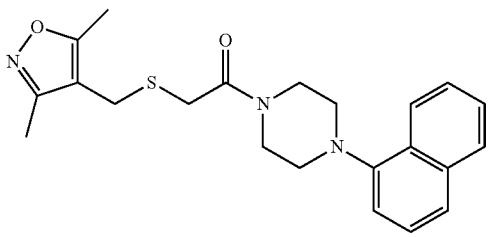 [SMILES: Cc1noc(C)c1CSCC(=O)N1CCN(c2cccc3ccccc23)CC1]

2-(((3,5-Dimethylisoxazol-4-yl)methyl)thio)-1-(4-(naphthalen-1-yl)piperazin-1-yl)ethanone (5g)

A Schlenk flask was charged under N$_2$ with piperazine (0.0500 g, 0.580 mmol), NaO-t-Bu (0.100 g, 1.06 mmol), (rac)-BINAP (0.0051 g, 0.0079 mmol), Pd$_2$(dba)$_3$ (0.0050 g, 0.0053 mmol), and degassed toluene (5 mL). After addition of 1-bromonaphthalene (75 µL, 0.530 mmol), the reaction mixture was heated at 110° C. for 24 h, cooled to room temperature, diluted with CH$_2$Cl$_2$, filtered through Celite, and concentrated in vacuo. The resulting 1-(naphthalen-1-yl)piperazine (4g) was used without further purification for the next reaction. To a solution of (((3,5-dimethylisoxazol-4-yl)methyl)thio)acetic acid (3a, 0.0580 g, 0.272 mmol) in CH$_2$Cl$_2$ (4 mL) was added 1-(naphthalen-1-yl)piperazine 4g (0.0750 g, 0.353 mmol) and Et$_3$N (114 µL, 0.815 mmol). The reaction mixture was cooled to 0° C., treated with T3P (50 wt. % solution in EtOAc, 288 µL, 0.408 mmol), allowed to warm to room temperature, stirred for 20 h, diluted with CH$_2$Cl$_2$, and washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (95:5 CH$_2$Cl$_2$/MeOH) to give 5g (0.0700 g, 0.177 mmol, 65% 2 steps, 99.9% pure by ELSD) as a yellow oil: IR (neat) 2919, 1637, 1435, 1398, 1215, 1192 cm$^{-1}$; $^1$H NMR (500 MHz, CDCl$_3$) δ 8.21 (d, 1H, J=7.5 Hz), 7.85 (d, 1H, J=7.5 Hz), 7.61 (d, 1H, J=8.0 Hz), 7.54-7.49 (m, 2H), 7.42 (d, 1H, J=8.0 Hz), 7.08 (d, 1H, J=7.5 Hz), 3.73-3.66 (m, 4H), 3.64 (s, 2H), 3.28 (s, 2H), 3.27-2.85 (m, 4H), 2.45 (s, 3H), 2.32 (s, 3H); $^{13}$C NMR (125 MHz, CDCl$_3$) δ 167.6, 166.8, 159.7, 148.7, 134.7, 128.7, 128.5, 126.0, 125.7 (2C), 124.2, 123.0, 115.0, 109.7, 52.9, 52.7, 47.0, 42.4, 32.1, 23.7, 11.1, 10.2; HRMS (ESI) m/z calcd for C$_{22}$H$_{26}$N$_3$O$_2$S ([M+H]$^+$) 396.1746, found 396.1740.

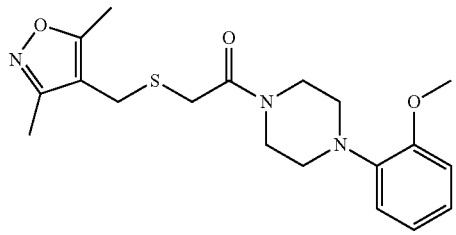 [SMILES: COc1ccccc1N1CCN(C(=O)CSCc2c(C)noc2C)CC1]

2-(((3,5-Dimethylisoxazol-4-yl)methyl)thio)-1-(4-(2-methoxyphenyl)piperazin-1-yl)ethanone (5h)

To a solution of 2-(((3,5-dimethylisoxazol-4-yl)methyl)thio)acetic acid (3a, 0.0200 g, 0.0994 mmol) in CH$_2$Cl$_2$ (1.25 mL) was added 1-(o-methoxyphenyl)piperazine (4h, 0.0230 g, 0.119 mmol) and Et$_3$N (41 µL, 0.298 mmol). The reaction mixture was cooled to 0° C., treated with T3P (50 wt. % solution in EtOAc, 105 µL, 0.149 mmol), warmed to room temperature, stirred for 2 d, diluted with CH$_2$Cl$_2$ and washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%, eluted at 50-70%) to give 5h (0.0195 g, 0.0519 mmol, 52%, 100% pure by ELSD) as a colorless solid: Mp 91-93° C.; IR (ATR) 2997, 2926, 2812, 1626, 1500, 1447, 1243, 1223, 1143, 1023, 979, 751, 741, 726 cm$^{-1}$; $^1$H NMR (300 MHz, CDCl$_3$) δ 7.06-7.01 (m, 1H), 6.95-6.87 (m, 3H), 3.87 (s, 3H), 3.80 (app t, 2H, J=5.0 Hz), 3.64-3.62 (m, 4H), 3.23 (s, 2H), 3.07 (app t, 2H, J=5.0 Hz), 3.03 (app t, 2H, J=5.0 Hz), 2.41 (s, 3H), 2.28 (s, 3H); $^{13}$C NMR (75 MHz, CDCl$_3$) δ 167.4, 166.7, 159.8, 152.2, 140.4, 123.6, 121.0, 118.4, 111.3, 109.7, 55.4, 50.7, 50.5, 46.7, 42.0, 32.1, 23.7, 11.0, 10.1; HRMS (ESI) m/z calcd for C$_{19}$H$_{26}$N$_3$O$_2{3}$S ([M+H]$^+$) 376.1689, found 376.1673.

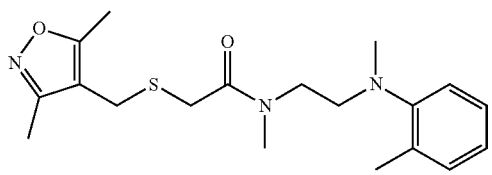 [SMILES: Cc1ccccc1N(C)CCN(C)C(=O)CSCc1c(C)noc1C]

2-(((3,5-Dimethylisoxazol-4-yl)methyl)thio)-N-methyl-N-(2-(methyl(o-tolyl)amino)ethyl) acetamide (5i)

To a solution of 2(((3,5-dimethylisoxazol-4-yl)methyl)thio)acetic acid (3a, 0.0608 g, 0.302 mmol) in CH$_2$Cl$_2$ (3.0 mL) was added N,N'-dimethyl-N-(o-tolyl)ethane-1,2-diamine (4i, 0.0500 g, 0.275 mmol) and Et$_3$N (115 µL, 0.825 mmol). The reaction mixture was cooled to 0° C., treated with T3P (50 wt. % solution in EtOAc, 292 µL, 0.412 mmol), warmed to room temperature, stirred for 20 h, diluted with CH$_2$Cl$_2$, and washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (3:2, EtOAc/hexanes, base washed with 0.1% Et$_3$N prior to use) to give 5i (0.0752 g, 0.207 mmol, 75%, 99.6% pure by ELSD) as a light yellow oil: IR (ATR) 2932, 2795, 1640, 1598, 1493, 1451, 1421, 1393, 1196, 1108, 1047, 766, 738 cm$^{-1}$; $^1$H NMR (400 MHz, CDCl$_3$, room temperature, mixture of rotamers coalescing in DMSO-d$_6$ at 357 K) δ 7.20-7.12 (m, 2H), 7.07-6.95 (m, 2H), 3.59, 3.58 (2s, 2H), 3.54 (t, 1H, J=6.6 Hz), 3.39 (t, 1H, J=6.6 Hz), 3.16-3.08 (m, 3H), 2.97, 2.95 (2s, 4H), 2.71, 2.67 (2s, 3H), 2.38 (s, 3H), 2.30 (s, 2H), 2.27, 2.26 (3s, 4H); $^{13}$C NMR (125 MHz, CDCl$_3$, room temperature, mixture of rotamers coalescing in DMSO-d$_6$ at 357 K) δ 169.2, 168.8, 166.7 (2C), 159.7, 151.7, 150.8, 133.8, 132.9, 131.4, 131.2, 126.7, 126.5, 124.0, 123.2, 120.2, 119.9, 109.8, 53.9, 53.2, 48.4, 46.4, 43.3, 42.3, 36.7, 33.8, 32.4, 31.6, 23.7, 23.4, 18.2, 18.0, 11.0 (2 C), 10.1; HRMS (ESI) m/z calcd for C$_{19}$H$_{28}$N$_3$O$_2$S ([M+H]$^+$) 362.1897, found 362.1890.

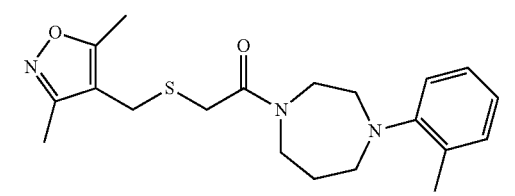 [SMILES: Cc1ccccc1N1CCCN(C(=O)CSCc2c(C)noc2C)CC1]

2-(((3,5-Dimethylisoxazol-4-yl)methyl)thio)-1-(4-(o-tolyl)-1,4-diazepan-1-yl)ethan-1-one (BRE454-76; 5j)

A solution of tert-butyl 4-(o-tolyl)-1,4-diazepane-1-carboxylate (29a, 0.0750 g, 0.258 mmol) in THF (0.3 mL) was cooled to 0° C., treated with 4 M HCl in dioxane (1.6 mL) and stirred at 0° C. for 2 h. The reaction mixture was concentrated in vacuo and the yellow solid 4j was precipitated in Et$_2$O, filtered off from the solution, washed with Et$_2$O, dried under high vacuum, and used without further purification for the next step.

To a solution of 2-(((3,5-dimethylisoxazol-4-yl)methyl)thio)acetic acid (3a, 0.0460 g, 0.229 mmol) in CH$_2$Cl$_2$ (2.3 mL) was added 4-(o-tolyl)-1,4-diazepane hydrochloride (4j, 0.258 mmol) and Et$_3$N (159 µL, 1.14 mmol). The reaction mixture was cooled to 0° C., treated with T3P (50 wt. % solution in EtOAc, 242 µL, 0.343 mmol), warmed to room temperature, stirred for 20 h, diluted with CH$_2$Cl$_2$, and washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (3:2, EtOAc/hexanes, base washed with 0.1% Et$_3$N) to give 5j (0.0854 g, 0.229 mmol, quant. 100% pure by ELSD) as a clear colorless oil: IR (ATR) 2945, 2825, 1634, 1598, 1491, 1447, 1423, 1215, 1194, 1136, 915, 762, 726 cm$^{-1}$; $^1$H NMR (400 MHz, CDCl$_3$, room temperature, mixture of rotamers) δ 7.20 (app d, 1H, J=7.6 Hz), 7.17 (app t, 1H, J=7.6 Hz), 7.05 (app d, 1H, J=7.6 Hz), 7.01 (app dt, 1H, J=7.2, 2.0 Hz), 3.82-3.78 (m, 2H), 3.71-3.65 (m, 4H), 3.24-3.20 (m, 3H), 3.15 (t, 1H, J=5.2 Hz), 3.12-3.07 (m, 2H), 2.46 (app s, 3H), 2.32 (2s, 6H), 2.04 (sept, 2H, J=6.0 Hz); $^{13}$C NMR (125 MHz, CDCl$_3$, room temperature, mixture of rotamers) δ 168.9, 168.8, 166.9, 166.8, 159.8 (2 C), 153.4, 153.3, 132.9 (2 C), 131.1 (2 C), 126.7, 126.6, 123.6, 123.4, 120.8, 120.7, 109.9, 56.4, 55.8, 55.5, 54.9, 50.1, 47.6, 47.2, 44.9, 32.2, 32.0, 29.5, 28.2, 23.7, 18.5 (2 C), 11.1, 10.2 (2 C); HRMS (ESI) m/z calcd for C$_{20}$H$_{28}$N$_3$O$_2$S ([M+H]$^+$) 374.1897, found 374.1883.

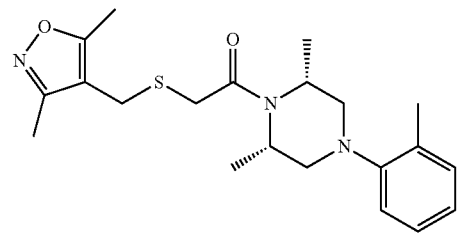 [SMILES: Cc1ccccc1N1C[C@@H](C)N(C(=O)CSCc2c(C)noc2C)[C@@H](C)C1]

1-(2,6-Dimethyl-4-(o-tolyl)piperazin-1-yl)-2-(((3,5-dimethylisoxazol-4-yl)methyl)thio)ethanone (5k)

A solution of (((3,5-dimethylisoxazol-4-yl)methyl)thio) acetic acid (3a, 0.0300 g, 0.142 mmol) in CH$_2$Cl$_2$ (2 mL) was treated with 3,5-dimethyl-1-(o-tolyl)piperazine (4k, 0.0350 g, 0.170 mmol) and Et$_3$N (59 µL, 0.425 mmol). The reaction mixture was cooled to 0° C., treated with T3P (50 wt. % solution in EtOAc, 150 µL, 0.212 mmol), warmed to room temperature, stirred for 20 h, diluted with CH$_2$Cl$_2$, and washed with satd. aqueous NH$_4$Cl, satd. aqueous NaHCO$_3$, and brine, dried (Na$_2$SO$_4$), filtered, and concentrated in vacuo. The crude residue was purified by chromatography on SiO$_2$ (95:5 CH$_2$Cl$_2$/MeOH) to give 5k (0.0450 g, 0.116 mmol, 82%, 99.8% pure by ELSD) as a light yellow oil: IR (neat) 2975, 1629, 1491, 1422, 1327, 1127 cm$^{-1}$; $^1$H NMR (500 MHz, CDCl$_3$) δ 7.22-7.19 (m, 2H), 7.06-7.02 (m, 2H), 4.68 (brs, 1H), 4.05 (brs, 1H), 3.73-3.70 (m, 1H), 3.66-3.61 (m, 1H), 3.30-3.19 (m, 2H), 2.98-2.96 (m, 2H), 2.94-2.89 (m, 1H), 2.81-2.78 (m, 1H), 2.44 (s, 3H), 2.41 (s, 3H), 2.31 (s, 3H), 1.55 (d, 3H, J=6.0 Hz), 1.48 (d, 3H, J=6.0 Hz); $^{13}$C NMR (125 MHz, CDCl$_3$) δ 168.2, 166.7, 151.2, 133.3, 131.2, 126.8, 124.1, 119.6, 109.8, 57.0, 56.8, 49.8, 45.8, 32.0, 23.6, 21.6, 20.3, 18.2, 11.0, 10.1; HRMS (ESI) m/z calcd for C$_{21}$H$_{30}$N$_3$O$_2$S ([M+H]$^+$) 388.2059, found 388.2053.

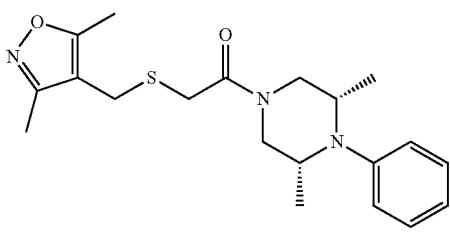 [SMILES: Cc1noc(C)c1CSCC(=O)N1C[C@@H](C)N(c2ccccc2)[C@@H](C)C1]

1-(3,5-Dimethyl-4-phenylpiperazin-1-yl)-2-(((3,5-dimethylisoxazol-4-yl)methyl)thio)ethan-1-one (5l)

A solution of tert-butyl 3,5-dimethyl-4-phenylpiperazine-1-carboxylate (29b, 0.0330 g, 0.114 mmol) in THF (0.1 mL) at 0° C. was treated with 4 M HCl in dioxane (0.70 mL) and stirred at 0° C. for 1.5 h and at room temperature for 1.5 h. The yellow solid was filtered off, washed with Et$_2$O, dried under high vacuum and the resulting crude 4l was directly used for the next step.

To a solution of 2-(((3,5-dimethylisoxazol-4-yl)methyl)thio)acetic acid 3a (0.0229 g, 0.114 mmol) in CH$_2$Cl$_2$ (1.1 mL) was added 2,6-dimethyl-1-phenylpiperazine hydrochloride (4l, 0.0258 g, 0.114 mmol) and Et$_3$N (79 μL, 0.569 mmol). The reaction mixture was cooled to 0° C., treated with T3P (50 wt. % solution in EtOAc, 121 μL, 0.171 mmol), warmed to room temperature, stirred for 20 h, diluted with CH$_2$Cl$_2$, and washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (1:1, acetone/hexanes, base washed with 0.1% Et$_3$N prior to use) to give 5l (0.0322 g, 0.0862 mmol, 76%, 100% pure by ELSD) as a colorless oil: IR (ATR) 2967, 2931, 1639, 1597, 1493, 1449, 1377, 1319, 1272, 1238, 1151, 1091, 886, 771, 731, 703 cm$^{-1}$; $^1$H NMR (400 MHz, CDCl$_3$) δ 7.31 (t, 2H, J=7.6 Hz), 7.18 (t, 1H, J=7.2 Hz), 7.10 (d, 2H, J=7.6 Hz), 4.42 (ddd, 1H, J=12.8, 4.0, 2.4 Hz), 3.70-3.60 (m, 3H), 3.29-3.18 (m, 2H), 3.10-2.93 (m, 3H), 2.67 (dd, 1H, J=13.2, 10.4 Hz), 2.43 (s, 3H), 2.30 (s, 3H), 0.77 (d, 3H, J=6.4 Hz), 0.76 (d, 3H, J=5.6 Hz); $^{13}$C NMR (100 MHz, CDCl$_3$) δ 167.1, 166.8, 159.7, 148.5, 128.9, 126.4, 125.6, 109.8, 56.0, 55.6, 53.4, 48.7, 31.9, 23.7, 18.2, 18.2, 11.1, 10.2; HRMS (ESI) m/z calcd for C$_{20}$H$_{28}$N$_3$O$_2$S ([M+H]$^+$) 374.1897, found 374.1887.

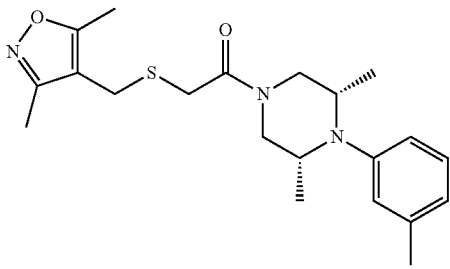 [SMILES: Cc1cccc(N2[C@H](C)CN(C(=O)CSCc3c(C)noc3C)C[C@@H]2C)c1]

1-(3,5-Dimethyl-4-(m-tolyl)piperazin-1-yl)-2-(((3,5-dimethylisoxazol-4-yl)methyl)thio)ethan-1-one (5m)

A solution of tert-butyl 3,5-dimethyl-4-(m-tolyl)piperazine-1-carboxylate (29c, 0.0400 g, 0.131 mmol) in THF (0.1 mL) at 0° C. was treated with 4 M HCl in dioxane (0.80 mL), and stirred at 0° C. for 1.5 h and at room temperature for 1.5 h. A yellow precipitate formed and the solid was filtered off, washed with Et$_2$O, and dried under high vacuum and the resulting crude 4m was used directly for the next step.

To a solution of 2-(((3,5-dimethylisoxazol-4-yl)methyl)thio)acetic acid (3a, 0.0264 g, 0.131 mmol) in CH$_2$Cl$_2$ (1.3 mL) was added 2,6-dimethyl-1-(m-tolyl)piperazine hydrochloride (4m, 0.0316 g, 0.131 mmol) and Et$_3$N (91 μL, 0.656 mmol). The reaction mixture was cooled to 0° C., treated with T3P (50 wt. % solution in EtOAc, 139 μL, 0.197 mmol), warmed to room temperature, stirred for 20 h, diluted with CH$_2$Cl$_2$, washed with satd. aqueous NH$_4$Cl solution, satd. aqueous NaHCO$_3$ solution, and brine, dried (Na$_2$SO$_4$), filtered, and concentrated in vacuo. The crude residue was purified by chromatography on SiO$_2$ (3:2, EtOAc/hexanes, base washed with 0.1% Et$_3$N prior to use) to give 5m (0.0400 g, 0.103 mmol, 79%, 100% pure by ELSD) as a clear colorless oil: IR (ATR) 2966, 2929, 1637, 1602, 1451, 1376, 1319, 1271, 1194, 1149, 1108, 1088, 911, 889, 788, 730, 709 cm$^{-1}$; $^1$H NMR (400 MHz, CDCl$_3$) δ 7.18 (t, 1H, J=7.6 Hz), 6.97 (d, 1H, J=7.6 Hz), 6.90-6.88 (m, 2H), 4.41 (app d, 1H, J=12.8 Hz), 3.64 (brs, 3H), 3.27-3.19 (m, 2H), 3.15-2.91 (m, 3H), 2.67 (t, 1H, J=9.2 Hz), 2.43 (s, 3H), 2.32 (s, 3H), 2.30, (s, 3H), 0.77 (br app s, 6H); $^{13}$C NMR (100 MHz, CDCl$_3$) δ 167.1, 166.8, 159.7, 148.4, 138.7, 128.7, 127.1, 126.4, 123.4, 109.8, 56.0, 55.6, 53.4, 48.7, 32.0, 23.7, 21.4, 18.3, 18.2, 11.1, 10.2; HRMS (ESI) m/z calcd for C$_{21}$H$_{30}$N$_3$O$_2$S ([M+H]$^+$) 388.2053, found 388.2046.

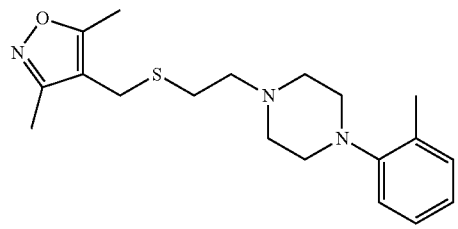 [SMILES: Cc1ccccc1N1CCN(CCSCc2c(C)noc2C)CC1]

3,5-Dimethyl-4-(((2-(4-(o-tolyl)piperazin-1-yl)ethyl)thio)methyl)isoxazole (6)

A solution of 2-(((3,5-dimethylisoxazol-4-yl)methyl)thio)-1-(4-(o-tolyl)piperazin-1-yl)ethanone (5b, 0.0387 g, 0.108 mmol) in THF (1 mL) at 0° C. was treated with LiAlH$_4$ (1 M solution in Et$_2$O, 120 μL, 0.118 mmol), stirred at 0° C. for 1 h, and then quenched with Rochelle's salt (NaKC$_4$H$_4$O$_6$, satd. aqueous solution, 1 mL). The mixture was stirred for an additional 1 h at 0° C., diluted with EtOAc, extracted with EtOAc (2×15 mL), dried (Na$_2$SO$_4$), filtered, and concentrated in vacuo. The crude residue was purified by chromatography on SiO$_2$ (ISCO, 4 g column, liquid load in CH$_2$Cl$_2$, 0-20% MeOH/CH$_2$Cl$_2$, product eluted at 5% MeOH) to give a colorless oil. This oil was further purified by chromatography on SiO$_2$ (CH$_2$Cl$_2$ to 5:95, MeOH/CH$_2$Cl$_2$) on a pipette column to give 6 (0.0155 g, 0.0449 mmol, 42%, 100% pure by ELSD) as a colorless oil: IR (neat) 3393, 2925, 2814, 1637, 1599, 1493, 1448, 1424, 1372, 1227, 1195, 1130, 1041, 1006, 931, 763, 723 cm$^{-1}$; $^1$H NMR (300 MHz, CDCl$_3$) δ 7.16 (app t, 2H, J=7.4 Hz), 7.03-6.95 (m, 2H), 3.75 (t, 1H, J=5.7 Hz), 3.50 (s, 2H), 2.93 (app t, 4H, J=4.5 Hz), 2.63 (brs, 8H), 2.38 (s, 3H), 2.30 (s, 3H), 2.29 (s, 3H); $^{13}$C NMR (75 MHz, CDCl$_3$) δ 165.9, 159.6, 151.4, 132.6, 131.0, 126.6, 123.2, 119.0, 110.5, 77.2, 58.1, 53.6, 51.6, 29.1, 24.0, 23.5, 17.8, 11.1, 10.2; HRMS (ESI) m/z calcd for $C_{19}H_{28}ON_3S$ ([M+H]$^+$) 346.1948, found 346.1946.

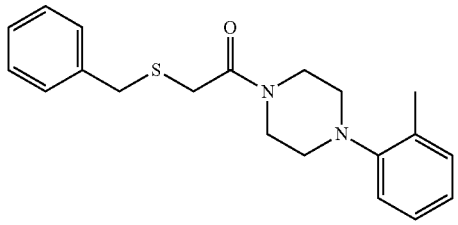 [SMILES: Cc1ccccc1N1CCN(C(=O)CSCc2ccccc2)CC1]

2-(Benzylthio)-1-(4-(o-tolyl)piperazin-1-yl)ethanone (7)

A solution of 2-(benzylthio)acetic acid 3b (0.0440 g, 0.241 mmol) in $CH_2Cl_2$ (3.05 mL) was treated with 1-(o-tolyl)piperazine 4b (0.0521 g, 0.290 mmol) and $Et_3N$ (101 μL, 0.724 mmol). The reaction mixture was cooled to 0° C., treated with T3P (50 wt. % solution in EtOAc, 256 μL, 0.362 mmol), warmed to room temperature and stirred for 2 d. The solution was diluted with $CH_2Cl_2$ and washed with satd. aqueous $NH_4Cl$, satd. aqueous $NaHCO_3$, and brine, dried ($Na_2SO_4$), filtered, and concentrated in vacuo. The crude residue was purified by chromatography on $SiO_2$ (ISCO, 12 g column, liquid load in $CH_2Cl_2$, EtOAc/hexanes gradient (10-100%)) to give 7 (0.0635 g, 0.187 mmol, 77%, 100% pure by ELSD) as a yellow oil: IR (ATR) 2917, 1815, 1634, 1598, 1492, 1437, 1223, 1150, 1031, 975, 761, 700 cm$^{-1}$; $^1$H NMR (300 MHz, CDCl$_3$) δ 7.45-7.23 (m, 7H), 7.06-7.01 (m, 2H), 3.89 (s, 2H), 3.79 (app t, 2H, J=4.9 Hz), 3.59 (app t, 2H, J=4.9 Hz), 3.30 (s, 2H), 2.95-2.90 (m, 4H), 2.37 (s, 3H); $^{13}$C NMR (75 MHz, CDCl$_3$) δ 167.7, 150.9, 137.7, 132.8, 131.2, 129.3, 128.5, 127.2, 126.7, 123.8, 119.3, 51.9, 51.7, 46.9, 42.4, 36.3, 32.4, 17.8; HRMS (ESI) m/z calcd for $C_{20}H_{25}N_2OS$ ([M+H]$^+$) 341.1682, found: 341.1674.

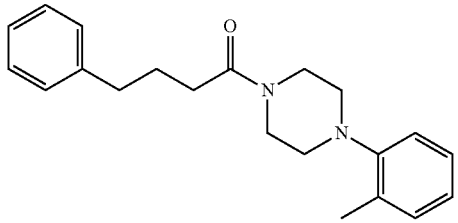 [SMILES: Cc1ccccc1N1CCN(C(=O)CCCc2ccccc2)CC1]

4-Phenyl-1-(4-(o-tolyl)piperazin-1-yl)butan-1-one (8)

To a solution of phenyl butanoic acid (3c, 0.0500 g, 0.305 mmol) in $CH_2Cl_2$ (3.05 mL) was added 1-(o-tolyl)piperazine (4b, 0.0657 g, 0.365 mmol) and $Et_3N$ (85 μL, 0.609 mmol). The reaction mixture was cooled to 0° C., treated with T3P (50 wt. % solution in EtOAc, 322 μL, 0.457 mmol), warmed to room temperature, stirred overnight, diluted with $CH_2Cl_2$ and washed with satd. aqueous $NH_4Cl$, satd. aqueous $NaHCO_3$, and brine, dried ($Na_2SO_4$), filtered, and concentrated in vacuo. The crude residue was purified by chromatography on $SiO_2$ (ISCO, 12 g column, liquid load in $CH_2Cl_2$, EtOAc/hexanes gradient (10-100%), eluted at 30%) to give 8 (0.0863 g, 0.268 mmol, 88%, 100% pure by ELSD) as a colorless oil: IR (ATR) 3024, 2917, 2813, 1641, 1492, 1432, 1223, 1150, 1025, 761, 722 cm$^{-1}$; $^1$H NMR (300 MHz, CDCl$_3$) δ 7.36-7.31 (m, 2H), 7.27-7.18 (m, 5H), 7.07-6.99 (m, 2H), 3.80 (app t, 2H, J=4.8 Hz), 3.55 (app t, 2H, J=4.8 Hz), 2.88 (app t, 4H, J=4.8 Hz), 2.75 (t, 2H, J=7.5 Hz), 2.41 (t, 2H, J=7.5 Hz), 2.36 (s, 3H), 2.06 (ddd, 2H, J=7.9, 7.7, 7.3 Hz); $^{13}$C NMR (75 MHz, CDCl$_3$) δ 171.2, 150.8, 141.6, 132.6, 131.0, 128.4, 128.3, 126.6, 125.8, 123.6, 119.0, 51.9, 51.6, 45.9, 41.9, 35.2, 32.3, 26.6, 17.7; HRMS (ESI) m/z calcd for $C_{21}H_{27}N_2O$ ([M+H]$^+$) 323.2118, found: 323.2110.

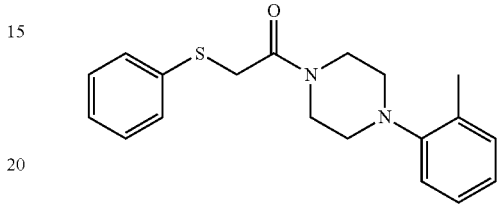

2-(Phenylthio)-1-(4-(o-tolyl)piperazin-1-yl)ethan-1-one (9)

To a solution of 2-(phenylthio)acetic acid (3d, 0.0500 g, 0.297 mmol) in $CH_2Cl_2$ (3.0 mL) was added 1-(o-tolyl)piperazine (4b, 0.0642 g, 0.357 mmol) and $Et_3N$ (83 μL, 0.594 mmol). The mixture was cooled to 0° C., treated with T3P (50 wt. % solution in EtOAc, 315 μL, 0.446 mmol), warmed to room temperature, stirred for 3 d, diluted with $CH_2Cl_2$ and washed with satd. aqueous $NH_4Cl$, satd. aqueous $NaHCO_3$, and brine. The organic layer was dried ($Na_2SO_4$), filtered, and concentrated in vacuo. The crude residue was purified by chromatography on $SiO_2$ (ISCO, 4 g column, liquid load in $CH_2Cl_2$, EtOAc/hexanes gradient (0-30%), eluted at 20-30%) to give 9 (0.0746 g, 0.229 mmol, 77%, 100% pure by ELSD) as a clear colorless oil: IR (ATR) 3057, 2947, 2911, 2856, 2815, 1639, 1598, 1492, 1482, 1382, 1275, 1223, 1203, 1149, 1115, 1032, 974, 950, 909, 762, 738, 723, 690 cm$^{-1}$; $^1$H NMR (400 MHz, CDCl$_3$) δ 7.48 (dd, 2H, J=7.6, 1.2 Hz), 7.34 (app t, 2H, J=7.6 Hz), 7.26-7.17 (m, 3H), 7.02 (app t, 1H, J=7.6 Hz), 6.98 (app d, 1H, J=7.6 Hz), 3.81 (s, 2H), 3.76 (app t, 2H, J=4.8 Hz), 3.63 (app t, 2H, J=4.8 Hz), 2.91 (app t, 2H, J=4.8 Hz), 2.86 (t, 2H, J=4.8 Hz), 2.33 (s, 3H); $^{13}$C NMR (100 MHz, CDCl$_3$) δ 167.1, 150.7, 134.9, 132.7, 131.2, 130.3, 129.1, 127.0, 126.7, 123.8, 119.2, 51.9, 51.6, 47.0, 42.5, 36.7, 17.8; HRMS (ESI) m/z calcd for $C_{19}H_{23}N_2OS$ ([M+H]$^+$) 327.1526, found 327.1514.

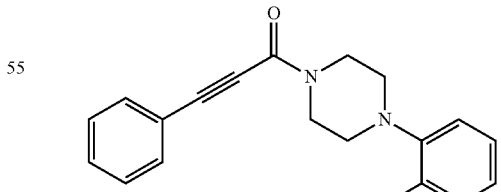

3-Phenyl-1-(4-(o-tolyl)piperazin-1-yl)prop-2-yn-1-one (10)

To a solution of phenyl propiolic acid (3e, 0.200 g, 1.37 mmol) in $CH_2Cl_2$ (12 mL) was added 1-(o-tolyl)piperazine (4b, 0.290 g, 1.64 mmol) and Et$_3$N (570 μL, 4.11 mmol). The reaction mixture was cooled to 0° C., treated with T3P (50 wt. % solution in EtOAc, 1.45 mL, 2.05 mmol), warmed to room temperature, stirred for 3 d, diluted with CH$_2$Cl$_2$ (30 mL), and washed with satd. aqueous NH$_4$Cl (5 mL), satd. aqueous NaHCO$_3$ (5 mL), and brine (5 mL), dried (Na$_2$SO$_4$), filtered, and concentrated in vacuo. The crude residue was purified by chromatography on SiO$_2$ (ISCO, 24 g column, liquid load in CH$_2$Cl$_2$, EtOAc/hexanes gradient (10-100%), product eluted at 40% EtOAc/hexanes) to give 10 (0.401 g, 1.32 mmol, 96%, >99.9% pure by ELSD) as a colorless solid: Mp 127-129° C.; IR (neat) 3037, 2907, 2857, 2206, 1616, 1491, 1424, 1279, 1226, 1207, 1035, 923, 758, 726, 686 cm$^{-1}$; $^1$H NMR (300 MHz, CDCl$_3$) δ 7.59-7.56 (m, 2H), 7.43-7.34 (m, 3H), 7.22-7.16 (m, 2H), 7.05-6.99 (m, 2H), 3.99 (app t, 2H, J=5.0 Hz), 3.85 (app t, 2H, J=5.0 Hz), 2.99 (app t, 2H, J=5.0 Hz), 2.92 (app t, 2H, J=5.0 Hz), 2.35 (s, 3H); $^{13}$C NMR (75 MHz, CDCl$_3$) δ 153.2, 150.8, 132.8, 132.4, 131.2, 130.1, 128.6, 126.8, 123.9, 120.5, 119.3, 90.9, 81.2, 52.2, 51.5, 47.7, 42.1, 17.8; HRMS (ESI) m/z calcd for C$_{20}$H$_{21}$ON$_2$ ([M+H]$^+$) 305.1648, found 305.1643.

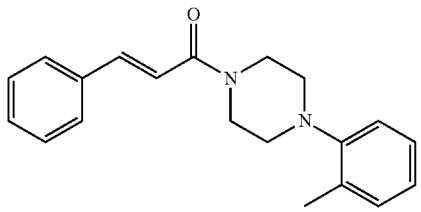 [SMILES: Cc1ccccc1N1CCN(C(=O)/C=C/c2ccccc2)CC1]

(E)-3-Phenyl-1-(4-(o-tolyl)piperazin-1-yl)prop-2-en-1-one (11)

A solution of trans-cinnamic acid (3f, 0.0400 g, 0.270 mmol) in CH$_2$Cl$_2$ (2.5 mL) was treated with 1-(o-tolyl)piperazine (4b, 0.0570 g, 0.320 mmol), Et$_3$N (113 μL, 0.810 mmol). The reaction mixture was cooled to 0° C., treated with T3P (50 wt. % solution in EtOAc, 290 μL, 0.405 mmol), warmed to room temperature, stirred for 3 d, diluted with CH$_2$Cl$_2$ (10 mL), and washed with satd. aqueous NH$_4$Cl (2 mL), satd. aqueous NaHCO$_3$ (2 mL), and brine (2 mL), dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-100%), product eluted at 35%, EtOAc/hexanes) to give 11 (0.0520 g, 0.168 mmol, 62%, >99% purity by ELSD) as a yellow solid: Mp 110-111° C.; IR (neat) 3045, 2920, 2840, 1643, 1595, 1423, 1327, 1225, 1152, 986, 765, 710, 682 cm$^{-1}$; $^1$H NMR (400 MHz, CDCl$_3$) δ 7.72 (d, 1H, J=11.4 Hz), 7.55 (dd, 2H, J=6.8, 1.4 Hz), 7.41-7.36 (m, 3H), 7.20 (dd, 2H, J=14.6, 7.4 Hz), 7.02 (ddd, 2H, J=14.6, 7.4, 0.6 Hz), 6.95 (d, 1H, J=15.6 Hz), 3.90 (brs, 2H), 3.81 (brs, 2H), 2.96 (brs, 4H), 2.36 (s, 3H); $^{13}$C NMR (75 MHz, CDCl$_3$) δ 165.5, 150.8, 142.8, 135.2, 132.7, 131.1, 129.6, 128.8, 127.7, 126.6, 123.7, 119.2, 117.1, 52.1, 51.6, 46.4, 42.6, 17.8; HRMS (ESI) m/z calcd for C$_{20}$H$_{23}$ON$_2$ ([M+H]$^+$) 307.1805, found 307.1796.

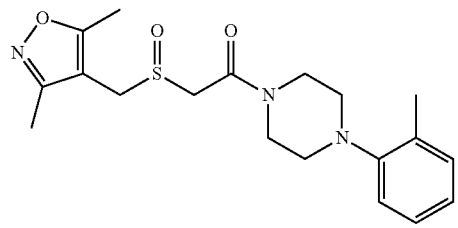 [SMILES: Cc1ccccc1N1CCN(C(=O)CS(=O)Cc2c(C)noc2C)CC1]

2-(((3,5-Dimethylisoxazol-4-yl)methyl)sulfinyl)-1-(4-(o-tolyl)piperazin-1-yl)ethan-1-one (12)

To a solution of 2-(((3,5-dimethylisoxazol-4-yl)methyl)thio)-1-(4-(o-tolyl)piperazin-1-yl)ethanone (5b, 0.0500 g, 0.139 mmol) in MeOH (0.30 mL) at 0° C. was added dropwise a solution of sodium metaperiodate (0.0301 g, 0.139 mmol) in water (0.14 mL). The resulting heterogeneous mixture was allowed to warm to room temperature and stirred for 15 h. The reaction mixture was filtered through a plug of Celite (MeOH), concentrated, dissolved in CH$_2$Cl$_2$, dried (MgSO$_4$), filtered and concentrated in vacuo. The crude residue was purified by chromatography on SiO$_2$ (100% EtOAc) to give 12 (0.0356 g, 0.0948 mmol, 68%, 100% pure by ELSD) as a colorless foam: IR (ATR) 2917, 2818, 1631, 1599, 1493, 1441, 1384, 1275, 1224, 1195, 1151, 1053, 1028, 911, 764, 727 cm$^{-1}$; $^1$H NMR (400 MHz, CDCl$_3$) δ 7.21-7.15 (m, 2H), 7.02 (app t, 1H, J=7.2 Hz), 6.97 (app d, 1H, J=8.0 Hz), 4.18 (d, 1H, J=14.0 Hz), 3.90-3.84 (m, 5H), 3.64 (app t, 2H, J=4.4 Hz), 2.95 (app t, 2H, J=4.4 Hz), 2.85 (brs, 2H), 2.45 (s, 3H), 2.32 (s, 3H), 2.31 (s, 3H); $^{13}$C NMR (100 MHz, CDCl$_3$) δ 169.2, 162.9, 159.9, 150.4, 132.7, 131.2, 126.7, 124.0, 119.2, 104.5, 53.7, 52.0, 51.5, 47.0, 46.8, 42.5, 17.7, 11.6, 10.3; HRMS (ESI) m/z calcd for C$_{19}$H$_{26}$N$_3$O$_3$S ([M+H]$^+$) 376.1689, found 376.1684.

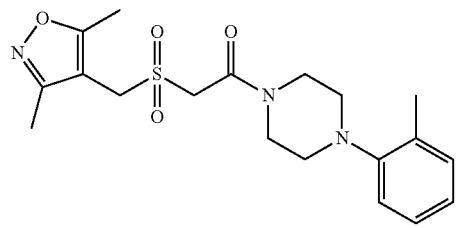 [SMILES: Cc1ccccc1N1CCN(C(=O)CS(=O)(=O)Cc2c(C)noc2C)CC1]

2-(((3,5-Dimethylisoxazol-4-yl)methyl)sulfonyl)-1-(4-(o-tolyl)piperazin-1-yl)ethan-1-one (13)

A solution of 2-(((3,5-dimethylisoxazol-4-yl)methyl)thio)-1-(4-(o-tolyl)piperazin-1-yl)ethanone (5b, 0.0429 g, 0.117 mmol) in CH$_2$Cl$_2$ (0.65 mL) was treated with 3-chloroperoxybenzoic acid (70 wt. %, 0.0576 g, 0.234 mmol) in 2 portions. The reaction mixture was stirred at room temperature for 15 h, quenched with 10% aqueous sodium metabisulfite solution (2 mL), diluted with aqueous 1 M NaOH (10 mL) and extracted with CH$_2$Cl$_2$ (2×15 mL). The combined organic layers were washed with 1 M NaOH (10 mL), dried (MgSO$_4$), filtered, and concentrated in vacuo. The crude residue was purified by chromatography on SiO$_2$ (70-100% EtOAc/hexanes) to give 13 (0.0203 g, 0.0519 mmol, 44%, 100% pure by ELSD) as a colorless foam: IR (ATR) 2919, 2819, 1641, 1599, 1493, 1445, 1318, 1225, 1150, 1126, 1030, 911, 765, 728 cm$^{-1}$; $^1$H NMR (400 MHz, CDCl$_3$) δ 7.21-7.16 (m, 2H), 7.05-6.98 (m, 2H), 4.36 (s, 2H), 4.09 (s, 2H), 3.85 (app brs, 2H), 3.72 (brt, 2H, J=4.0 Hz), 3.00 (brt, 2H, J=4.0 Hz), 2.93 (brt, 2H, J=4.4 Hz), 2.50 (s, 3H), 2.35 (s, 3H), 2.33 (s, 3H); $^{13}$C NMR (100 MHz, CDCl$_3$) δ 170.1, 160.7, 160.3, 150.3, 132.7, 131.2, 126.7, 124.0, 119.2, 101.8, 54.9, 51.7, 51.4, 48.3, 47.8, 43.0, 17.8, 11.5, 10.2; HRMS (ESI) m/z calcd for C$_{19}$H$_{26}$N$_3$O$_4$S ([M+H]$^+$) 392.1639, found 392.1633.

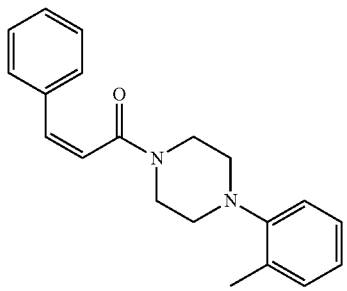 [SMILES: Cc1ccccc1N1CCN(C(=O)/C=C\c2ccccc2)CC1]

(Z)-3-Phenyl-1-(4-(o-tolyl)piperazin-1-yl)prop-2-en-1-one (14)

To a solution of 3-phenyl-1-(4-(o-tolyl)piperazin-1-yl)prop-2-yn-1-one (10, 0.103 g, 0.337 mmol) in MeOH (2 mL) and EtOAc (1 mL) was added Lindlar's catalyst (5% Pd on CaCO$_3$, lead poisoned, 0.120 g) and quinoline (15 µL, 0.130 mmol). The reaction mixture was purged and backfilled with H$_2$ (balloon, 2×), allowed to stir for 45 min, filtered through SiO$_2$, and concentrated in vacuo. The crude residue was purified by chromatography on SiO$_2$ (ISCO, modified dry load in CH$_2$Cl$_2$, 0-90% EtOAc/hexanes gradient, product eluted at 25% EtOAc/hexanes) to give 14 (0.104 g, 0.339 mmol, quant., 99.6% purity by ELSD) as a yellow oil: IR (neat) 3022, 2914, 2815, 1513, 1597, 1493, 1434, 1364, 1223, 1149, 1115, 1034, 973, 913, 855, 762, 722, 698 cm$^{-1}$; $^1$H NMR (300 MHz, CDCl$_3$) δ 7.41-7.30 (m, 5H), 7.17-7.11 (m, 2H), 6.98 (t, 1H, J=7.1 Hz), 6.81 (d, 1H, J=7.8 Hz), 6.71 (d, 1H, J=12.6 Hz), 6.07 (d, 1H, J=12.6 Hz), 3.81 (app brt, 2H, J=4.8 Hz), 3.48 (app t, 2H, J=4.8 Hz), 2.81 (app t, 2H, J=4.8 Hz), 2.44 (app t, 2H, J=4.8 Hz), 2.25 (s, 3H); $^{13}$C NMR (75 MHz, CDCl$_3$) δ 167.6, 150.9, 135.6, 133.5, 132.7, 131.1, 128.7, 128.6, 128.5, 126.6, 123.7, 123.2, 119.1, 51.5, 51.3, 46.8, 41.7, 17.7; HRMS (ESI) m/z calcd for C$_{20}$H$_{23}$ON$_2$ ([M+H]$^+$) 307.1805, found 307.1800.

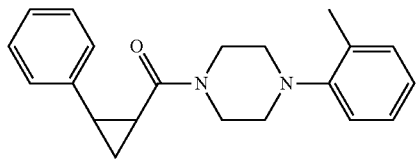 [SMILES: Cc1ccccc1N1CCN(C(=O)C2CC2c2ccccc2)CC1]

(2-Phenylcyclopropyl)(4-(o-tolyl)piperazin-1-yl)methanone (15)

A solution of anhydrous CrCl$_2$ (0.0486 g, 0.392 mmol) in THF (0.6 mL) at room temperature under N$_2$ was treated with a solution of (Z)-3-phenyl-1-(4-(o-tolyl)piperazin-1-yl)prop-2-en-1-one (14, 0.0200 g, 0.0653 mmol) in THF (0.5 mL) and CH$_2$ICl (20 µL, 0.261 mmol). The reaction mixture was stirred for 18 h at reflux, quenched by addition of 1 M aqueous HCl (6 mL) and extracted with EtOAc. The combined organic layers were dried (Na$_2$SO$_4$), filtered, and concentrated in vacuo. The crude residue was purified by chromatography on SiO$_2$ (4:1, EtOAc/hexanes) to give 15 (0.0120 g, 0.0375 mmol, 57%, 100% pure by ELSD) as a brown oil: IR (neat) 2920, 1638, 1491, 1457, 1340, 1223, 1028 cm$^{-1}$; $^1$H NMR (400 MHz, CDCl$_3$) δ 7.30-7.27 (m, 2H), 7.22-7.11 (m, 5H), 6.98 (dt, 1H, J=7.2, 1.2 Hz), 6.72 (dd, 1H, J=7.9, 0.8 Hz), 3.93-3.90 (m, 1H), 3.77-3.73 (m, 1H), 3.60-3.53 (m, 1H), 3.30-3.22 (m, 1H), 2.75-2.72 (m, 2H), 2.50-2.41 (m, 1H), 2.26 (s, 3H), 2.24-2.16 (m, 1H), 2.10-2.00 (m, 1H), 1.87 (dd, 1H, J=12.4, 5.8 Hz), 1.40-1.33 (m, 1H), 0.92-0.80 (m, 1H); $^{13}$C NMR (100 MHz, CDCl$_3$) δ 167.2, 150.9, 137.6, 132.7, 131.0, 128.2, 127.4, 126.5, 126.4, 123.6, 119.2, 51.9, 51.6, 45.7, 42.3, 24.4, 24.1, 17.7, 10.60 HRMS (ESI) m/z calcd for C$_{21}$H$_{25}$ON$_2$ ([M+H]$^+$) 321.1967, found 321.1961.

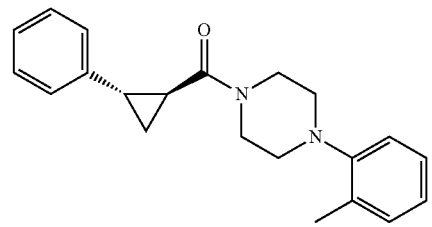 [SMILES: Cc1ccccc1N1CCN(C(=O)[C@H]2C[C@@H]2c2ccccc2)CC1]

((1SR,2SR)-2-Phenylcyclopropyl)(4-(o-tolyl)piperazin-1-yl)methanone (16)

To a solution of trans-2-phenylcyclopropanecarboxylic acid (3g, 0.0400 g, 0.247 mmol) in CH$_2$Cl$_2$ (2.5 mL) was treated with 1-(o-tolyl)piperazine (4b, 0.0540 g, 0.296 mmol), Et$_3$N (100 µL, 0.740 mmol). The reaction mixture was cooled to 0° C., treated with T3P (50 wt. % solution in EtOAc, 260 µL, 0.370 mmol, 1.5 equiv), warmed to room temperature, stirred for 3 d, diluted with EtOAc (10 mL), and washed with satd. aqueous NH$_4$Cl (2 mL), satd. aqueous NaHCO$_3$ (2 mL), and brine (2 mL), dried (Na$_2$SO$_4$), filtered, and concentrated in vacuo. The crude residue was purified by chromatography on SiO$_2$ (ISCO, 12 g column, liquid load in CH$_2$Cl$_2$, EtOAc/hexanes gradient (10-90%), product eluted at 20%) to give 16 (0.0676 g, 0.211 mmol, 86%, >99.9% pure by ELSD) as a yellow oil: IR (neat) 3026, 2912, 2814, 1631, 1600, 1493, 1440, 1381, 1223, 1150, 1033, 919, 910, 760, 723, 696 cm$^{-1}$; $^1$H NMR (300 MHz, CDCl$_3$) δ 7.32-7.26 (m, 2H), 7.23-7.12 (m, 5H), 7.01 (dd, 2H, J=11.1, 7.5 Hz), 3.79 (brs, 4H), 2.90 (brs, 4H), 2.52 (brpent, 1H, J=4.6 Hz), 2.33 (s, 3H), 2.02 (pent, 1H, J=4.6 Hz), 1.71 (pent, 1H, J=4.6 Hz), 1.34-1.26 (m, 2H); $^{13}$C NMR (100 MHz, CDCl$_3$) δ 170.6, 150.9, 141.0, 132.7, 131.2, 128.6, 126.7, 126.3, 126.1, 123.8, 119.2, 52.2, 51.7, 46.2, 25.6, 23.3, 17.9, 16.2; HRMS (ESI) m/z calcd for C$_{21}$H$_{25}$ON$_2$ ([M+H]$^+$) 321.1961, found 321.1957.

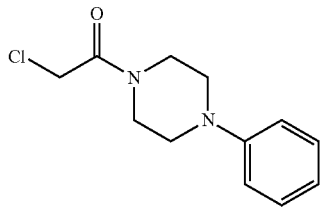 [SMILES: O=C(CCl)N1CCN(c2ccccc2)CC1]

2-Chloro-1-(4-(o-tolyl)piperazin-1-yl)ethanone (17a)

(Glennon et al., *J. Med. Chem.* 1986, 29, 2375-2380; Jorand-Lebrun et al., *J. Med. Chem.* 1997, 40, 3974-3978.). To a solution of chloroacetyl chloride (0.698 g, 6.05 mmol) and potassium carbonate (1.14 g, 8.25 mmol) in THF (7.0 mL) was added 1-(o-tolyl)piperazine (4b, 1.00 g, 5.50 mmol) in THF (12.6 mL) at 0° C. The reaction mixture was gradually warmed to room temperature, stirred for 16 h, diluted with water, and extracted with EtOAc (3×20 mL). The combined organic extracts were washed sequentially with satd. aqueous NaHCO$_3$, 0.1 M aqueous HCl, and brine, dried (Na$_2$SO$_4$), filtered and concentrated in vacuo. The crude solid was filtered through a plug of SiO$_2$ (3:7, EtOAc/hexanes v/v 1% Et$_3$N) and washed thoroughly with EtOAc/hexanes (3:7) to give 17a (1.37 g, 5.42 mmol, 99%) as an off white solid: $^1$H NMR (400 MHz, CDCl$_3$) δ 7.22-7.16 (m, 2H), 7.05-6.99 (m, 2H), 4.12 (s, 2H), 3.78 (app t, 2H, J=4.8 Hz), 3.67 (app t, 2H, J=4.8 Hz), 2.97 (app t, 2H, J=4.8 Hz), 2.91 (app t, 2H, J=4.8 Hz), 2.33 (s, 3H).

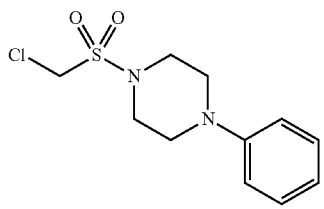 [SMILES: O=S(=O)(CCl)N1CCN(c2ccccc2)CC1]

1-(((Chloromethyl)sulfonyl)-4-(o-tolyl)piperazine (17b)

(Zhou et al., *J. Org. Lett.* 2008, 10, 2517-2520.). To a solution of 1-(o-tolyl)piperazine (4b, 0.500 g, 2.75 mmol) in CH$_2$Cl$_2$ (9.8 mL) and Et$_3$N (0.390 mL, 2.75 mmol) at 0° C. was added chloromethanesulfonyl chloride (0.460 g, 3.03 mmol). The reaction mixture was stirred at 0° C., gradually warmed to room temperature quenched after 14 h with satd. aqueous NH$_4$Cl solution (3 mL), and extracted with EtOAc (3×20 mL). The combined organic extracts were washed water (2×10 mL) and brine (10 mL), dried (Na$_2$SO$_4$), filtered and concentrated in vacuo. The crude solid was filtered through a plug of SiO$_2$ (3:7, EtOAc/hexanes containing 1% Et$_3$N) and washed thoroughly with EtOAc/hexanes (3:7). The combined filtrates were concentrated in vacuo to give 17b (0.676 g, 2.34 mmol, 85%) as an orange solid: $^1$H NMR (300 MHz, CDCl$_3$) δ 7.19 (t, 2H, J=8.1 Hz), 7.03 (t, 2H, J=8.1 Hz), 4.56 (s, 2H), 3.63 (app t, 4H, J=5.0 Hz), 2.99 (app t, 4H, J=5.0 Hz), 2.32 (s, 3H); $^{13}$C NMR (75 MHz, CDCl$_3$) δ 150.6, 132.7, 131.2, 126.8, 124.1, 119.4, 54.5, 51.9, 47.1, 17.7.

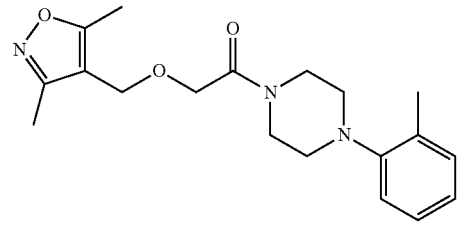 [SMILES: Cc1ccccc1N1CCN(C(=O)COCc2c(C)noc2C)CC1]

2-((3,5-Dimethylisoxazol-4-yl)methoxy)-1-(4-(o-tolyl)piperazin-1-yl)ethan-1-one (18a)

A solution of (3,5-dimethylisoxazol-4-yl)methanol (27, 0.0302 g, 0.237 mmol) in THF (0.48 mL) was cooled to 0° C. and NaH (60% dispersion in mineral oil, 0.0190 g, 0.475 mmol) was added. The reaction mixture was stirred at 0° C. for 30 min, treated with 2-chloro-1-(4-(o-tolyl)piperazin-1-yl)ethanone (17a, 0.0600 g, 0.237 mmol), warmed to room temperature, stirred for 20 h, quenched with brine (1 mL), diluted with EtOAc (15 mL) and brine (5 mL), and extracted with EtOAc (2×15 mL). The combined organic layers were dried (Na$_2$SO$_4$) and concentrated in vacuo. The crude residue was purified by chromatography on SiO$_2$ (3:2, EtOAc/hexanes) to give 18a (0.0735 g, 0.214 mmol, 90%, 100% pure by ELSD) as a light yellow oil: IR (ATR) 2918, 2817, 1645, 1599, 1493, 1443, 1369, 1273, 1225, 1116, 1030, 977, 764, 725 cm$^{-1}$; $^1$H NMR (400 MHz, CDCl$_3$) δ 7.21-7.16 (m, 2H), 7.02 (dt, 1H, J=7.6, 1.2 Hz), 6.97 (app d, 1H, J=8.0 Hz), 4.41 (s, 2H), 4.17 (s, 2H), 3.77 (brs, 2H), 3.59 (app t, 2H, J=4.8 Hz), 2.89 (app t, 4H, J=3.6 Hz), 2.41 (s, 3H), 2.32 (s, 3H), 2.30 (s, 3H); $^{13}$C NMR (125 MHz, CDCl$_3$) δ 167.8, 167.5, 159.8, 150.7, 132.7, 131.2, 126.7, 123.9, 119.2, 110.5, 68.7, 61.7, 52.1, 51.7, 45.6, 42.3, 17.8, 11.1, 10.1; HRMS (ESI) m/z calcd for C$_{19}$H$_{26}$N$_3$O$_3$ ([M+H]$^+$) 344.1969, found 344.1960.

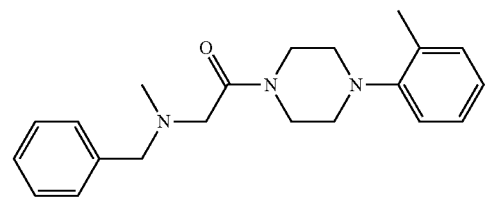 [SMILES: Cc1ccccc1N1CCN(C(=O)CN(C)Cc2ccccc2)CC1]

2-(Benzyl(methyl)amino)-1-(4-(o-tolyl)piperazin-1-yl)ethanone (18b)

A solution of 2-chloro-1-(4-(o-tolyl)piperazin-1-yl)ethanone (17a, 0.0534 g, 0.211 mmol), in CH$_3$CN (4 mL) was treated with N-methylbenzylamine (23 µL, 0.176 mmol) and K$_2$CO$_3$ (0.730 g, 0.528 mmol). The reaction mixture was heated at reflux for 5 h, cooled to room temperature, filtered, and concentrated in vacuo. The crude residue was purified by chromatography on SiO$_2$ (2:3, EtOAc/hexanes) to give 18b (0.0590 g, 0.175 mmol, 99%, >95% pure by LCMS) as a light yellow oil: IR (neat) 2933, 2816, 1640, 1450, 1491, 1222 cm$^{-1}$; $^1$H NMR (500 MHz, CDCl$_3$) δ 7.39-7.33 (m, 4H), 7.31-7.27 (m, 1H), 7.23-7.19 (m, 2H), 7.04 (t, 1H, J=7.5 Hz), 7.01 (d, 1H, J=8.0 Hz), 3.77 (brs, 2H), 3.71-3.69 (m, 2H), 3.61 (s, 2H), 3.27 (s, 2H), 2.91-2.87 (m, 4H), 2.35 (s, 3H) 2.34 (s, 3H); $^{13}$C NMR (125 MHz, CDCl$_3$) δ 150.9, 138.1, 132.6, 131.1, 129.1, 128.2, 127.2, 126.6, 123.6, 119.1, 62.0, 60.3, 52.1, 51.7, 46.1, 42.4, 42.2, 17.8; HRMS (ESI) m/z calcd for $C_{21}H_{28}N_3O$ ([M+H]$^+$) 338.2238, found 338.2211.

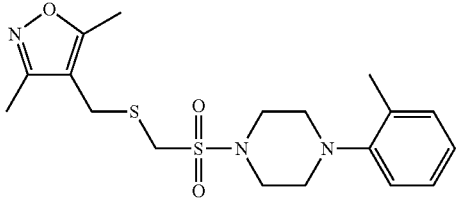 [SMILES: Cc1ccccc1N1CCN(S(=O)(=O)CSCc2c(C)noc2C)CC1]

3,5-Dimethyl-4-(((((4-(o-tolyl)piperazin-1-yl)sulfonyl)methyl)thio)methyl)isoxazole (18c)

A suspension of NaH (60% dispersion in mineral oil, 0.0200 g, 0.499 mmol) in THF (0.6 mL) was treated under an atmosphere of $N_2$ at 0° C. with a solution of (3,5-dimethylisoxazol-4-yl)methanethiol (25, 0.0536 g, 0.374 mmol) in THF (0.4 mL). The reaction mixture was stirred for 10 min, treated with 1-((chloromethyl)sulfonyl)-4-(o-tolyl)piperazine (17b, 0.0360 g, 0.125 mmol), stirred for 2 d at room temperature, quenched (water) and extracted (EtOAc). The combined organic layers were dried ($Na_2SO_4$), filtered, and concentrated in vacuo. The residue was purified by chromatography on $SiO_2$ (1:4, EtOAc/hexanes) to give crude 18c that was further purified by preparative TLC (2:3, $Et_2O$/hexanes) to give 18c (2.0 mg, 0.00506 mmol, 4%, 100% pure by ELSD) as a colorless oil: IR (neat) 2924, 1636, 1450, 1420, 1320, 1152 cm$^{-1}$; $^1$H NMR (400 MHz, CDCl$_3$) δ 7.20 (t, 2H, J=7.7 Hz), 7.06-7.00 (m, 2H), 3.87 (s, 2H), 3.76 (s, 2H), 3.58 (app t, 4H, J=4.8 Hz), 2.99 (app t, 4H, J=4.8 Hz), 2.44 (s, 3H), 2.32 (s, 3H), 2.31 (s, 3H); $^{13}$C NMR (100 MHz, CDCl$_3$) δ 167.5, 159.7, 150.6, 132.7, 131.2, 126.8, 124.0, 119.4, 108.7, 51.8, 48.6, 47.0, 24.1, 17.8, 11.1, 10.2; HRMS (ESI) m/z calcd for $C_{18}H_{26}O_3N_3S_2$ ([M+H]$^+$) 396.1416, found 396.1410.

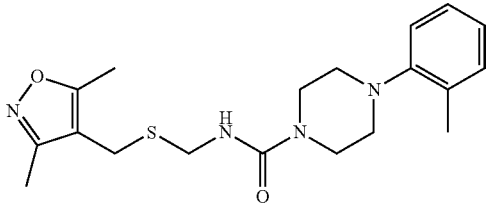 [SMILES: Cc1ccccc1N1CCN(C(=O)NCSCc2c(C)noc2C)CC1]

N-((((3,5-Dimethylisoxazol-4-yl)methyl)thio)methyl)-4-(o-tolyl)piperazine-1-carboxamide (20a)

To a solution of 2-(((3,5-dimethylisoxazol-4-yl)methyl)thio)acetic acid (3a, 0.0500 g, 0.248 mmol) in toluene (4.0 mL) was added DPPA (57 μL, 0.261 mmol) and Et$_3$N (37 μL, 0.261 mmol). The reaction mixture was heated at 110° C. for 60 min, cooled and washed with satd. aqueous NaHCO$_3$, dried (MgSO$_4$), filtered and concentrated to give the isocyanate 19 as a pink oil that was used without further purification.

A solution of 1-(o-tolyl)piperazine (4b, 0.460 g, 0.261 mmol) and Et$_3$N (37 μL, 0.261 mmol) in CH$_2$Cl$_2$ (0.5 mL) was cooled to 0° C. and treated with a solution of the isocyanate 19 in CH$_2$Cl$_2$ (0.5 mL). The reaction mixture was stirred overnight at room temperature, then diluted with EtOAc and satd. aqueous NH$_4$Cl. The organic layer was washed with satd. aqueous NaHCO$_3$ and brine, dried (Na$_2$SO$_4$), filtered, and concentrated in vacuo. The residue was purified by chromatography on SiO$_2$ (ISCO, 4 g column, gradient hexanes to 1:1, EtOAc/hexanes, with an initial base wash of the column using hexanes containing 1% Et$_3$N) to give 20a (0.0606 g, 0.162 mmol, 65%, 98% pure by ELSD) as a clear oil that turns to a red oil upon standing: IR (CH$_2$Cl$_2$) 3336, 2941, 2891, 2850, 1629, 1523, 1491, 1495, 1420, 1254, 1223, 1193, 997, 907, 761, 731 cm$^{-1}$; $^1$H NMR (300 MHz, CDCl$_3$) δ 7.18 (dd, 2H, J=8.7, 7.5 Hz), 7.04-6.98 (m, 2H), 4.88 (brt, 1H, J=6.0 Hz), 4.44 (d, 2H, J=6.0 Hz), 3.67 (s, 2H), 3.50 (app t, 4H, J=5.0 Hz), 2.89 (app t, 4H, J=5.0 Hz), 2.39 (s, 3H), 2.32 (s, 3H), 2.29 (s, 3H); $^{13}$C NMR (75 MHz, CDCl$_3$) δ 166.0, 159.5, 156.9, 150.9, 132.7, 131.2, 126.7, 123.7, 119.1, 110.8, 51.6, 44.4, 43.9, 23.6, 17.8, 11.0, 10.2; HRMS (ESI) m/z calcd for $C_{19}H_{27}N_4O_2S$ ([M+H]$^+$) 375.1849, found 375.1845.

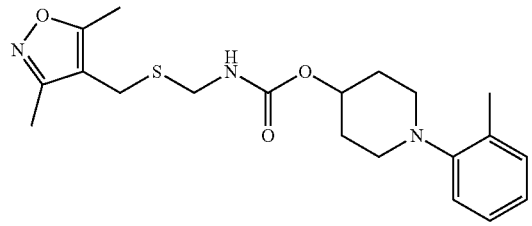 [SMILES: Cc1ccccc1N1CCC(OC(=O)NCSCc2c(C)noc2C)CC1]

1-(o-Tolyppiperidin-4-yl((((3,5-dimethylisoxazol-4-yl)methyl)thio)methyl)-carbamate (20b)

To a solution of 2-(((3,5-dimethylisoxazol-4-yl)methyl)thio)acetic acid (3a, 0.0500 g, 0.248 mmol) in toluene (4.0 mL) was added DPPA (0.06 mL, 0.261 mmol) and Et$_3$N (37 μL, 0.261 mmol). The reaction mixture was heated at 110° C. for 60 min, cooled to room temperature and treated with a solution of 1-(o-tolyl)piperidin-4-ol (4n, 0.0427 g, 0.224 mmol) in CH$_2$Cl$_2$ (0.5 mL). The reaction mixture was stirred overnight at 80° C., and diluted with EtOAc and satd. aqueous NH$_4$Cl. The organic layer was washed with satd. aqueous NaHCO$_3$ and brine, dried (Na$_2$SO$_4$), filtered, and concentrated in vacuo. The residue was purified by chromatography on SiO$_2$ (ISCO, 4 g column, gradient hexanes to 3:7, EtOAc/hexanes, with an initial base wash of the column with hexanes w/1% Et$_3$N) to give 20b (0.0168 g, 0.0431 mmol, 17%, 100% pure by ELSD) as a clear oil that eventually turned to a light yellow oil upon standing: IR (CH$_2$Cl$_2$) 3323, 2947, 2924, 2848, 2811, 1711, 1491, 1450, 1422, 1228, 1195, 1027, 762, 723 cm$^{-1}$; $^1$H NMR (400 MHz, DMSO-d6) δ 7.98 (t, 1H, J=6.4 Hz), 7.16-7.11 (m, 2H), 7.02 (d, 1H, J=7.2 Hz), 6.94 (dt, 1H, J=7.2, 1.2 Hz), 4.72-4.69 (m, 1H), 4.15 (d, 2H, J=6.4 Hz), 3.66 (s, 2H), 3.01-2.98 (m, 2H), 2.78-2.72 (m, 2H), 2.36 (s, 3H), 2.24 (s, 3H), 2.18 (s, 3H), 2.04-1.94 (m, 2H), 1.77-1.67 (m, 2H); $^{13}$C NMR (100 MHz, DMSO-d6) δ 165.7, 159.2, 155.5, 151.5, 131.8, 130.7, 126.5, 122.8, 118.9, 110.9, 69.9, 49.2, 42.9, 31.6, 21.9, 17.4, 10.5, 9.7; HRMS (ESI) m/z calcd for $C_{20}H_{28}N_3O_3S$ ([M+H]$^+$) 390.1846, found 390.1846.

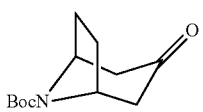

tert-Butyl 3-oxo-8-azabicyclo[3.2.1]octane-8-carboxylate (21a)

(WO 2012/152854 A1). A solution of nortropinone.HCl (21, 2.00 g, 12.4 mmol) in a minimum amount of water (6.0 mL) was cooled to 0° C., treated dropwise with 1 M NaOH (14.8 mL, 14.8 mmol, 1.2 equiv), warmed to room temperature over 20 min, extracted with $CH_2Cl_2$ (3×40 mL), dried ($MgSO_4$), filtered, and concentrated in vacuo (water bath at 23° C.) to give nortropinone 21 as the free base (1.54 g, quant.). The colorless oil was used without further purification.

To a solution of nortropinone 21 (1.54 g, 12.3 mmol) in $CH_2Cl_2$ (50 mL) cooled to 0° C. was added Boc anhydride (4.26 mL, 18.6 mmol), DMAP (0.302 g, 2.47 mmol), and $Et_3N$ (7.0 mL, 50.2 mmol). The reaction mixture was allowed to warm to room temperature and stirred overnight. After 19 h, the reaction mixture was concentrated in vacuo, and the residue was diluted with water, extracted with EtOAc (3×), washed with brine, dried ($MgSO_4$), filtered, and concentrated in vacuo to give a red sticky solid which was purified by chromatography on $SiO_2$ ($CH_2Cl_2$) to give 21a (2.18 g, 9.68 mmol, 78% over two steps) as a pale yellow oil that solidified to an off-white solid upon standing at room temperature: $^1H$ NMR (300 MHz, DMSO-d6) δ 4.34-4.30 (m, 2H), 2.55 (dt, 2H, J=15.6, 4.2 Hz), 2.23 (d, 2H, J=15.6 Hz), 2.20 (app s, 1H), 2.03-1.94 (m, 2H), 1.60-1.52 (m, 2H), 1.44 (s, 9H); $^{13}C$ NMR (75 MHz, DMSO-d6) δ 207.4, 152.6, 79.2, 52.7, 48.1, 28.0 (2 C).

tert-Butyl 3-(((trifluoromethyl)sulfonyl)oxy)-8-azabicyclo[3.2.1]oct-2-ene-8-carboxylate (22) (WO 2012/152854 A1)

A solution of NaHMDS (0.895 g, 4.88 mmol) in THF (12 mL) was added dropwise (over 10 min) at −78° C. to a solution of tert-butyl 3-oxo-8-azabicyclo[3.2.1]octane-8-carboxylate (21a, 1.00 g, 4.44 mmol) in THF (12 mL). The reaction mixture was stirred at −78° C. for 2 h, treated dropwise (over 20 min) with a solution of $PhN(Tf)_2$ (1.90 g, 5.33 mmol) in THF (12 mL), stirred for an additional 30 min at −78° C. and then allowed to warm to room temperature and stirred for 2 h. After addition of 10% aqueous $Na_2CO_3$ (50 mL), the solution was extracted with $Et_2O$ (2×75 mL). The combined organic layers were washed with 10% aqueous $Na_2CO_3$ solution, dried ($MgSO_4$), and concentrated in vacuo. The crude residue was purified by chromatography on $SiO_2$ (1:19, EtOAc/hexanes with 1% $Et_3N$) to give 22 (1.24 g, 3.47 mmol, 78%) as a clear oil that solidified to a wax upon storage at −20° C.: $^1H$ NMR (400 MHz, $CDCl_3$) δ 6.09 (brs, 1H), 4.54-4.38 (m, 2H), 3.07-3.02 (m, 1H), 2.30-2.20 (m, 1H), 2.11-1.99 (m, 3H), 2.00-1.97 (m, 2H), 1.79-1.70 (m, 1H), 1.45 (s, 9H).

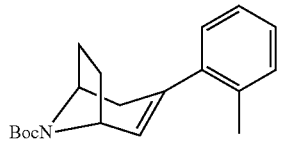 [SMILES: Cc1ccccc1C1=CC2CCC(C1)N2C(=O)OC(C)(C)C]

tert-Butyl 3-(o-tolyl)-8-azabicyclo[3.2.1]oct-2-ene-8-carboxylate (23a)

A solution of $Na_2CO_3$ (0.330 g, 3.11 mmol), lithium chloride (0.0600 g, 1.41 mmol), tert-butyl 3-(((trifluoromethyl)sulfonyl)oxy)-8-azabicyclo[3.2.1]oct-2-ene-8-carboxylate (22, 0.460 g, 1.41 mmol) and o-tolylboronic acid (0.235 g, 1.70 mmol) in DME (11 mL) and $H_2O$ (3 mL) was sparged with $N_2$ for 1 h, and treated with $Pd(PPh_3)_4$ (0.0376 g, 0.0325 mmol). The flask was evacuated and backfilled with nitrogen (3×) and the mixture was heated at 60° C. for 3 h. The mixture was allowed to cool to room temperature, diluted with brine, extracted with EtOAc (3×), dried ($Na_2SO_4$), and concentrated in vacuo. The resulting brown oil was dry loaded onto $SiO_2$ and purified by chromatography on $SiO_2$ (hexanes to 15:1, hexanes/EtOAc) to give 23a (0.330 g, 1.10 mmol, 78%) as a colorless solid: Mp 67.5-68.4° C.; IR (neat) 2975, 2934, 1685, 1420, 1364, 1329, 1169, 1094 cm$^{-1}$; $^1H$ NMR (400 MHz, $CDCl_3$, mixture of rotamers) δ 7.20-7.12 (m, 3H), 7.02-7.00 (m, 1H), 5.94-5.86 (m, 1H), 4.50-4.30 (m, 2H), 3.11-2.91 (m, 1H), 2.27 (app s, 4H), 2.10-1.90 (m, 3H), 1.90-1.80 (m, 1H), 1.50 (s, 9H); $^{13}C$ NMR (100 MHz, $CDCl_3$, 1:1 mixture of rotamers) δ 154.4, 141.6, 136.2, 135.5, 134.9, 131.3, 130.8, 130.7, 130.1, 129.3, 128.1, 126.9, 126.8, 125.6, 123.5, 120.0, 114.8, 79.3, 53.6, 52.9, 52.7, 52.0, 39.2, 38.4, 34.9, 34.3, 30.4, 29.6, 28.4, 19.5, 15.8; HRMS (ESI) m/z calcd for $C_{14}H_{17}N$ ([M+H—$C_5H_9O_2]^+$) 200.1439, found 200.1435.

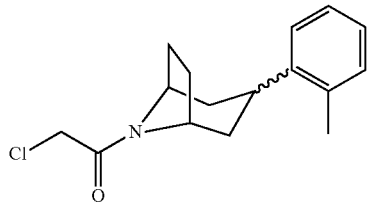 [SMILES: Cc1ccccc1C1CC2CCC(C1)N2C(=O)CCl]

2-Chloro-1-(3-(o-tolyl)-8-azabicyclo[3.2.1]octan-8-yl)ethan-1-one (24)

A solution of tert-butyl 3-(o-tolyl)-8-azabicyclo[3.2.1]oct-2-ene-8-carboxylate (23a, 0.196 g, 0.655 mmol) in EtOH (5.0 mL) was treated with Pd/C (5%, 0.0480 g). The flask was evacuated and flushed with $H_2$ (balloon, 3×). The reaction mixture was stirred under $H_2$ (1 atm, balloon) overnight, filtered through Celite, rinsed with EtOH and concentrated in vacuo to give (23, 0.160 g, 0.531 mmol, 81%) as a yellow liquid that was used without further purification.

A solution of 23 (0.200 g, 0.664 mmol) in $CH_2Cl_2$ (5 mL) was treated at room temperature with TFA (0.30 mL, 3.98 mmol). After 16 h, the solution was concentrated in vacuo.

The oily residue was extracted with CH$_2$Cl$_2$, washed with satd. aqueous NaHCO$_3$ and brine, dried (Na$_2$SO$_4$), filtered, and concentrated in vacuo to give 3-(o-tolyl)-8-azabicyclo[3.2.1]octane (23b, 0.133 g, 0.661 quant) as a light yellow oil that was used without further purification.

A solution of 23b (0.130 g, 0.646 mmol) and Et$_3$N (0.10 mL, 0.710 mmol) in THF (3 mL) was cooled to 0° C. and treated with chloroacetyl chloride (60 µL, 0.710 mmol) dropwise over 1 min. The reaction mixture was stirred at 0° C. for 1 h and then at room temperature for 20 h. The solution was filtered, concentrated in vacuo and the residue was dissolved in EtOAc, washed with water, dried (Na$_2$SO$_4$), filtered, and concentrated in vacuo. The crude residue was purified by chromatography on SiO$_2$ (1:1, hexanes/EtOAc) to give 24 (0.141 g, 0.508 mmol, 79%) as a brown oil. $^1$H NMR analysis indicated an approximately 4:3 ratio of endo/exo isomers: $^1$H NMR (400 MHz, CDCl$_3$) δ 7.22-7.09 (m, 6.8H), 4.85-4.80 (m, 1H), 4.80-4.74 (m, 0.7H), 4.38-4.30 (m, 1.7H), 4.14-4.04 (m, 3.6H), 3.49-3.39 (m, 1H), 2.99-2.88 (m, 0.7H), 2.58-2.49 (m, 1H), 2.38 (s, 3H), 2.32 (s, 2H), 2.22-1.70 (m, 11H), 1.55-1.48 (m, 1H); $^{13}$C NMR (100 MHz, CDCl$_3$) δ 163.4, 162.1, 141.8, 141.7, 135.9, 135.0, 130.4 (2 C), 126.5, 126.4, 126.2, 126.1 (2 C), 126.0, 55.7, 55.4, 52.6, 49.6, 41.5, 41.4, 39.5, 39.1, 37.9, 37.5, 32.8, 30.9, 30.3, 29.7, 28.9, 27.1, 19.4, 19.3; HRMS (ESI) m/z calcd for C$_{16}$H$_{21}$ClNO ([M+H]$^+$), 298.1312, found 298.1301.

to give 26a (16.2 mg, 0.0421 mmol, 29%, 99.8% pure by ELSD) and 26b (16.6 mg, 0.0432 mmol, 30%, 100% pure by ELSD) as light yellow oils.

26a (dr 82:18 by $^1$HNMR): IR (neat) 2952, 2933, 1629, 1446, 1424, 1195 cm$^{-1}$; $^1$H NMR (400 MHz, CDCl$_3$) δ 7.17-7.11 (m, 4H), 4.81-4.80 (m, 1H), 4.25-4.24 (m, 1H), 3.72 (s, 2H), 3.46-3.40 (m, 1H), 3.19 (s, 2H), 2.44 (brs, 4H), 2.37 (s, 3H), 2.31 (s, 3H), 2.19-2.09 (m, 1H), 2.08-1.84 (m, 5H), 1.80-1.66 (m, 2H); $^{13}$C NMR (100 MHz, CDCl$_3$) δ 166.8, 164.8, 159.8, 141.9, 135.1, 130.5, 126.5, 126.2, 126.0, 109.9, 55.8, 52.2, 39.2, 37.6, 32.5, 30.4, 28.9, 27.3, 23.8, 19.3, 11.0, 10.1; HRMS (ESI) m/z calcd for C$_{22}$H$_{29}$O$_2$N$_2$S ([M+H]$^+$) 385.1950, found 385.1946.

26b (dr 92:8 by $^1$HNMR): IR (neat) 2952, 2934, 1629, 1489, 1446, 1193, 1163 cm$^{-1}$; $^1$H NMR (400 MHz, CDCl$_3$) δ 7.20-7.12 (m, 4H), 4.76 (t, 1H, J=7.6 Hz), 4.20 (t, 1H, J=7.6 Hz), 3.80 (d, 1H, J=14.0 Hz), 3.62 (d, 1H, J=14.0 Hz), 3.20 (d, 1H, J=12.8 Hz), 3.10 (d, 1H, J=13.6 Hz), 3.01-2.90 (m, 1H), 2.60-2.45 (m, 5H), 2.40 (s, 6H), 2.22-2.11 (m, 1H), 2.10-2.00 (m, 1H), 1.85-1.69 (m, 2H), 1.55-1.40 (m, 2H); $^{13}$C NMR (100 MHz, CDCl$_3$) δ 166.9, 166.3, 159.8, 142.0, 135.7, 130.4, 126.5, 126.2, 126.0, 109.9, 53.3, 49.3, 39.0, 38.0, 32.8, 31.9, 31.1, 29.9, 23.9, 19.5, 11.1, 10.2; HRMS (ESI) m/z calcd for C$_{22}$H$_{29}$O$_2$N$_2$S ([M+H]$^+$) 385.1950, found 385.1944.

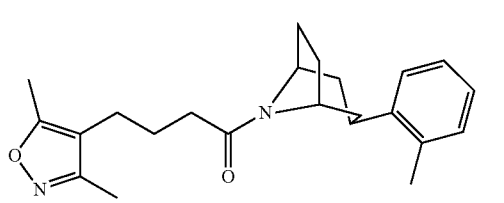

26a

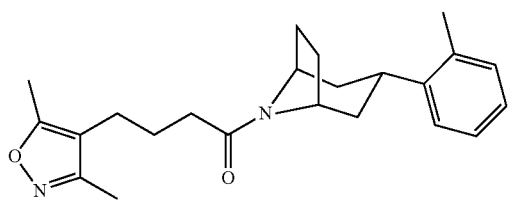

26b 2-(((3,5-Dimethylisoxazol-4-yl)methyl)thio)-1-(3-endo-(o-tolyl)-8-azabicyclo[3.2.1]octan-8-yl)ethanone (26a) and 2-4(3,5-dimethylisoxazol-4-yl)methyl)thio)-1-(3-exo-(o-tolyl)-8-azabicyclo[3.2.1]octan-8-yl)ethanone (26b)

A solution of (3,5-dimethylisoxazol-4-yl)methanethiol (25, 0.0247 g, 0.172 mmol) in THF (0.4 mL) was added to a suspension of NaH (60% dispersion in mineral oil, 0.0115 g, 0. mmol) in THF (1.0 mL) at 0° C. The resultant slurry was stirred at 0° C. for 30 min and a solution of 2-chloro-1-(3-(o-tolyl)-8-azabicyclo[3.2.1]octan-8-yl)ethanone (24, 0.0400 g, 0.144 mmol) in THF (0.4 mL) was added. The reaction mixture was allowed to warm to room temperature, stirred for 24 h, quenched with brine (1 mL), diluted with EtOAc (15 mL) and brine (5 mL), and extracted with EtOAc (2×15 mL). The combined organic layers were dried (Na$_2$SO$_4$) and concentrated in vacuo. The crude residue was purified by chromatography on SiO$_2$ (3:7, EtOAc/hexanes)

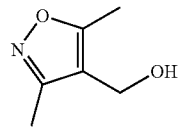

(3,5-Dimethylisoxazol-4-yl)methanol (27)

(Natale et al., *Synth. Commun.* 1983, 13, 817-822.) To a solution of 3,5-dimethylisoxazole-4-carboxylic acid (1.60 g, 11.3 mmol) in THF (69 mL) at 0° C. was added dropwise a 2 M solution of LiAlH$_4$ in THF (5.6 mL, 11.2 mmol). The reaction mixture was allowed to warm to room temperature, stirred overnight, transferred to a 500-mL Erlenmeyer flask and treated with sodium sulfate decahydrate until the foaming subsided. Celite (2.3 g) was added and the slurry was filtered and washed with CH$_2$Cl$_2$ (75 mL). The filtrate was concentrated in vacuo to give 27 (1.14 g, 8.97 mmol, 79%) as a clear colorless oil: $^1$H NMR (400 MHz, CDCl$_3$) δ 4.46 (s, 2H), 2.38 (s, 3H), 2.29 (s, 3H).

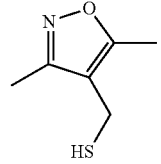

(3,5-Dimethylisoxazol-4-yl)methanethiol (25)

(Moreno-Mañas et al., *J. Heterocycl. Chem.* 1992, 29, 1557-1560.) A solution of (3,5-dimethylisoxazol-4-yl)methanol (27, 0.500 g, 3.90 mmol) in toluene (13 mL) was treated with Lawesson's reagent (0.890 g, 2.15 mmol) at room temperature, heated to 80° C. and stirred for 1 d. The crude mixture was loaded directly onto SiO$_2$ and purified by chromatography on SiO$_2$ (4:1, hexanes/EtOAc) to give 25 (0.115 g, 0.803 mmol, 21%) as a light yellow oil: $^1$H NMR (300 MHz, CDCl$_3$) δ 3.49 (d, 2H, J=6.6 Hz), 2.36 (s, 3H), 2.30 (s, 3H), 1.64 (t, 1H, J=6.6 Hz); $^{13}$C NMR (75 MHz, CDCl$_3$) δ 165.2, 159.0, 113.3, 15.9, 10.9, 10.0.

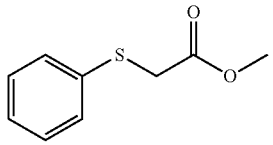

Methyl 2-(phenylthio)acetate (28)

(Bahrami et al., *J. Org. Chem.* 2010, 75, 6208-6213.) A solution of thiophenol (0.10 mL, 0.977 mmol), and methyl bromoacetate (0.164 g, 1.07 mmol) in THF (13 mL) was treated with Et$_3$N (0.17 mL, 1.17 mmol), stirred at room temperature for 4 h, and diluted with Et$_2$O and satd. aqueous NaHCO$_3$. The aqueous layer was extracted with Et$_2$O (2×5 mL). The combined organic layers were dried (MgSO$_4$), filtered and concentrated in vacuo to give 28 (0.176 g, 0.966 mmol, 99%) as a clear oil: $^1$H NMR (300 MHz, CDCl$_3$) δ 7.42-7.38 (m, 2H), 7.33-7.20 (m, 3H), 3.71 (s, 3H), 3.65 (s, 2H); $^{13}$C NMR (75 MHz, CDCl$_3$) δ 170.1, 134.9, 129.9, 129.0, 127.0, 52.5, 36.5.

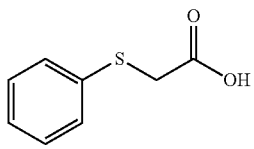 [SMILES: O=C(O)CSc1ccccc1]

2-(Phenylthio)acetic acid (3d)

(Bahrami et al., *J. Org. Chem.* 2010, 75, 6208-6213; Miura et al., *Org. Lett.* 2001, 3, 2591-2594.) To a solution of methyl 2-(phenylthio)acetate (28, 0.176 g, 0.966 mmol) in MeOH (2 mL) was added 2 M LiOH (1 mL). The reaction mixture was stirred at room temperature for 1 h and TLC analysis (4:1, hexanes/EtOAc) indicated that 28 had been consumed. The solution was concentrated in vacuo, diluted with water (3 mL) and acidified to pH 2 with 1 M HCl at 0° C. The aqueous layer was extracted with EtOAc (3×10 mL). The combined organic layers were dried (MgSO$_4$), filtered and concentrated in vacuo to give 3d (0.144 g, 0.857 mmol, 89%) as a colorless solid: $^1$H NMR (300 MHz, CDCl$_3$) δ 11.27 (brs, 1H), 7.43 (d, 2H, J=7.6 Hz), 7.36-7.24 (m, 3H), 3.69 (s, 2H); $^{13}$C NMR (75 MHz, CDCl$_3$) δ 175.9, 134.4, 130.1, 129.2, 127.2, 36.6.

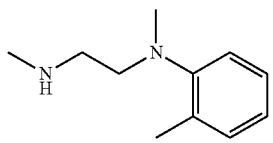

N,N'-Dimethyl-N-(o-tolyl)ethane-1,2-diamine (4i)

(Gruseck et al., *Tet. Lett.* 1987, 28, 6027-6030.). A microwave vial was flushed with argon and charged with the N,N'-dimethylethylenediamine (0.180 g, 2.04 mmol), NaO-t-Bu (0.202 g, 2.04 mmol), (rac)-BINAP (0.0162 g, 0.0260 mmol), Pd$_2$(dba)$_3$ (0.0078 g, 0.0085 mmol), degassed toluene (10.2 mL), and 2-bromotoluene (0.297 g, 1.70 mmol). The reaction mixture was heated in the sealed vial under argon at 110° C. for 24 h, cooled to room temperature, diluted with CH$_2$Cl$_2$, filtered through Celite, and concentrated in vacuo. The residue was purified by chromatography on basic Al$_2$O$_3$ (95:5, CH$_2$Cl$_2$/MeOH) to give 4i (0.0508 g, 0.285 mmol, 17%) as a brown oil: $^1$H NMR (400 MHz, CDCl$_3$) δ 7.16 (t, 2H, J=7.6 Hz), 7.08 (d, 1H, J=7.6 Hz), 6.98 (d, 1H, J=7.2 Hz), 3.05 (t, 2H, J=6.4 Hz), 2.71 (t, 2H, J=6.4 Hz), 2.65 (s, 3H), 2.43 (s, 3H), 2.32 (s, 3H), 1.36 (brs, 1H); HRMS (ESI) m/z calcd for C$_{11}$H$_{19}$N$_2$ ([M+H]$^+$) 179.1543, found 179.1541.

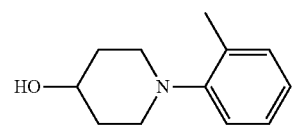

1-(o-Tolyl)piperidin-4-ol (4n)

(Harris et al., *Org. Lett.* 2002, 4, 2885-2888.) An oven-dried microwave tube was charged with Pd$_2$(dba)$_3$ (0.0606 g, 0.0653 mmol), CyJohnphos (0.0292 g, 0.0816 mmol), and 4-piperidinol (0.330 g, 3.26 mmol). The microwave tube was evacuated and back-filled with argon. A 1 M solution of LiN(TMS)$_2$ (1.21 g, 7.17 mmol) in degassed THF (7.2 mL) was added via syringe along with 2-bromotoluene (0.600 g, 3.26 mmol). The reaction vessel was sealed and heated at 65° C. with stirring for 22 h. The reaction mixture was cooled to room temperature, quenched with 1 M HCl (10 mL), stirred at room temperature for 5 min, neutralized with a satd. aqueous NaHCO$_3$ solution, and diluted with EtOAc. The organic layer was dried (MgSO$_4$), filtered through Celite, and concentrated in vacuo. The crude residue was purified by chromatography on SiO$_2$ (ISCO, 12 g column, gradient hexanes to 3:7, EtOAc/hexanes) to give 4n (0.372 g, 1.94 mmol, 60%) as a brown oil: $^1$H NMR (300 MHz, CDCl$_3$) δ 7.17 (dd, 2H, J=9.3, 7.2 Hz), 7.04-6.96 (m, 2H), 3.87-3.81 (m, 1H), 3.15-3.08 (m, 2H), 2.74 (dt, 2H, J=9.6, 2.7 Hz), 2.32 (s, 3H), 2.06-2.00 (m, 2H), 1.80-1.69 (m, 3H); $^{13}$C NMR (75 MHz, CDCl$_3$) δ 151.9, 132.7, 130.9, 126.4, 123.0, 119.0, 68.0, 49.8, 35.2, 17.7; HRMS (ESI) m/z calcd for C$_{12}$H$_{18}$NO ([M+H]$^+$) 192.1383, found 192.1307.

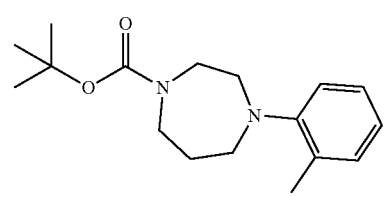 [SMILES: Cc1ccccc1N1CCCN(C(=O)OC(C)(C)C)CC1]

tert-Butyl 4-(o-tolyl)-1,4-diazepane-1-carboxylate (29a)

A microwave vial was flushed with argon and charged with Boc-homopiperazine (0.223 g, 1.10 mmol), NaO-t-Bu (0.116 g, 1.20 mmol), (rac)-BINAP (0.0478 g, 0.0752 mmol, 7.5 mol %), Pd$_2$(dba)$_3$ (0.0233 g, 0.0251 mmol), degassed toluene (2.8 mL), and 2-bromotoluene (0.175 g, 1.00 mmol). The reaction mixture was heated in the sealed vial under argon at 80° C. for 19 h, cooled to room temperature, diluted with CH$_2$Cl$_2$, filtered through Celite, and concentrated in vacuo. The residue was purified by chromatography on SiO$_2$ (1:9, EtOAc/hexanes) to give 29a (0.139 g, 0.479 mmol, 48%) as a yellow oil: IR (ATR) 2973, 2828, 1689, 1598, 1491, 1457, 1411, 1364, 1233, 1215, 1156, 1122, 878, 761, 725 cm$^{-1}$; $^1$H NMR (500 MHz, CDCl$_3$, room temperature, mixture of rotamers) δ 7.16 (d, 1H, J=6.0 Hz), 7.12 (d, 1H, J=6.0 Hz), 7.04 (d, 1H, J=7.5 Hz), 6.95 (t, 1H, J=7.0 Hz), 3.61-3.56 (m, 4H), 3.11-3.04 (m, 4H), 2.31 (s, 3H), 1.96-1.91 (m, 2H), 1.49 (s, 9H); $^{13}$C NMR (100 MHz, CDCl$_3$, room temperature, mixture of rotamers) δ 155.6, 155.5, 153.9, 153.8, 132.9, 130.9, 126.5, 123.1, 120.8 (2 C), 79.3, 56.2, 56.0, 55.5, 55.2, 48.4, 48.0, 46.2, 45.4, 29.0, 28.9, 28.5, 18.5; HRMS (ESI) m/z calcd for C$_{17}$H$_{27}$N$_2$O$_2$ ([M+H]$^+$) 291.2067, found 291.2062.

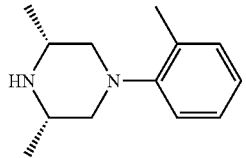

(3S,5R)-3,5-Dimethyl-1-(o-tolyl)piperazine (4k)

(WO 2015/042297 A1). A Schlenk flask was flushed with N$_2$ and charged with cis-2,6-dimethylpiperazine (0.110 g, 0.963 mmol), NaO-t-Bu (0.170 g, 1.75 mmol), (rac)-BINAP (0.0084 g, 0.0130 mmol), Pd$_2$(dba)$_3$ (0.0083 g, 0.0087 mmol), degassed toluene (4 mL), and 2-bromotoluene (0.150 g, 0.880 mmol). The reaction mixture was heated under N$_2$ at 110° C. for 24 h, cooled to room temperature, diluted with CH$_2$Cl$_2$, filtered through Celite, and concentrated in vacuo. The crude residue was purified by chromatography on SiO$_2$ (1:19, MeOH/CH$_2$Cl$_2$) to give 4k (0.140 g, 0.685 mmol, 78%) as clear, yellow oil: $^1$H NMR (500 MHz, CDCl$_3$) δ 7.19-7.15 (m, 2H), 7.02-6.98 (m, 2H), 3.13-3.10 (m, 2H), 3.01 (app d, 2H, J=10.5 Hz), 2.35-2.31 (m, 5H), 1.12 (d, 6H, J=6.5 Hz).

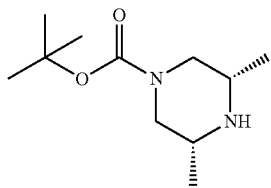

tert-Butyl (3R,5S)-3,5-dimethylpiperazine-1-carboxylate (30)

(Jacobsen et al., *J. Med. Chem.* 1999, 42, 1123-1144.) To a solution of cis-2,6-dimethylpiperazine (0.500 g, 4.38 mmol) in CH$_2$Cl$_2$ (11 mL) at 0° C. was added dropwise a solution of Boc-anhydride (0.946 g, 4.33 mmol) in CH$_2$Cl$_2$ (2.6 mL). The reaction mixture was allowed to warm to room temperature, stirred overnight, diluted with CH$_2$Cl$_2$ and washed with satd. aqueous Na$_2$CO$_3$ solution. The aqueous layer was extracted with CH$_2$Cl$_2$. The combined organic layers were washed with brine, dried (MgSO$_4$), filtered, and concentrated in vacuo to give 30 (0.813 g, 3.79 mmol, 87%) as an off-white solid: $^1$H NMR (300 MHz, CDCl$_3$) δ 4.10-3.80 (m, 2H), 2.85-2.70 (m, 2H), 2.40-2.20 (m, 2H), 1.46 (s, 9H), 1.05 (d, 6H, J=6.3 Hz).

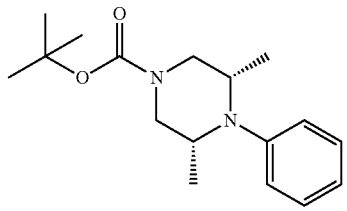 [SMILES: C[C@@H]1CN(C(=O)OC(C)(C)C)C[C@H](C)N1c1ccccc1]

tert-Butyl (3R,5S)-3,5-dimethyl-4-phenylpiperazine-1-carboxylate (29b)

To a sealed tube under an argon atmosphere was added a solution of KHMDS (0.241 g, 1.15 mmol) in dry 1,4-dioxane (2.0 mL), a solution of tert-butyl 3,5-dimethylpiperazine-1-carboxylate (30, 0.246 g, 1.15 mmol) in dry 1,4-dioxane (0.9 mL) and bromobenzene (100 μL, 0.955 mmol). The reaction mixture was stirred at 100° C. for 18 h, cooled to room temperature, quenched with water (5 mL), diluted with Et$_2$O (15 mL) and the aqueous layer was extracted with Et$_2$O (2×15 mL). The combined organic layers were washed with brine, dried (Na$_2$SO$_4$), filtered, and concentrated in vacuo. The crude residue was purified by chromatography on SiO$_2$ (1:9, EtOAc/hexanes) to give 29b (0.0970 g, 0.334 mmol, 35%) as a colorless oil: $^1$H NMR (300 MHz, CDCl$_3$) δ 7.33-7.27 (m, 2H), 7.15-7.09 (m, 3H), 4.00-3.80 (m, 2H), 3.07-3.03 (m, 2H), 2.82 (brt, 2H, J=11.7 Hz), 1.50 (s, 9H), 0.77 (d, 6H, J=6.3 Hz).

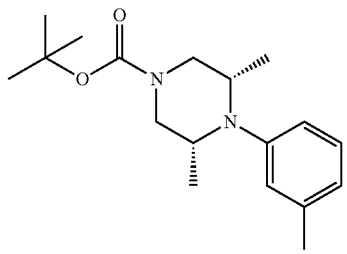 [SMILES: Cc1cccc(N2[C@H](C)CN(C(=O)OC(C)(C)C)C[C@@H]2C)c1]

tert-Butyl 3,5-dimethyl-4-(m-tolyl)piperazine-1-carboxylate (29c)

A sealed tube under an argon atmosphere was treated with KHMDS (0.221 g, 1.05 mmol) in dry 1,4-dioxane (2.0 mL), a solution of tert-butyl 3,5-dimethylpiperazine-1-carboxylate (30, 0.226 g, 1.05 mmol) in dry 1,4-dioxane (0.7 mL) and bromotoluene (105 μL, 0.877 mmol). The reaction mixture was stirred at 100° C. for 18 h, cooled to room temperature, quenched with water (5 mL), diluted with Et$_2$O (15 mL) and the aqueous layer was extracted with Et$_2$O (2×15 mL). The combined organic layers were washed with brine, dried (Na$_2$SO$_4$), filtered, and concentrated in vacuo. The crude residue was purified by chromatography on SiO$_2$ (1:9, EtOAc/hexanes) to give 29c (0.0441 g, 0.145 mmol, 17%) as a colorless oil: $^1$H NMR (300 MHz, CDCl$_3$) δ 7.18 (t, 1H, J=7.5 Hz), 6.96-6.89 (m, 3H), 4.00-3.80 (m, 2H), 3.06-3.00 (m, 2H), 2.81 (brt, 2H, J=11.7 Hz), 2.32 (s, 3H), 1.50 (s, 9H), 0.77 (d, 6H, J=6.3 Hz).

Example 2

Synthesis and Characterization of (4-(5-Chloro-2-methylphenyl)piperazin-1-yl)((1RS,2SR)-2-(4-fluorophenyl)cyclopropyl)methanone (JJ-450)

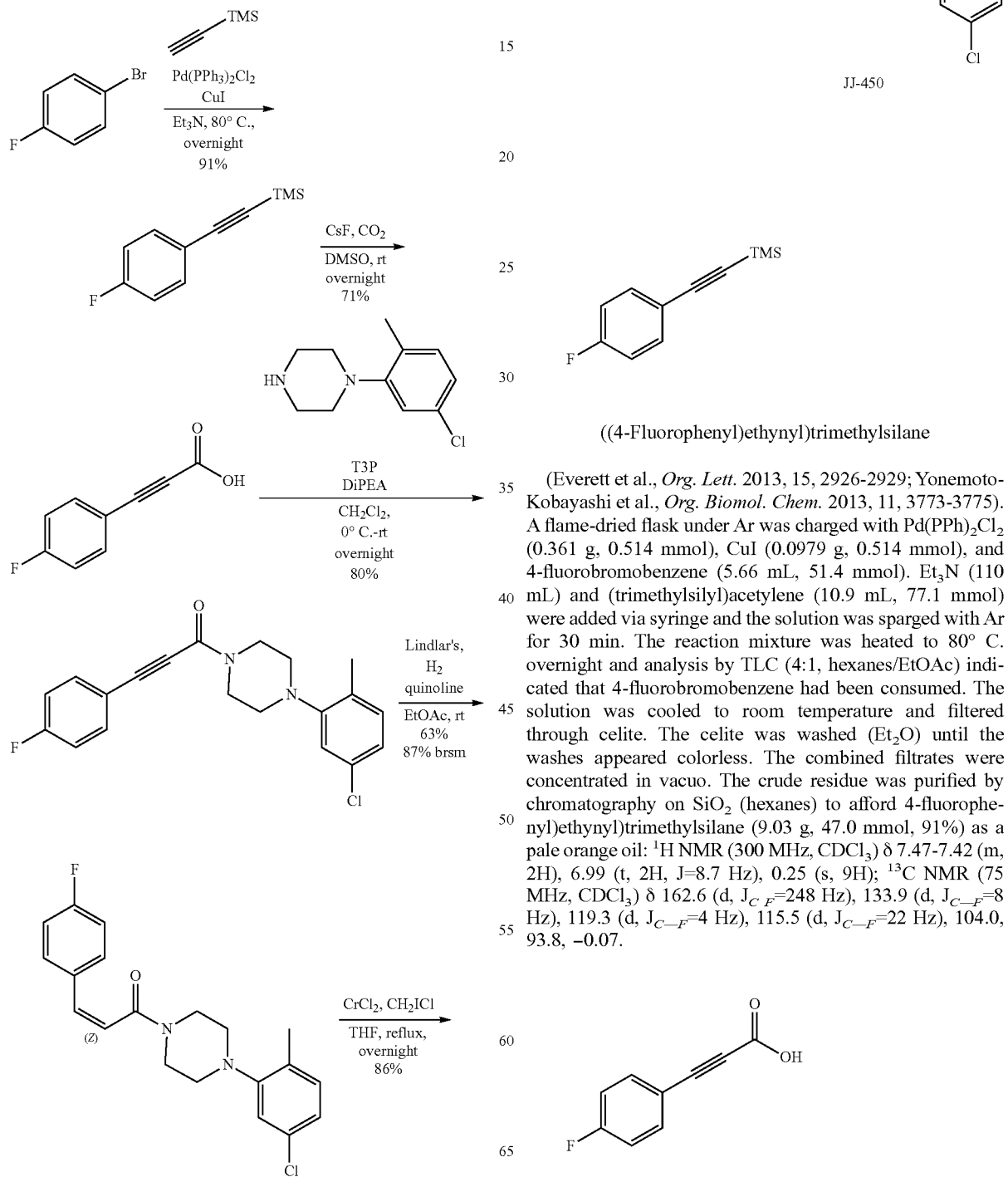

((4-Fluorophenyl)ethynyl)trimethylsilane (Everett et al., *Org. Lett.* 2013, 15, 2926-2929; Yonemoto-Kobayashi et al., *Org. Biomol. Chem.* 2013, 11, 3773-3775). A flame-dried flask under Ar was charged with $Pd(PPh)_2Cl_2$ (0.361 g, 0.514 mmol), CuI (0.0979 g, 0.514 mmol), and 4-fluorobromobenzene (5.66 mL, 51.4 mmol). $Et_3N$ (110 mL) and (trimethylsilyl)acetylene (10.9 mL, 77.1 mmol) were added via syringe and the solution was sparged with Ar for 30 min. The reaction mixture was heated to 80° C. overnight and analysis by TLC (4:1, hexanes/EtOAc) indicated that 4-fluorobromobenzene had been consumed. The solution was cooled to room temperature and filtered through celite. The celite was washed ($Et_2O$) until the washes appeared colorless. The combined filtrates were concentrated in vacuo. The crude residue was purified by chromatography on $SiO_2$ (hexanes) to afford 4-fluorophenyl)ethynyl)trimethylsilane (9.03 g, 47.0 mmol, 91%) as a pale orange oil: $^1H$ NMR (300 MHz, $CDCl_3$) δ 7.47-7.42 (m, 2H), 6.99 (t, 2H, J=8.7 Hz), 0.25 (s, 9H); $^{13}C$ NMR (75 MHz, $CDCl_3$) δ 162.6 (d, $J_{C-F}$=248 Hz), 133.9 (d, $J_{C-F}$=8 Hz), 119.3 (d, $J_{C-F}$=4 Hz), 115.5 (d, $J_{C-F}$=22 Hz), 104.0, 93.8, −0.07.

3-(4-Fluorophenyl)propiolic acid (Yonemoto-Kobayashi et al., *Org. Biomol. Chem.* 2013, 11, 3773-3775). CsF (4.74 g, 31.2 mmol) was loaded into an oven-dried 250-mL round bottom flask in a glovebox. The flask was removed from the glovebox, attached to a $CO_2$ balloon, equipped with a magnetic stirrer and a septum, and filled with anhydrous DMSO (60 mL). Neat ((4-fluorophenyl)ethynyl)trimethylsilane (5.00 g, 26.0 mmol) was added dropwise. The reaction mixture was stirred under $CO_2$ at room temperature overnight, diluted with water (600 mL) and washed with $CH_2Cl_2$ (2×150 mL). The aqueous layer was acidified at 0° C. to pH 1 with 6 M HCl and then extracted with $Et_2O$ (3×200 mL). The combined organic layers were dried ($MgSO_4$), filtered, and concentrated in vacuo to afford 3-(4-fluorophenyl)propiolic acid (3.02 g, 18.4 mmol, 71%) as an orange solid: $^1$H NMR (400 MHz, Acetone-$d_6$) δ 11.74 (brs, 1H), 7.71 (dd, 2H, J=8.6, 5.6 Hz), 7.26 (t, 2H, J=8.6 Hz); $^{13}$C NMR (100 MHz, Acetone-$d_6$) δ 164.8 (d, $J_{C-F}$=249 Hz), 154.7, 136.1 (d, $J_{C-F}$=9 Hz), 117.1 (d, $J_{C-F}$=23 Hz), 84.6, 81.8.

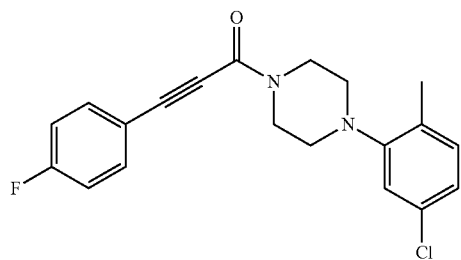 [SMILES: Cc1ccc(Cl)cc1N1CCN(C(=O)C#Cc2ccc(F)cc2)CC1]

1-(4-(5-Chloro-2-methylphenyl)piperazin-1-yl)-3-(4-fluorophenyl)prop-2-yn-1-one To a solution of 3-(4-fluorophenyl)propiolic acid (3.00 g, 18.3 mmol) in anhydrous $CH_2Cl_2$ (180 mL) at 0° C. was added 1-(5-chloro-2-methylphenyl)piperazine (4.62 g, 21.9 mmol), and $Et_3N$ (6.35 mL, 45.7 mmol), followed by dropwise addition of T3P (50 wt. % solution in EtOAc, 19.4 mL, 27.4 mmol). The reaction mixture was stirred at 0° C. for 30 min, warmed to room temperature overnight, diluted with $CH_2Cl_2$ (200 mL), washed with 1 M HCl (150 mL), dried ($MgSO_4$), filtered, and concentrated in vacuo. The residue was purified by chromatography on $SiO_2$ (2:1, hexanes/EtOAc) to give 1-(4-(5-chloro-2-methylphenyl)piperazin-1-yl)-3-(4-fluorophenyl)prop-2-yn-1-one (5.22 g, 14.6 mmol, 80%) as an off white solid: Mp 138.7-140.4° C.; IR (neat) 2924, 2216, 1625, 1596, 1504, 1443, 1431, 1219, 1038, 837 cm$^{-1}$; $^1$H NMR (300 MHz, CDCl$_3$) δ 7.55 (dd, 2H, J=7.5, 5.4 Hz), 7.12-6.94 (m, 5H), 3.96 (app t, 2H, J=4.8 Hz), 3.82 (app t, 2H, J=4.8 Hz), 2.95 (app t, 2H, J=4.8 Hz), 2.87 (app t, 2H, J=4.8 Hz), 2.28 (s, 3H); $^{13}$C NMR (75 MHz, CDCl$_3$) δ 163.5 (d, $J_{C-F}$=251 Hz), 153.0, 151.7, 134.5 (d, $J_{C-F}$=9 Hz), 132.1, 131.8, 130.9, 123.7, 119.8, 116.4 (d, $J_{C-F}$=4 Hz), 116.0 (d, $J_{C-F}$=23 Hz), 89.9, 80.9, 51.9, 51.3, 47.4, 41.8, 17.3; HRMS (ESI) m/z calcd for $C_{20}H_{19}ClFON_2$ ([M+H]$^+$) 357.1164, found 357.1165.

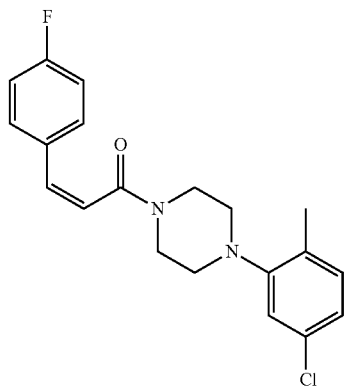 [SMILES: Cc1ccc(Cl)cc1N1CCN(C(=O)/C=C\c2ccc(F)cc2)CC1]

(Z)-1-(4-(5-Chloro-2-methylphenyl)piperazin-1-yl)-3-(4-fluorophenyl)prop-2-en-1-one To a solution of 1-(4-(5-chloro-2-methylphenyl)piperazin-1-yl)-3-(4-fluorophenyl)prop-2-yn-1-one (5.00 g, 14.0 mmol) in dry EtOAc (140 mL) was added Lindlar's catalyst (5% Pd on CaCO$_3$, lead poisoned, 0.298 g, equivalent to 1 mol % Pd) and quinoline (0.83 mL, 7.01 mmol). The reaction vessel was placed under vacuum, backfilled with H$_2$ (balloon, 2×) and allowed to stir at room temperature for 6 h. Analysis by TLC (2:1, hexanes/EtOAc) indicated that 1-(4-(5-chloro-2-methylphenyl)piperazin-1-yl)-3-(4-fluorophenyl)prop-2-yn-1-one had been mostly consumed. The reaction mixture was filtered through Celite, washed with EtOAc, and concentrated under vacuum. The combined organic layers were washed with 1 M HCl, dried (MgSO$_4$), filtered, and concentrated in vacuo. The crude material was purified by chromatography on SiO$_2$ (1:1, hexanes/EtOAc) to afford (Z)-1-(4-(5-chloro-2-methylphenyl)piperazin-1-yl)-3-(4-fluorophenyl)prop-2-en-1-one (3.15 g, 8.78 mmol, 63%, 87% brsm) as a colorless solid: IR (neat) 2913, 2239, 1616, 1506, 1437, 1223, 837, 725 cm$^{-1}$; $^1$H NMR (400 MHz, CDCl$_3$) δ 7.41-7.36 (m, 2H), 7.08-7.02 (m, 3H), 6.96 (dd, 1H, J=8.1, 2.1 Hz), 6.80 (d, 1H, J=2.1 Hz), 6.66 (d, 1H J=12.5 Hz), 6.05 (d, 1H, J=12.5 Hz), 3.80 (m, 2H, J=5.0 Hz), 3.49 (t, 2H, J=5.0 Hz), 2.80 (t, 2H, J=5.0 Hz), 2.53 (t, 2H, J=5.0 Hz), 2.21 (s, 3H); $^{13}$C NMR (100 MHz, CDCl$_3$) δ 167.3, 162.7 (d, $J_{C-F}$=248 Hz), 151.7, 132.6, 132.0, 131.8, 131.5 (d, $J_{C-F}$=3 Hz), 132.1, 131.8, 130.9, 130.2 (d, $J_{C-F}$=8 Hz), 123.6, 122.7, 119.6, 115.6 (d, $J_{C-F}$=21 Hz), 51.4, 51.2, 46.5, 41.5, 17.3; HRMS (ESI) m/z calcd for $C_{20}H_{21}ClFON_2$ ([M+H]$^+$) 359.1321, found 359.1329.

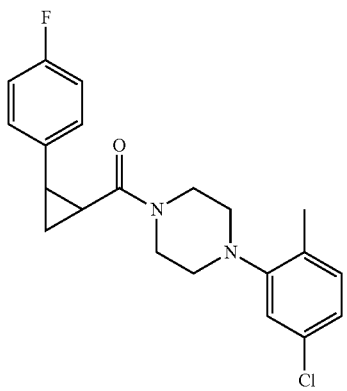

JJ-450

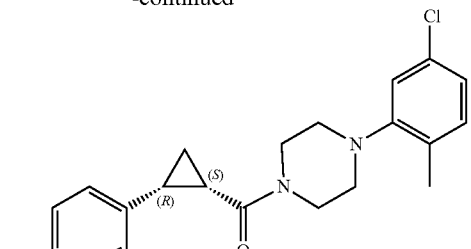

JJ-450A (−)-rotation
more potent isomer (4-(5-Chloro-2-methylphenyl)piperazin-1-yl)((1RS,2SR)-2-(4-fluorophenyl)cyclopropyl)-methanone (JJ-450)

THF (90 mL) was degassed by sparging with Ar for 60 min and treated at room temperature under Ar atmosphere with anhydrous CrCl$_2$ (6.43 g, 51.8 mmol) followed by (Z)-1-(4-(5-chloro-2-methylphenyl)piperazin-1-yl)-3-(4-fluorophenyl)prop-2-en-1-one (3.10 g, 8.64 mmol) and CH$_2$ICl (3.36 mL, 43.2 mmol). The reaction mixture was stirred for 20 h at 80° C., cooled to room temperature, quenched by the addition of 1.0 M aqueous HCl (300 mL) and extracted with EtOAc (3×300 mL). The combined organic layers were filtered through a plug of basic Al$_2$O$_3$, and concentrated in vacuo. The residue was purified by chromatography on SiO$_2$ (1:1, hexanes/EtOAc) to afford an oil that was further purified twice by chromatography on basic Al$_2$O$_3$ (1:1, hexanes/EtOAc) to give (4-(5-chloro-2-methylphenyl)piperazin-1-yl)((1RS,2SR)-2-(4-fluorophenyl)cyclopropyl)methanone (2.76 g, 7.41 mmol, 86%) as a clear oil that solidified after storage on high vacuum overnight: Mp 78.2-80.4° C. (hexanes); IR (CH$_2$Cl$_2$) 2936, 1637, 1592, 1510, 1487, 1435, 1223, 1033, 837, 815 cm$^{-1}$; $^1$H NMR (400 MHz, CDCl$_3$) δ 7.16-7.11 (m, 2H), 7.07 (dd, 1H, J=8.1, 0.5 Hz), 7.00-6.94 (m, 3H), 6.73 (d, 1H, J=2.1 Hz), 3.81-3.76 (m, 1H), 3.71-3.60 (m, 2H), 3.36 (ddd, 1H, J=12.4, 8.8, 3.1 Hz), 2.79-2.71 (m, 2H), 2.45 (td, 1H, J=8.8, 7.0 Hz), 2.35-2.29 (m, 1H), 2.26-2.16 (m, 5H), 1.83 (dt, 1H, J=7.0, 5.6 Hz), 1.35 (td, 1H, J=8.8, 5.6 Hz); $^{13}$C NMR (100 MHz, CDCl$_3$) δ 167.2, 161.7 (d, J$_{C-F}$=244 Hz), 151.9, 133.1 (d, J$_{C-F}$=3 Hz), 131.9 (d, J$_{C-F}$=14 Hz), 130.9, 129.1 (d, J$_{C-F}$=8 Hz), 123.6, 119.7, 115.0 (d, J$_{C-F}$=21 Hz), 51.8, 51.6, 45.6, 42.2, 23.8, 23.5, 17.3, 10.7; HRMS (ESI) m/z calcd for C$_{21}$H$_{23}$ClFON$_2$ ([M+H]$^+$) 373.1477, found 373.1478.

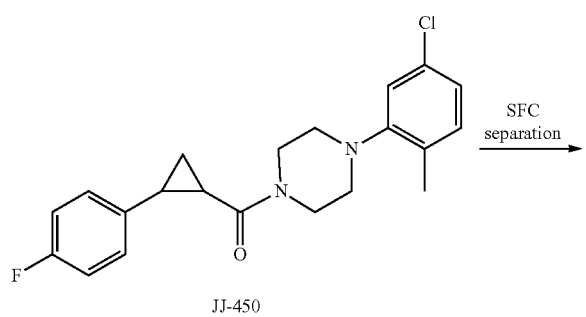

JJ-450 → SFC separation

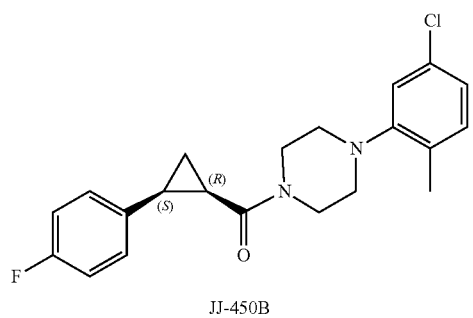

JJ-450B

Racemic JJ-450 was separated on a SFC Chiralpak-IC semiprep (250×10 mm) column (20% MeOH, 6 mL/min, 220 nM, P=100) to afford (4-(5-chloro-2-methylphenyl)piperazin-1-yl)((1S,2R)-2-(4-fluorophenyl)cyclopropyl)methanone JJ-450A (retention time 13.1 min) as a colorless viscous oil (100% purity by ELSD): [α]$^{20}_D$ −118.7 (c 0.39, CHCl$_3$); $^1$H NMR (300 MHz, CDCl$_3$) δ 7.17-7.10 (m, 2H), 7.07 (d, 1H, J=8.1 Hz), 7.02-6.94 (m, 3H), 6.72 (d, 1H J=2.1 Hz), 3.83-3.75 (m, 1H), 3.72-3.58 (m, 2H), 3.39-3.31 (m, 1H), 2.81-2.69 (m, 2H), 2.45 (td, 1H, J=8.7, 6.9 Hz), 2.36-2.25 (m, 1H), 2.25-2.15 (m, 5H), 1.83 (dt, 1H, J=6.9, 5.5 Hz), 1.35 (td, 1H, J=8.7, 5.5 Hz); HRMS (ESI) m/z calcd for C$_{21}$H$_{23}$ClFON$_2$ ([M+H]$^+$) 373.1477, found 373.1476. The enantiomeric excess was 100% ee (SFC Chiralpak-IC (250×4.6 mm); 20% MeOH, 220 nM, 2 mL/min; retention time: 9.8 min).

(4-(5-Chloro-2-methylphenyl)piperazin-1-yl)((1R,2S)-2-(4-fluorophenyl)cyclopropyl)-methanone JJ-450B (retention time 16.5 min) was obtained as a colorless viscous oil (100% purity by ELSD): [α]$^{20}_D$+117.4 (c 0.38, CHCl$_3$); $^1$H NMR (300 MHz, CDCl$_3$) δ 7.17-7.10 (m, 2H), 7.07 (d, 1H, J=8.1 Hz), 7.01-6.94 (m, 3H), 6.72 (d, 1H, J=2.1 Hz), 3.82-3.74 (m, 1H), 3.71-3.60 (m, 2H), 3.39-3.30 (m, 1H), 2.81-2.68 (m, 2H), 2.45 (td, 1H, J=8.6, 7.0 Hz), 2.35-2.26 (m, 1H), 2.25-2.15 (m, 5H), 1.83 (dt, 1H, J=7.0, 5.6 Hz), 1.35 (td, 1H, J=8.6, 5.6 Hz); HRMS (ESI) m/z calcd for C$_{21}$H$_{23}$ClFON$_2$ ([M+H]$^+$) 373.1477, found 373.1476. The enantiomeric excess was 100% ee (SFC Chiralpak-IC (250×4.6 mm); 20% MeOH, 220 nM, 2 mL/min; retention time: 12 min).

Example 3

Activity of Compounds in PSA Luciferase Assay

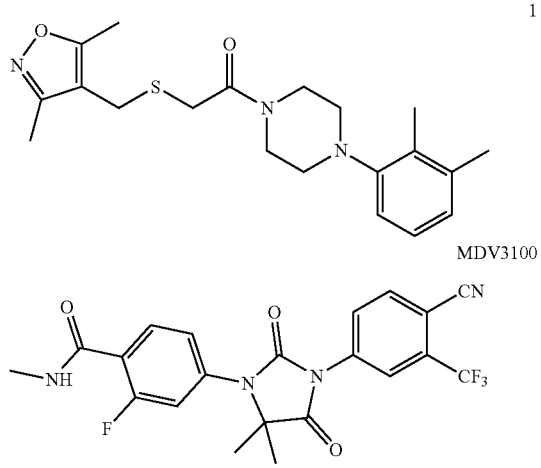

The biological activity of analogs 5-16, 18, 20, 26, JJ-450, and the resolved enantiomers JJ-450A and J-450B was determined and compared to HTS hit 1 (IC$_{50}$ 7.3 µM) and MDV3100 (IC$_{50}$ 1.1 µM) using the Dual-Glo luciferase system (Promega, WI, USA) in C4-2-PSA-rl cells, which were generated by transfection with PSA6.1-luc and pRL-TK followed by stable selection using G418 and puromycin. C4-2-PSA-rl stable cells were cultured in RPMI 1640 medium with 10% FBS, 1% penicillin-streptomycin, 1% L-glutamine, 10 mg/mL puromycin, and 50 mg/mL G418. C4-2-PSA-rl cells were seeded in 24-well plates such that they reached 75-80% cell monolayer density after 24 h. C4-2-PSA-rl cells were then treated for 24 h with 0, 0.2, 0.8, 3.2, 12.8, or 25 µM of each compound dissolved in DMSO (0.8% DMSO/well) in the presence of 1 nM synthetic androgen R1881, with each experimental condition in triplicate. The cells were also treated in parallel with 12.8 µM compound 1 and 12.8 µM MDV3100 as positive controls. Each compound was tested in at least two independent experiments. Luciferase activity was assayed using the Dual-Luciferase® Reporter Assay System (Promega) using LMax II Microplate Reader (Molecular Devices). The luciferase assay results were acquired using SoftMax Pro5.45 software (Molecular Devices) and analyzed using GraphPad Prism. PSA6.1-luc activity was normalized to the Renilla luciferase activity. Relative luciferase activity was calculated as the quotient of androgen-induced PSA-firefly/Renilla luciferase activity. Since PSA promoter activity correlates to AR transcriptional activity, inhibition of AR will result in decreased PSA-luciferase activity. IC$_{50}$ values were calculated using GraphPad Prism and data represent the mean and SD of 2-6 independent experiments (Table 2).

TABLE 2

In vitro activity of analogs in the PSA luciferase assay in C4-2-PSA-rl cells.

| Entry | Compound | IC$_{50}$ (µM) |
| --- | --- | --- |
| 1 | 1 | 7.3 ± 2.5[c] |
| 2 | 5a | >25[a] |
| 3 | 5b | 14.5 ± 3.2[b] |
| 4 | 5c | >25[a] |
| 5 | 5d | >25[a] |
| 6 | 5e | 12.0 ± 1.6[b] |
| 7 | 5f | 12.6 ± 7.7[b] |
| 8 | 5g | 11.1 ± 5.3[b] |
| 9 | 5h | >25[a] |
| 10 | 5i | 18.4 ± 9.2[b] |
| 11 | 5j | 11.1 ± 3.3[a] |
| 12 | 5k | 3.1 ± 1.1[a] |
| 13 | 5l | 14.7 ± 4.4[a] |
| 14 | 5m | 16.6 ± 4.8[b] |
| 15 | 6 | 10.8 ± 5.7[b] |
| 16 | 7 | 13.7 ± 0.8[b] |
| 17 | 8 | 14.4 ± 3.7[b] |
| 18 | 9 | >25[a] |
| 19 | 10 | 20.3 ± 11.6[a] |
| 20 | 11 | >25[a] |
| 21 | 12 | >25[b] |
| 22 | 13 | 16.1 ± 3.3[b] |
| 23 | 14 | 12.7 ± 0.8[a] |
| 24 | 15 | 2.9 ± 1.0[b] |
| 25 | 16 | >25[b] |
| 26 | 18a | >25[b] |
| 27 | 18b | >25[b] |
| 28 | 18c | 7.2 ± 2.7[c] |
| 29 | 20a | >25[a] |
| 30 | 20b | >25[c] |
| 31 | 26a | 7.7 ± 1.6[b] |
| 32 | 26b | 7.9 ± 2.8[a] |
| 33 | JJ-450 | 2.7 ± 1.1 |
| 34 | JJ-450A | 1.6 ± 0.1 |
| 35 | JJ-450B | 13.1 ± 1.8 |
| 36 | MDV3100 | 1.1 ± 0.5[e] |

Assay repeats:
[a] n = 2;
[b] n = 3;
[c] n = 4;
[d] n = 5;
[e] n = 6.

Modifications of the substituents on the benzene ring in zone 1 revealed that methyl groups in the 3- and 4-positions (5c, 5d) led to loss of activity, while the 2-methyl analog 5b (IC$_{50}$ 14.5 µM) retained about half of the activity of the 2,3-demethylated 1 (Table 2). Removal of the 2-methyl group in 5a deleted activity. In agreement with this trend in zone 1, the bulky 1-naphthyl substituent (5g) recovered activity (IC$_{50}$ 11.1 µM). Analogs with electron-withdrawing substituents at the benzene 2-position (2-NC, 5e, and 2-F, 5f) also maintained or slightly increased activity (IC$_{50}$ 12-13 µM); however, the electron-donating 2-methoxy substituted 5h was not tolerated and resulted in a complete loss of activity, possibly due to an increase in the pKa of the aniline and/or an unfavorable increase in the t-electron density of the aromatic ring.

The piperazine core (zone 2) was queried through substitutions with flexible as well as constrained acyclic and cyclic diamines. The flexible N,N'-dimethylethylenediamine linker in 5i (IC$_{50}$ 18.4 µM) and the 7-membered diazepane 5j (IC$_{50}$ 11.1 µM) both conserved activity. The demethylated piperazines 5l and 5m (IC$_{50}$ 15-17 µM) were both also almost as active as the initial hit. In contrast, the conformationally more highly constraint 2,6-dimethylpiperazine 5k was considerably more active with an IC$_{50}$ of 3.1 µM. Installment of an ethylene bridge and a carbon-linked (2-Me)Ph group decreased activity again, since both diastereomers of the bicyclo[3.2.1] ring systems 26a and 26b, showed an IC$_{50}$ of 8 µM.

Reduction of amide 5b to amine 6 resulted in a 1.3-fold increase in activity to an $IC_{50}$ of 10.8 µM. Sulfonamide 18c ($IC_{50}$ 7.2 µM) was twice as active as the initial hit 1, but urea 20a and carbamate 20b were inactive.

The replacement of the thioether linkage in zone 2 with an ether group abolished activity in 18a. Substituting the thioether with the N-methylated amine in 18b also abolished activity. In contrast, in an analogous system with a phenyl group in place of the isoxazole, both thioether 7 as well as the all-carbon chain containing 8 showed constant activity ($IC_{50}$ 14 µM).

In order to verify that the biological effect in the thioether series was not a result of S-oxidation in the cellular assay, common products of thioether oxidation, i.e. sulfoxide 12 and sulfone 13, were tested. While sulfone 13 retained some activity ($IC_{50}$ 16.1 µM), sulfoxide 12 was inactive. Shortening the three-atom chain to afford the two-atom thioether-linked 9 also abolished activity. The rigidified alkyne 10 and the corresponding (E)-alkene 11 and its cyclopropane isostere 16 were also found to be essentially inactive. In contrast, the (Z)-alkene 14 surprisingly showed an $IC_{50}$ of 12.7 µM, and the corresponding cis-fused cyclopropane isostere 15 was even more potent than analog 1, showing an $IC_{50}$ of 2.9 µM (Table 2).

In summary, zone 1 modifications showed that the ortho-substituent on the phenyl ring was important for activity. In zone 2, the sterically encumbered 2,6-dimethylpiperazine proved superior to flexible, unsubstituted, and bridged analogs. In zone 3, a carbonyl group was not required, and a sulfonamide and even the reduced amine were well tolerated. In zone 4, thioether oxidation reduces activity, and only the cis-cyclopropane successfully and significantly improves the $IC_{50}$. Limited substitutions were performed in zone 5, but in general analogs with a phenyl group were equipotent with their 3,5-dimethylisoxazole congeners (see, for example, 7 vs 5b). Compounds 5k, 15, and JJ-450 (particularly JJ-450A) were found to be significantly more potent than 1. Compounds 15 and JJ-450 are of particular interest due to the isosteric replacement of the thioether linker with the metabolically more stable cyclopropane.

Compounds 559, 562, 475, 476, 484, and 458 are all also active in the PSA luciferase assay at sub-micromolar $EC_{50}$s (450-900 nM), and they are inactive against androgen receptor (AR) negative cell lines in cell proliferation assays.

Additional compounds are shown below:

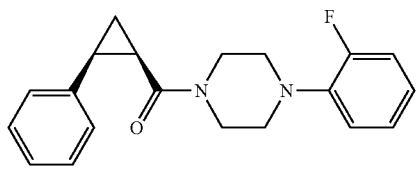

UPCMLD35AJKJ056582
Short # 582
Sample weight: 0.88 mg
Chemical Formula: $C_{20}H_{21}FN_2O$
Exact Mass: 324.16

-continued

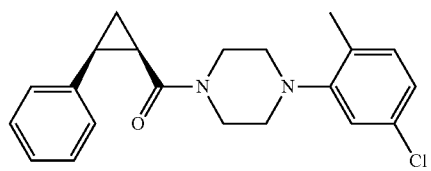

UPCMLD35AJKJ056583
Short # 583
Sample weight: 0.55 mg
Chemical Formula: $C_{21}H_{23}ClN_2O$
Exact Mass: 354.15

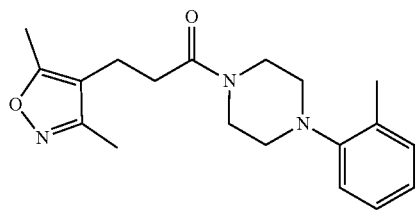

UPCMLD35AJKJ056588
Short # 588
Sample weight: 0.70 mg
Chemical Formula: $C_{19}H_{25}N_3O_2$
Exact Mass: 327.19

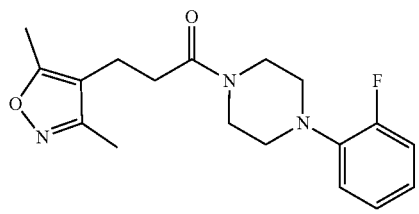

UPCMLD35AJKJ056589
Short # 589
Sample weight: 0.54 mg
Chemical Formula: $C_{18}H_{22}FN_3O_2$
Exact Mass: 331.17

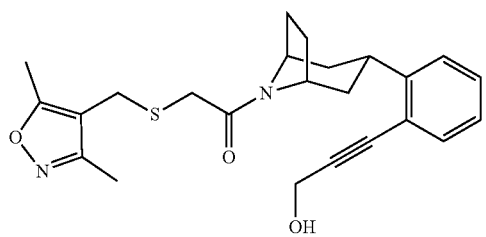

UPCMLD35AJKJ056571
Short # 571
Sample weight: 0.54 mg
Chemical Formula: $C_{24}H_{28}N_2O_3S$
Exact Mass: 424.18

-continued

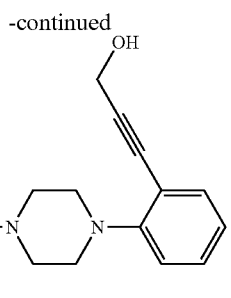

JKJ584-25
Short #: 425
Batch #: 1
Sample weight: 0.56 mg
Chemical Formula: $C_{23}H_{24}N_2O_2$
Exact Mass: 360.18

Figure 9C:
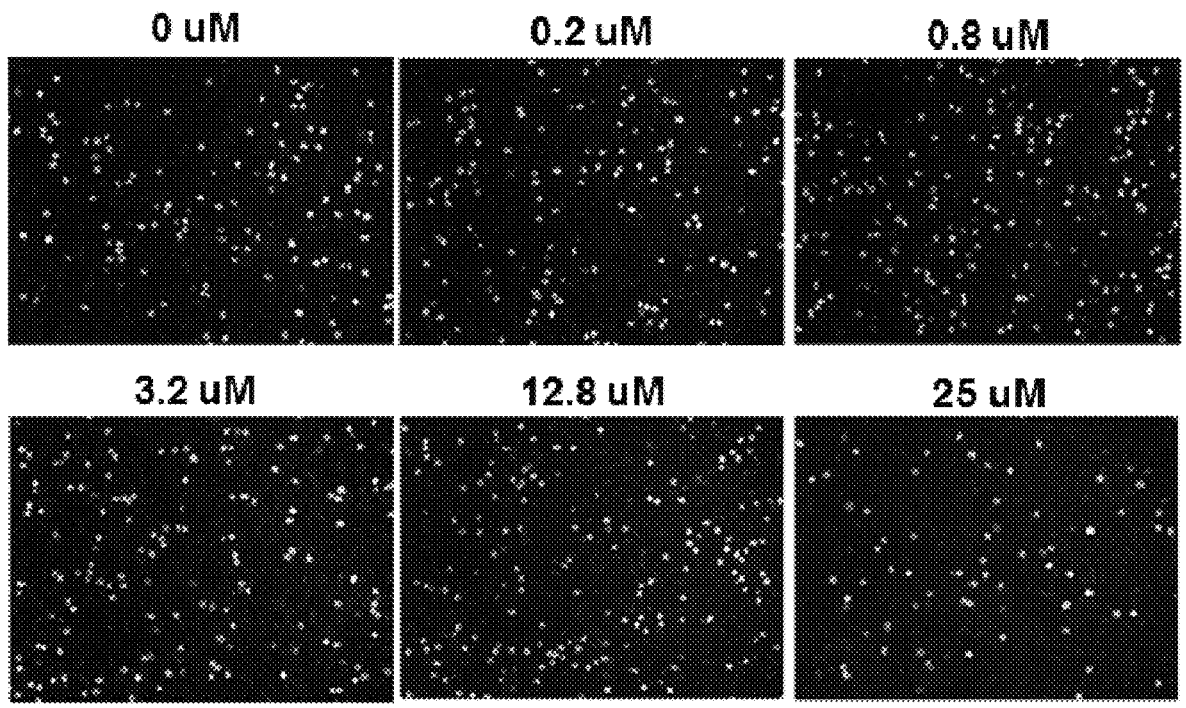
FIG. 9C shows the effect of analog #583 at indicated concentrations on PC3 cell proliferation in BrdU assay.

Compound #583 is very potent, with an $IC_{50}$>1 uM in inhibiting AR-dependent PSA promoter activity (FIG. 9A). As expected, #583 inhibited proliferation of AR-positive C4-2 (FIG. 9B), but not AR-negative PC3 (FIG. 9C), prostate cancer cells. Also, #583 does not contain a sulfur atom in the structure and should therefore be more resistant to oxidative metabolic degradation than the sulfur-containing compounds.

Figure 10:
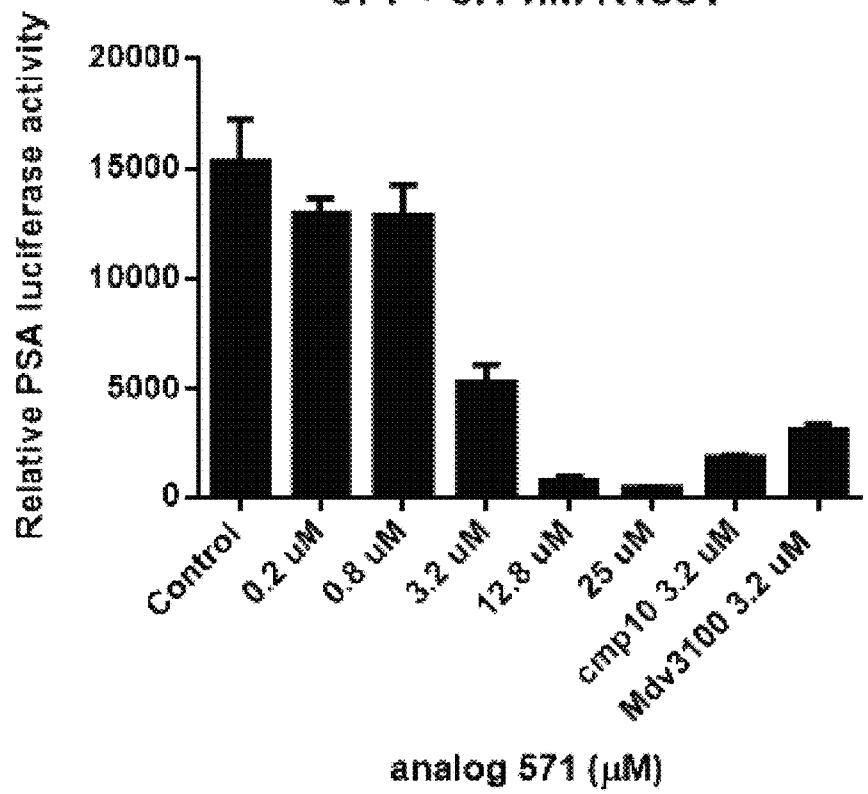
FIG. 10 is a graph showing the effect of compound #571 at indicated concentrations on PSA-driven luciferase activity in C4-2 cells.

Compounds #571 and #425 were developed for conjugation to agarose matrix. #571 is quite active, with an $IC_{50}$ of ~3 uM in the inhibition of AR activation of PSA promoter in a luciferase assay (FIG. 10).

Example 4

Inhibition of Xenograft Tumor Growth by JJ-450

Figure 11:
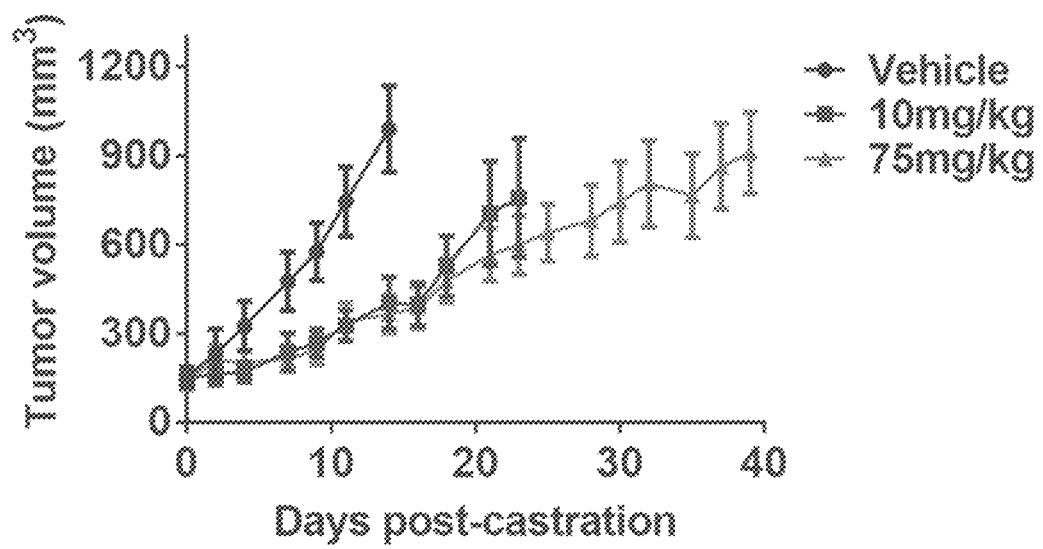
FIG. 11 is a graph showing the effect of compound JJ-450 at indicated concentrations on 22Rv1 xenograft tumor volume. JJ-450 was injected i.p. daily.

22Rv 1 xenograft tumors were established in SCID mice by subcutaneous injection of $2\times10^6$ cells in Matrigel. Once the tumors reached ~150 µL in volume, the mice were castrated and randomized into 3 groups for daily IP injection of vehicle (n=11), 10 mg/kg (n=11) and 75 mg/kg (n=11) groups. Injection of JJ-450 was initiated at time of castration. Tumor volumes were measured 3 times every week. As shown in FIG. 11, compound JJ-450 significantly inhibited tumor growth. Error bars, SEM.

Figure 12:
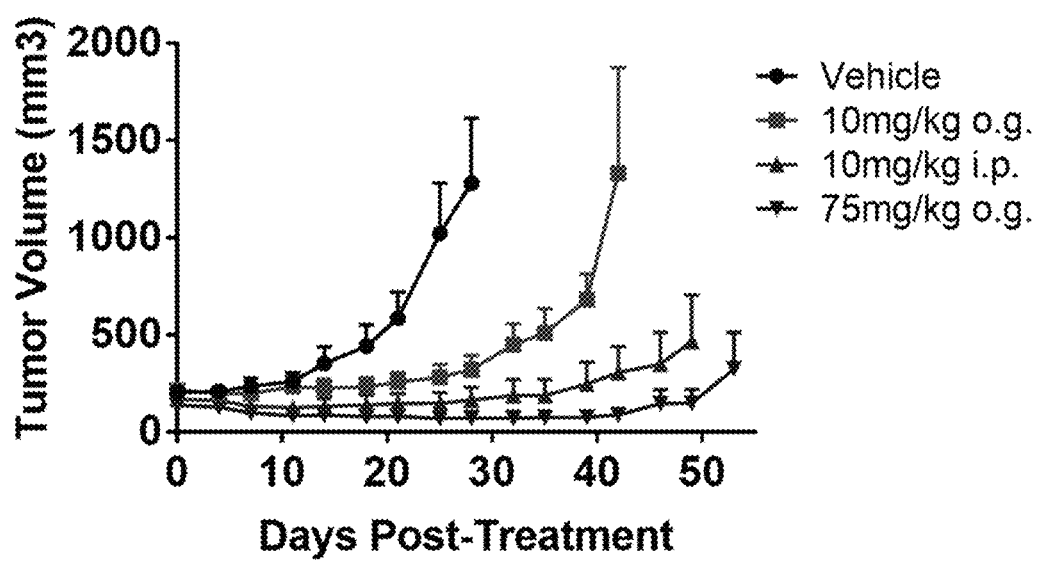
FIG. 12 is a graph showing the effect of compound JJ-450 at indicated concentrations and administration route on LNCaP xenograft tumor volume. JJ-450 was administered 6 times, from Monday to Saturday, every week

LNCaP xenograft tumors were established in SCID mice by subcutaneous injection of $2\times10^6$ cells in Matrigel. Once the tumors reached ~200 ul in volume, the mice were castrated and randomized into 4 groups: oral gavage of vehicle (n=6), oral gavage at 10 mg/kg (n=6), IP injection at 10 mg/kg (n=8), and oral gavage at 75 mg/kg (n=7) groups. Administration of JJ-450 was started 2 weeks after castration. Tumor volumes were measured twice every week. As shown in FIG. 12, compound JJ-450 significantly inhibited tumor growth. Error bars, SEM.

In view of the many possible embodiments to which the principles of the disclosed compounds, compositions and methods may be applied, it should be recognized that the illustrated embodiments are only preferred examples and should not be taken as limiting the scope of the invention.

What is claimed is:
1. A method for treating prostate cancer in a subject, comprising administering to the subject a therapeutically effective amount of a compound, or a pharmaceutically acceptable salt or ester thereof, selected from:

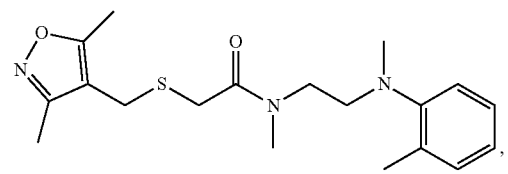

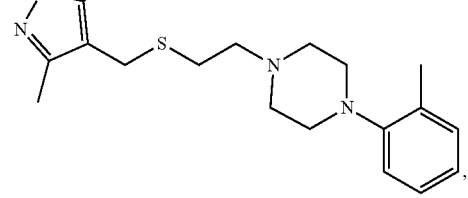

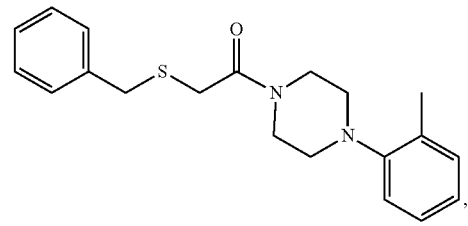

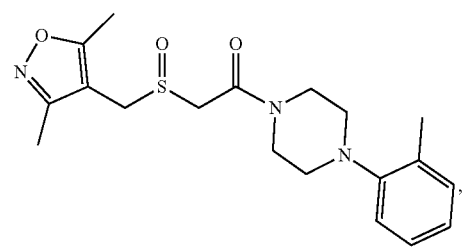

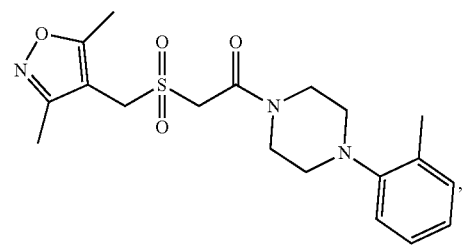

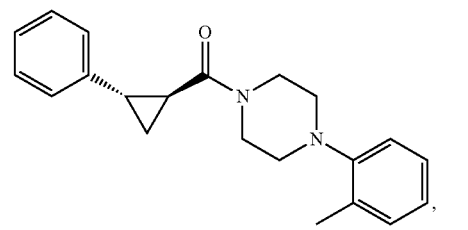

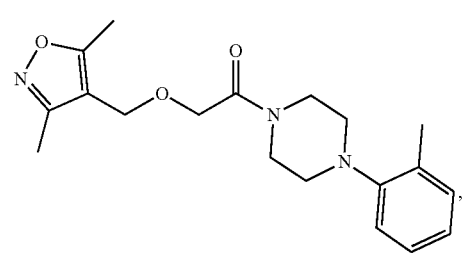

75
-continued
76
-continued
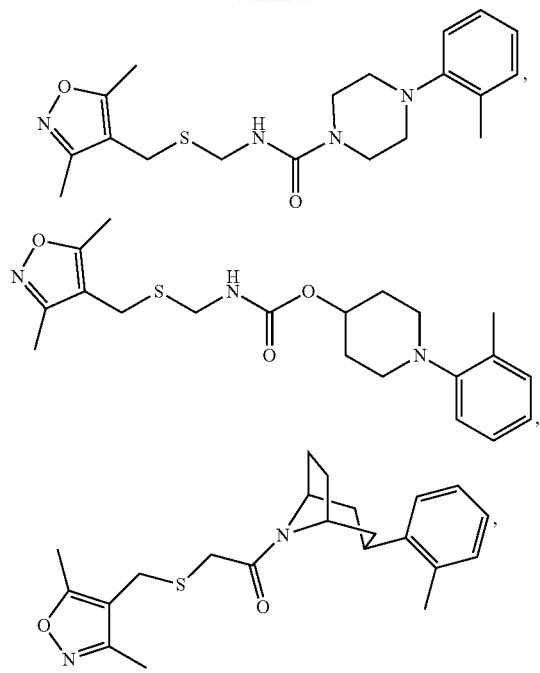
, or
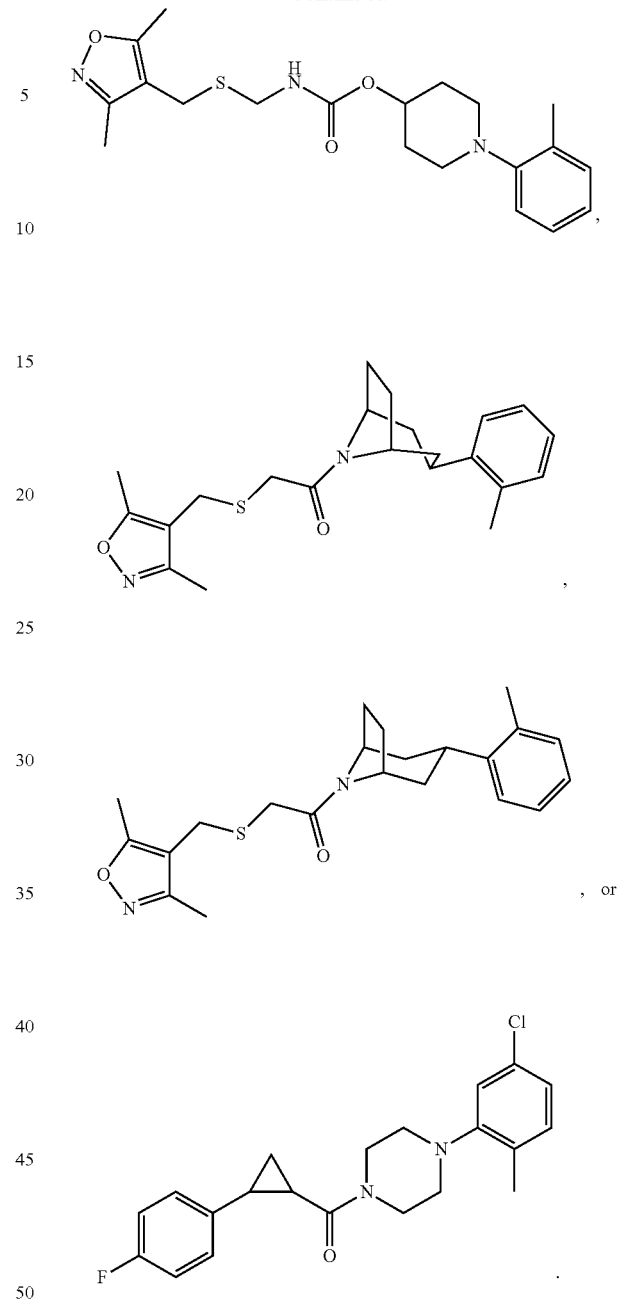
2. The method of claim 1, wherein the compound is:
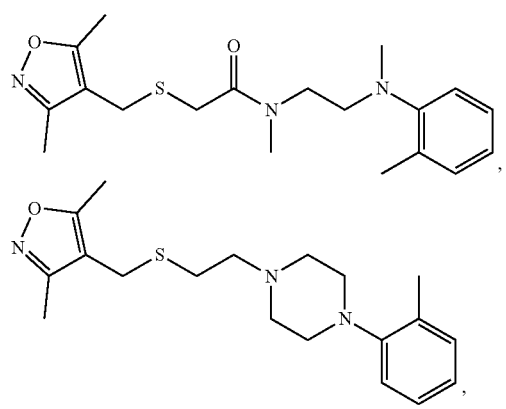
,
3. The method of claim 1, wherein the compound is:
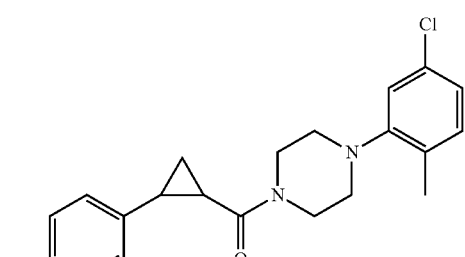
.

4. The method of claim 1, wherein the compound is:

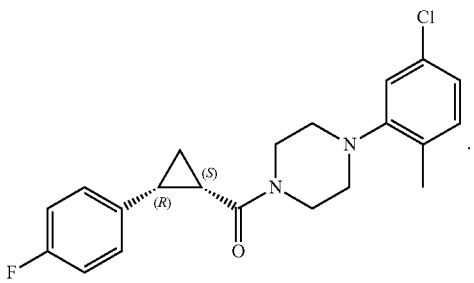

5. The method of claim 1, wherein the compound is:

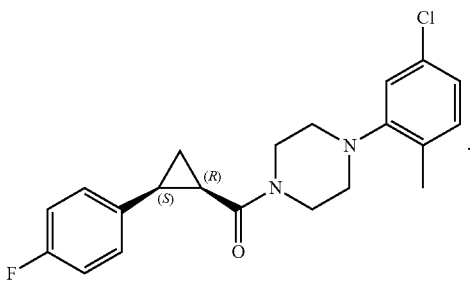

6. The method of claim 1, wherein administering a therapeutically effective amount of the compound comprises administering a pharmaceutical composition comprising the therapeutically effective amount of the compound and at least one pharmaceutically acceptable additive.

7. The method of claim 1, wherein the prostate cancer is castration-resistant prostate cancer.

8. The method of claim 1, wherein the compound is orally administered.

9. The method of claim 1, wherein the method is used in combination with androgen deprivation therapy.

10. The method of claim 1, wherein the agent is co-administered with abiraterone.

11. The method of claim 1, wherein the agent is co-administered with enzalutamide.

12. The method of claim 1, wherein the method further comprises identifying a subject that is in need of treatment with the agent.

13. The method of claim 1, wherein the therapeutically effective amount of the compound is from about 0.01 mg/kg body weight to about 20 mg/kg body weight.

14. The method of claim 1, wherein administering the therapeutically effective amount of the compound reduces a nuclear level of androgen receptor in castration-resistant prostate cancer (CRPC) cells relative to untreated CRPC cells.

15. The method of claim 14, wherein reducing the nuclear level of androgen receptor inhibits activation of the androgen receptor.

16. The method of claim 15, wherein a reduction in androgen receptor activation is determined by measuring prostate-specific antigen.

* * * * *

UNITED STATES PATENT AND TRADEMARK OFFICE
CERTIFICATE OF CORRECTION

PATENT NO. : 10,544,110 B2
APPLICATION NO. : 15/961475
DATED : January 28, 2020
INVENTOR(S) : Wipf et al.

Page 1 of 1

It is certified that error appears in the above-identified patent and that said Letters Patent is hereby corrected as shown below:

In the Specification

Column 1, Lines 24-25:
"grant #GM067082 awarded by the National Institutes of Health"
Should read:
--grant #sGM067082, CA186780, CA180995, CA047904, and CA211242, awarded by the National Institutes of Health, and grant #W81XWH – 16 – 1 – 0659, awarded by the Department of Defense--

Signed and Sealed this
Thirteenth Day of October, 2020

Andrei Iancu
*Director of the United States Patent and Trademark Office*